(12) United States Patent
Maruyama et al.

(10) Patent No.: US 10,627,412 B2
(45) Date of Patent: Apr. 21, 2020

(54) PERIODONTAL-DISEASE-SPECIFIC PEPTIDE, AND TREATMENT AND DIAGNOSIS OF PERIODONTAL DISEASE USING SAME

(75) Inventors: Ikuro Maruyama, Kagoshima (JP); Teruto Hashiguchi, Kagoshima (JP); Salunya Tancharoen, Bangkok (TH); Ko-ichi Kawahara, Kagoshima (JP); Kenji Tanaka, Hyogo (JP); Lyang-ja Lee, Hyogo (JP)

(73) Assignee: KAGOSHIMA UNIVERSITY, Kagoshima (JP)

( * ) Notice: Subject to any disclaimer, the term of this patent is extended or adjusted under 35 U.S.C. 154(b) by 0 days.

(21) Appl. No.: 13/635,519

(22) PCT Filed: Mar. 17, 2011

(86) PCT No.: PCT/JP2011/056469
§ 371 (c)(1),
(2), (4) Date: Dec. 17, 2012

(87) PCT Pub. No.: WO2011/115225
PCT Pub. Date: Sep. 22, 2011

(65) Prior Publication Data
US 2013/0086703 A1  Apr. 4, 2013

(30) Foreign Application Priority Data
Mar. 17, 2010  (JP) ................. 2010-061673

(51) Int. Cl.
| | |
|---|---|
| *G01N 33/68* | (2006.01) |
| *C07K 14/47* | (2006.01) |
| *C07K 16/18* | (2006.01) |
| *G01N 33/564* | (2006.01) |
| *A61K 38/00* | (2006.01) |

(52) U.S. Cl.
CPC ..... *G01N 33/6893* (2013.01); *C07K 14/4741* (2013.01); *C07K 16/18* (2013.01); *G01N 33/564* (2013.01); *A61K 38/00* (2013.01); *G01N 2333/4742* (2013.01); *G01N 2500/04* (2013.01); *G01N 2800/18* (2013.01)

(58) Field of Classification Search
None
See application file for complete search history.

(56) References Cited

U.S. PATENT DOCUMENTS 6,280,687 B1 * 8/2001 Golub et al. .................. 422/430

FOREIGN PATENT DOCUMENTS

| | | | |
|---|---|---|---|
| EP | 1983003 A2 | * | 10/2008 |
| JP | 2009-542191 | | 12/2009 |
| WO | WO 2008/021290 | * | 2/1998 |
| WO | 00/55628 | | 9/2000 |
| WO | WO 00/55628 | * | 9/2000 |
| WO | 03/056341 | | 7/2003 |
| WO | 2005/017530 | | 2/2005 |
| WO | 2006/132683 | | 12/2006 |
| WO | 2008/007807 | | 1/2008 |
| WO | 2008/021290 | | 2/2008 |
| WO | WO 2008021290 | * | 2/2008 |

OTHER PUBLICATIONS

Bendig et al. Methods: A Companion to Methods in Enzymology 1995; 8: 83-93.*
Brown et al. J Immunol. May 1996; 156(9):3285-91.*
Paul, Fundamental Immunology, 3rd Edition, 1993, pp. 292-295.*
Abbas et al. Cellular and Molecular Immunology 4th edition, 2000 Chapter 48 p. 42-43 and p. 48.*
Goel et al. J Immunol, 2004, 173 (12) 7358-7367.*
Torres et al. Trends in Immunology vol. 29, No. 2 p. 91-97.*
Ferrara et al. mAbs, 7:1, 32-41, 2015.*
Edwards et al (J. Mol. Biol. (2003) 334,103-118.*
Supplementary European Search Report and Search Opinion dated Jul. 18, 2013 in European Patent Application No. 11756409.6.
Theofilos Koutouzis et al., "Autroreactivity of Serum Immunoglobulin to Periodontal Tissue Components: A Pilot Study", J. Periodontal, vol. 80, No. 4, Apr. 2009, pp. 625-633.
E. Andrian et al., "*Porphyromonas gingivalis*-Epithelial Cell Interactions in Periodontitis", Journal of Dental Research, vol. 85, No. 5, 2006, pp. 392-403, XP8162803.
Georgios N. Belibasakis et al., "Regulation of RANKL and OPG gene expression in human gingival fibroblasts and periodontal ligament cells by *Porphyromonas gingivalis:* A putative role of the Arg-gingipains", Microbial Pathogenesis, vol. 43, No. 1, 2007, pp. 46-53, XP55065419.
W.S. McLaughlin et al., "Human gingival crevicular fluid keratin at healthy, chronic gingivitis and chronic adult periodontitis sites", Journal of Clinical Periodontology, vol. 23, Apr. 1996, pp. 331-335, XP008162826.

(Continued)

*Primary Examiner* — Oluwatosin A Ogunbiyi
(74) *Attorney, Agent, or Firm* — Wenderoth, Lind & Ponack, L.L.P.

(57) ABSTRACT

The present invention provides an inhibitor of an autoimmune response to a periodontal bacterial enzymatic degradation product of keratin in gingival epithelium in a mammal having a periodontal bacterium in the oral cavity, containing a substance having affinity to the keratin or a degradation product thereof and/or a substance having affinity to an autoantibody to the degradation product, an agent for the prophylaxis and/or treatment of a periodontal disease and/or a complication thereof; a RANKL expression inhibitor containing a substance having affinity to the keratin or a degradation product thereof; and a method of diagnosing a periodontal disease including detecting the keratin or a degradation product thereof and/or an autoantibody thereto.

4 Claims, 15 Drawing Sheets
Specification includes a Sequence Listing.

(56) References Cited

OTHER PUBLICATIONS

Tsute Chen et al., "*Porphyromonas gingivalis* Gingipains and Adhesion to Epithelial Cells", Infection and Immunity, vol. 69, No. 5, May 2001, pp. 3048-3056.
Hakimuddin T. Sojar et al., "Identification of glyceraldehyde-3-phosphate dehydrogenase of epithelial cells as a second molecule that binds to *Porphyromonas gingivalis* fimbriae", FEMS Immunology and Medical Microbiology, vol. 45, 2005, pp. 25-30, XP27804063.
M. Juhl et al., "Immunohistochemical distribution of keratin proteins in clinically healthy human gingival epithelia", Scandinavian Journal of Dental Research, vol. 97, 1989, pp. 159-170, XP8162796.
Database UniProt [Online] Nov. 1, 1996, "SubName: Full=Keratin K6; Flags: Fragment", XP002698676.
International Search Report dated May 24, 2011 in corresponding International Application No. PCT/JP2011/056469.
Hakimuddin T. Sojar et al., "*Porphyromonas gingivalis* Fimbriae Bind to Cytokeratin of Epithelial Cells", Infection and Immunity, vol. 70, No. 1, Jan. 2002, pp. 96-101.
Durga Reddi et al., "*Porphyromonas gingivalis* regulates the RANKL-OPG system in bone marrow stromal cells", Microbes and Infection, vol. 10, 2008, pp. 1459-1468.
I.C. Mackenzie et al., "Patterns of cytokeratin expression in the epithelia of inflamed human gingiva and periodontal pockets", J. Peridontal Res., vol. 28, 1993, pp. 49-59.

\* cited by examiner

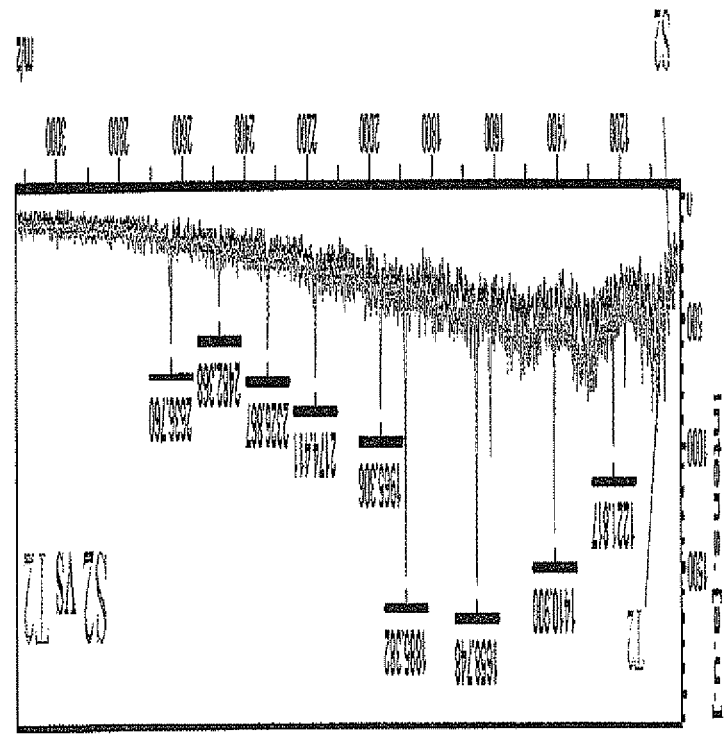
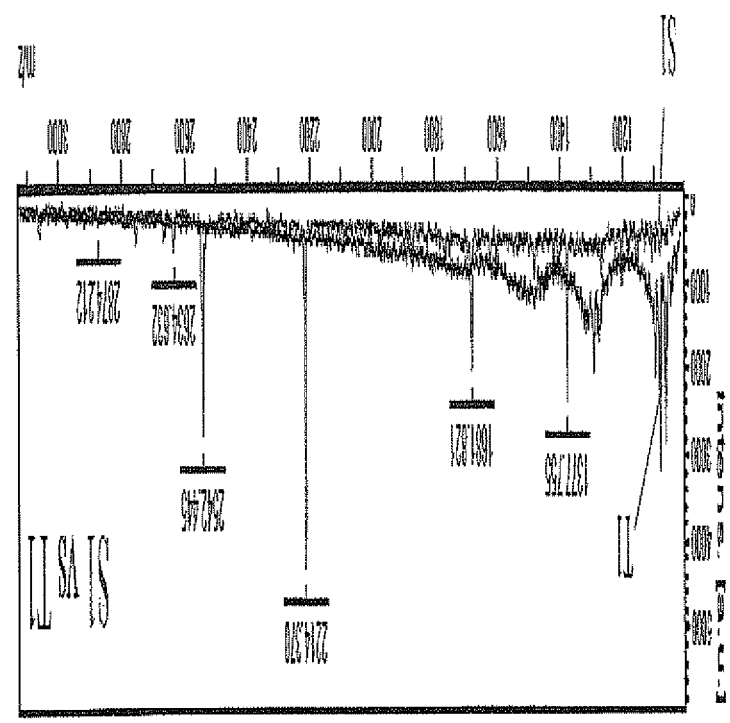
Fig.2

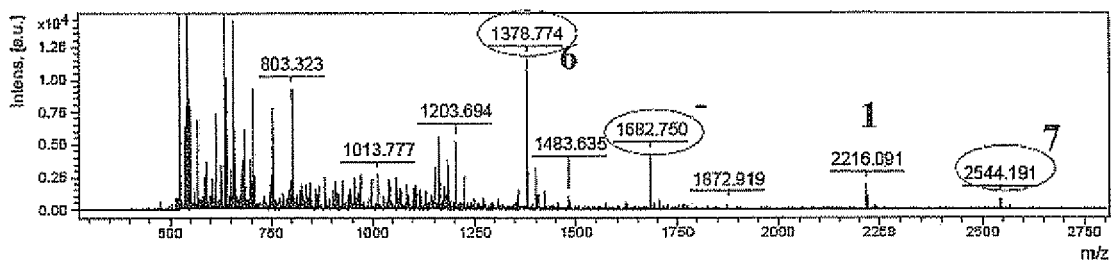

| No. | m/z | result | score | sequence |
|---|---|---|---|---|
| 6 | 1378 | KERATIN, TYPE II CYTOSKELETAL 6B | 34(yellow) | RTAAENEFVTLK |
| - | 1682 | Glutathione S-Transferase | 29(yellow) | YEEHLYERDEGDK |
| 1 | 2216 | KERATIN, TYPE II CYTOSKELETAL 6B | 25(yellow) | YEELQITAGRHGDDLRNTK |
| 7 | 2544 | KERATIN, TYPE II CYTOSKELETAL 6B | 7(green) | AQYEEIAQRSRAEAESWYQTK |

(b)

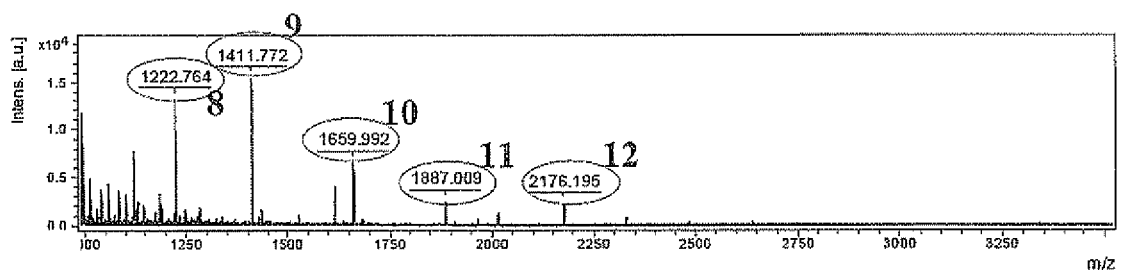

| No. | m/z | result | score | sequence |
|---|---|---|---|---|
| 8 | 1222 | KERATIN, TYPE I CYTOSKELETAL 17 | 34(yellow) | TKFETEQALR |
| 9 | 1411 | KERATIN, TYPE I CYTOSKELETAL 17 | 61(red) | DQYEKMAEKNR |
| 10 | 1659 | KERATIN, TYPE I CYTOSKELETAL 17 | 35(yellow) | TIVEEVQDGKVISSR |
| 11 | 1887 | KERATIN, TYPE I CYTOSKELETAL 17 | 23(green) | QFTSSSSIKGSSGLGGGSSR |
| 12 | 2176 | KERATIN, TYPE I CYTOSKELETAL 14 (Same to KERATIN, TYPE I CYTOSKELETAL 17) | 27(yellow) | EVATNSELVQSGKSEISELR |

Fig.9
A
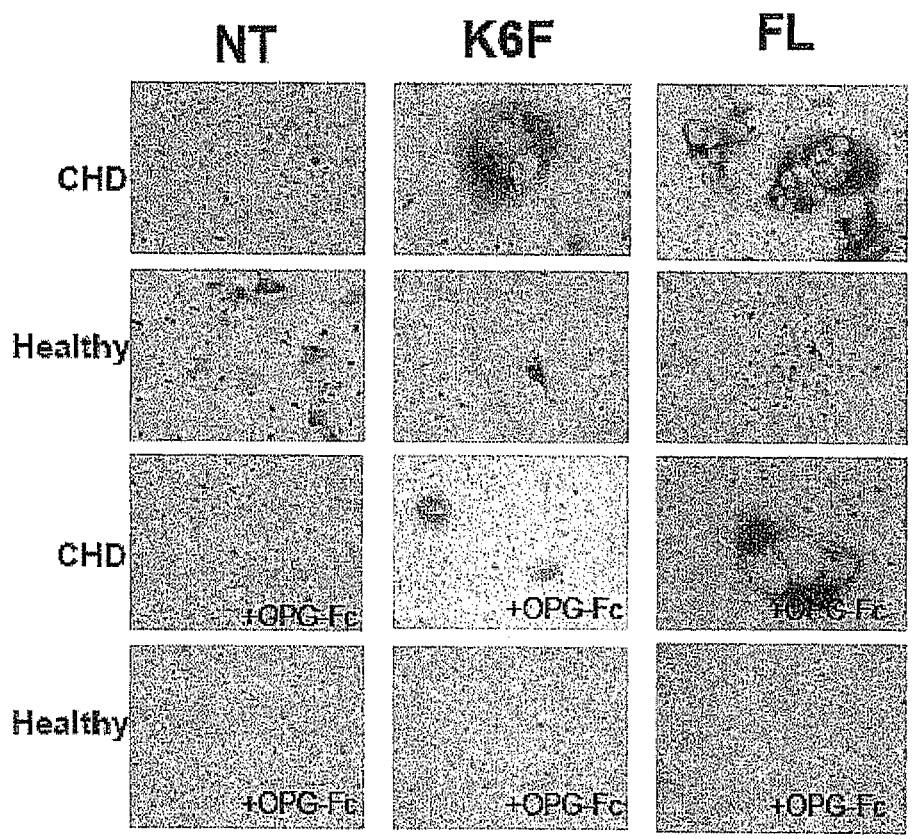
B
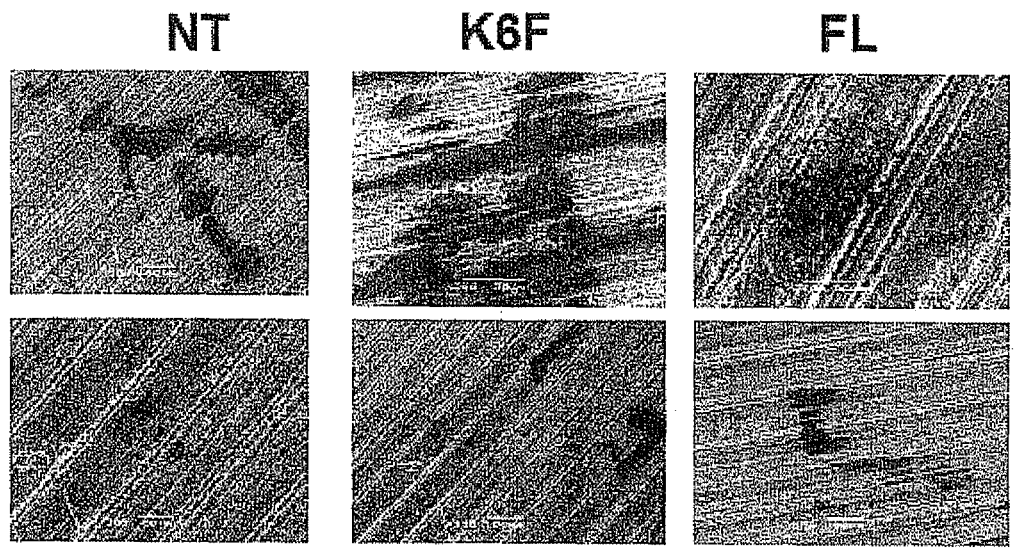

Fig.15
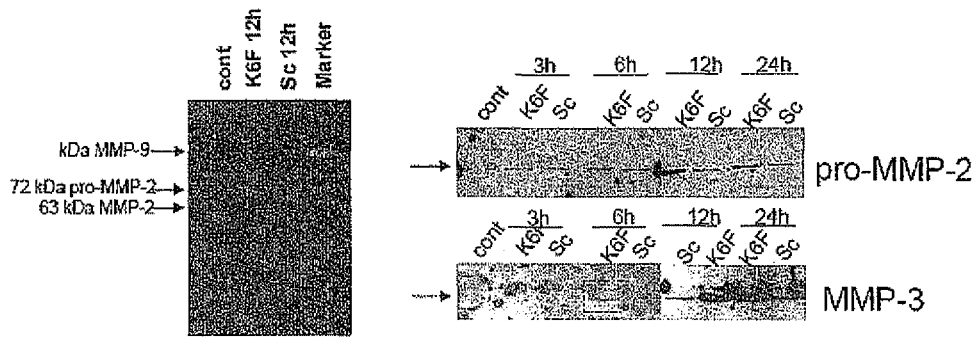
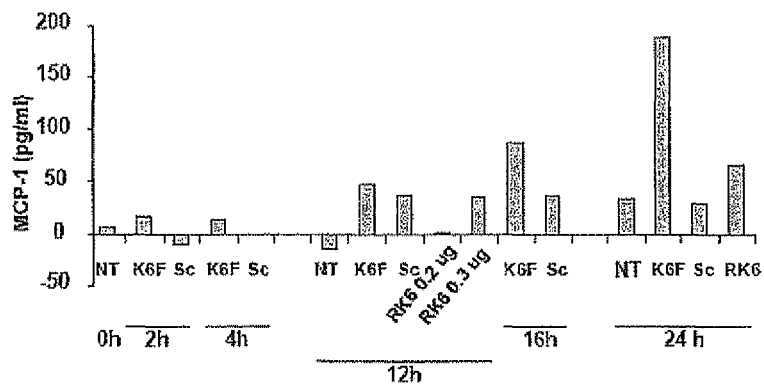
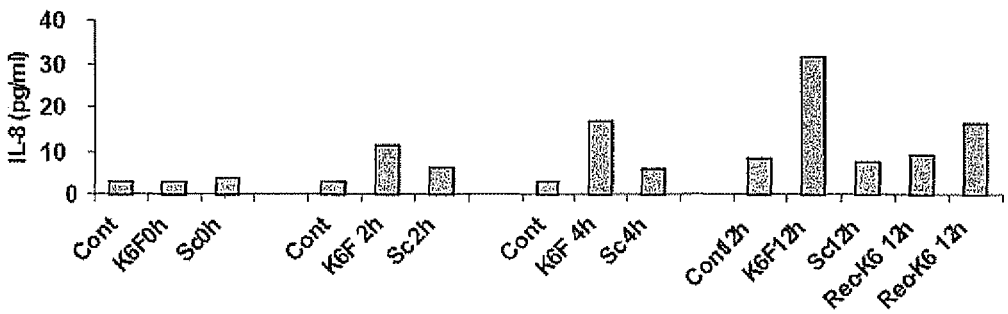
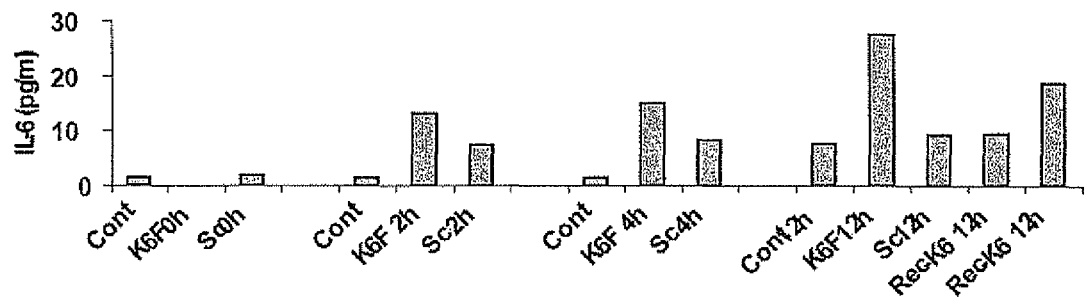

Fig.16
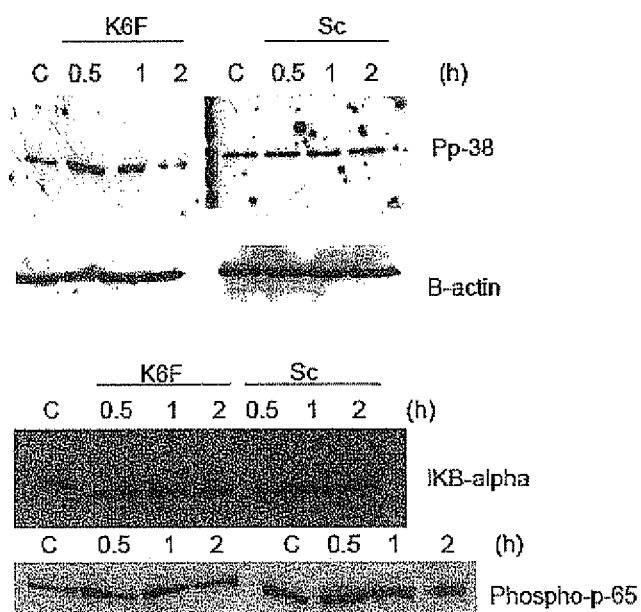
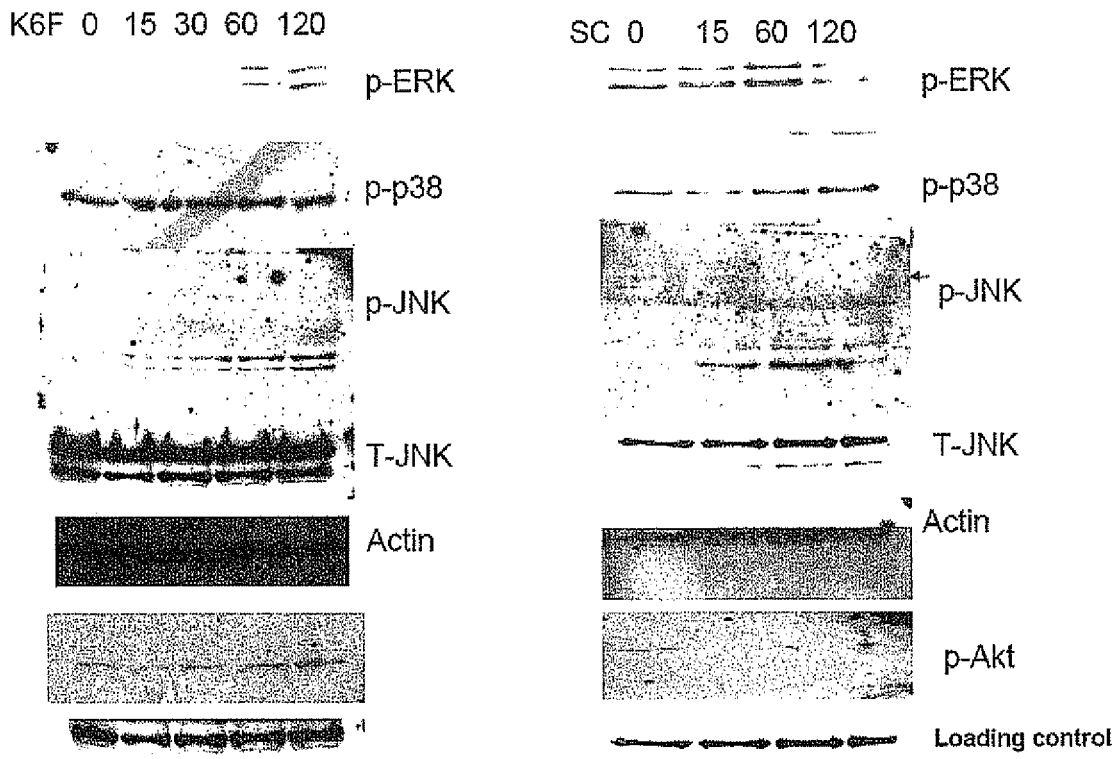

PERIODONTAL-DISEASE-SPECIFIC PEPTIDE, AND TREATMENT AND DIAGNOSIS OF PERIODONTAL DISEASE USING SAME

TECHNICAL FIELD

The present invention relates to a peptide expressed in a periodontal disease specific manner, a treatment and a diagnosis of said disease utilizing same, and the like.

BACKGROUND ART

Periodontal disease refers to a state with a disorder in any of gingiva, alveolar bone, cementum and periodontal membrane, which are periodontal tissues that support the teeth, and representative diseases include chronic marginal periodontitis and the like. Periodontal disease is a lifestyle-related disease found in about 80% of the adults, and developed by bacterial infection.

It has been suggested that once periodontal bacteria per se, toxic substances produced thereby, or leukocytes resistant to these bacteria or substances such as cytokine, prostaglandin and the like, which are released from leukocytes, enter the blood and are delivered to the organs in the body, they provide various undesirable influences on the body. For example, diabetes patients can easily have periodontal diseases and a periodontal disease may aggravate diabetes. In addition, it has been confirmed that periodontal disease is a high risk factor of heart diseases caused by arteriosclerosis, and that pregnant women with periodontal disease often have preterm delivery of low birth weight baby and the like.

Thus, since periodontal disease not only causes loss of teeth but is deeply involved in the onset and aggravation of a serious, possibly lethal medical problem, effective means for early diagnosis and treatment, as well as prevention, have been desired.

There are not less than 10 species of causative bacteria of periodontal diseases, of which the most important pathogenic bacterium is *Porphyromonas gingivalis* (non-patent document 1). *P. gingivalis* is an anaerobic Gram negative rod-shaped bacterium, which enters into dental plaque and releases enzymes such as protease and the like for its own survival. The enzymes cause inflammation of gingiva, and develop gingivitis which is the beginning of a periodontal disease.

The protease produced by *P. gingivalis* includes plural molecular species. Particularly, trypsin-like cysteine proteases (gingipain; HRgpA, RgpB, Kgp) are major enzymes produced by this bacterium, and various researches thereof have been made (non-patent documents 2 and 3). Through such researches, it has been suggested that gingipain plays a key role in the maintenance, growth and infection processes of *P. gingivalis*, and strenuous attempts have been made to develop inhibitors of those proteases for the purpose of treating and preventing periodontal diseases (patent documents 1-4, non-patent documents 4-7). However, the target protein of gingipain in the body is yet to be clarified and information is insufficient for, for example, the research and development and the like of a substrate mimicking inhibitor. Moreover, whether or not protein degradation products due to gingipain are involved in the onset or aggravation of periodontal diseases, or concurrence of systemic complications has not at all been elucidated yet.

On the other hand, as the situation stands, the only highly reliable method for understanding the state of periodontal diseases is measurement of the depth of gingival sulcus (periodontal pocket) by a dental expert (CPI test). For diagnosis of periodontal diseases using a biomarker, detection of bacterium-derived components, blood protein, inflammation related component and the like present in periodontal pocket and saliva has been proposed and, for example, an examination kit for detection of α1-antitrypsin (blood protein) and lactoferrin (inflammation-related component) in interdental liquid and the like are commercially available. In addition, it has been reported that detection of occult blood, alkaline phosphatase (bacterium-derived component), and leukocyte esterase (inflammation-related component) in saliva is effective for risk prediction of periodontal diseases. However, a biomarker permitting an early-stage and certain diagnosis of periodontal diseases has not been found, and there is almost no report relating to a blood biomarker.

In the meantime, with the progress of proteomics research including comprehensive analysis of protein expressed in vivo, a novel biomarker has been actively searched for by utilizing proteomics. Particularly, a study for search of a series of protein degradation products, which emerge in a certain disease in the disease specific manner due to the degradation of a particular target protein by a particular protease, as a biomarker of the disease is called degradomics, and is attracting attention not only as diagnosis of the disease but also as a search means for a new treatment target.

Keratin is a protein constituting an intermediate filament, which is a cytoskeleton of epithelial cells. In stratum corneum tissues such as nail, hair and the like, epithelial cells die by being filled with intermediate filaments consisting of specific keratin called rigid keratin and stiffen. Also in epithelial cells free of cornification such as mucosa and the like, keratin (cytokeratin) plays an important role as a protein constituting the intermediate filament, and the sheet structure of epithelial tissue maintains mechanical strength by the keratin fiber.

However, the relationship between periodontal diseases and periodontal bacterial enzymes and keratin has not been reported.

DOCUMENT LIST

Patent Documents patent document 1: JP-A-2004-143127
patent document 2: JP-A-2005-35909
patent document 3: JP-A-2003-335648
patent document 4: JP-A-2007-16002

Non-patent Documents non-patent document 1: Biology of the species *Porphyromonas gingivalis*, CRC Press, Inc., Florida (1993)
non-patent document 2: Clin. Infect. Dis. 28: 456-465 (1999)
non-patent document 3: Oral Microbiol. Immunol. 13: 263-270 (1998)
non-patent document 4: Infect. Immun. 70: 6968-6975 (2002)
non-patent document 5: Biol. Chem. 383: 1193-1198 (2002)
non-patent document 6: Antimicrob. Agents Chemother. 45: 2871-2876 (2001)
non-patent document 7: Biol. Chem. 384: 911-920 (2003)

SUMMARY OF THE INVENTION

Problems To Be Solved By The Invention

An object of the present invention is to provide a peptide that can be a diagnostic marker of a periodontal disease, particularly, a peptide which is a degradation product by periodontal bacterial enzyme, and an effective diagnosis method of a periodontal disease using the same. Another object of the present invention is to identify a peptide that can be a treatment target of a periodontal disease from among the aforementioned peptides and provide a novel therapeutic drug for a periodontal disease, which is based on a treatment concept of suppression of degradation of its parental protein and/or removal of the peptide. A still another object of the present invention is to provide a novel use of a periodontal bacterial enzyme and a substrate protein thereof, which utilizes the substrate specificity of the enzyme.

Means Of Solving The Problems

In an attempt to achieve the aforementioned objects, the present inventors have first tried to identify target proteins of gingipain in a periodontal disease. To be precise, rat gingival epithelial cells (also referred to as "GEC") were treated with any of three kinds of gingipain (HRgpA, RgpB, Kgp), and the peaks of the obtained degradation products were measured by mass spectrometry. As a result, peptides with molecular weights of about 2215 and about 2230 ("peptide 1" and "peptide 2", respectively) showing a remarkable increase as compared to no treatment and other gingipain treatment were found in Kgp-treated GEC. Similarly, in RgpB-treated GEC, peptides with molecular weights of about 2277 and about 2293 ("peptide 3" and "peptide 4", respectively) showing a remarkable increase as compared to no treatment and other gingipain treatment were found. Furthermore, a peptide with a molecular weight of about 2638 ("peptide 5") showing a remarkable increase as compared to no treatment and Kgp treatment was found in RgpB or HRgpA-treated GEC.

As a result of analysis of the amino acid sequences of peptides 1-5, these peptides were found to consist of partial amino acid sequences of 4 kinds of proteins classified as keratin (peptide 4 was an oxide of peptide 3). The corresponding human keratin protein was examined by homology search and, as a result, peptide 1 matched with a partial amino acid sequence of keratin 6, peptide 2 matched with a partial amino acid sequence of keratin 5, peptides 3 and 4 matched with a partial amino acid sequence of keratin 14, and peptide 5 matched with a partial amino acid sequence of keratin 17. Thus, human Keratin 6 was digested with Kgp, and human Keratin 17 was digested with RgpB, and the amino acid sequence of the peak of the enzymatic degradation product detected by mass spectrometry was analyzed. As a result, two peptides (peptide 6: molecular weight about 2216, peptide 7: molecular weight about 2544) were newly identified as Kgp degradation products of Keratin 6, and 5 peptides (peptide 8: molecular weight about 1222, peptide 9: molecular weight about 1411, peptide 10: molecular weight about 1659, peptide 11: molecular weight about 1887, peptide 12: molecular weight about 2176) were newly identified as RgpB degradation products of Keratin 17. The partial amino acid sequences corresponding to peptides 6 and 7 were also found in Keratin 5, and the partial amino acid sequences corresponding to peptides 8, 11 and 12 were also found in Keratin 14.

Then, to confirm actual, specific expression of the above-mentioned peptides obtained in vitro experiment in periodontal diseases, the present inventors have obtained dental plaque from interdental liquid of human patients with periodontal diseases and healthy subjects and examined the presence of the peptides therein by mass spectrometry. As a result, clear peaks of the peptides were detected only in periodontal disease patients. Furthermore, whether these peptides can be used as a blood biomarker was considered. As a result, several peptides including peptide 1 were detected (or significantly increased) in the sera of periodontal disease patients. From the above, it was confirmed that various gingipain degradation products of keratin can be mouth cavity and blood biomarkers of periodontal diseases.

Since a degradation product of keratin constituting the gingival epithelial tissue was detected in blood, the present inventors have predicted that the degradation product may play an important role in periodontal diseases as well as systemic complications associated with periodontal diseases, and first examined whether an autoimmune response to a degradation product occurred. As a result of drug-induced lymphocyte stimulation test (DLST), a sample testing positive to keratin 6 and a degradation product thereof (i.e., proliferation of T cell was induced) was found. Moreover, from the results of immunological analysis of sera of gingivitis and periodontitis patients, it has been clarified that the serum level of the degradation product and the autoantibody thereto have increased along with the progression of the symptoms.

The present inventors have also found that, on the lymphocyte cell surface of periodontitis patients, expression of RANKL, which is known as a ligand of cell surface receptor Receptor Activator of NFκB (RANK) which promotes differentiation of osteoclast progenitor cell into osteoclast, remarkably increases after stimulation with Keratin 6 or a degradation product thereof, and lymphoblast formation occurs, and that expression of RANKL mRNA is remarkably suppressed by anti Keratin 6 fragment antibody. Furthermore, when the rat was immunized with Keratin 6 or a degradation product thereof, RANKL-expressing T cells proliferate among the peripheral blood mononuclear cells, and remarkable alveolar bone resorption was observed. It has further been clarified that, in gingival fibroblasts stimulated with a Keratin 6 degradation product, MAPK signaling that promotes osteoclast differentiation by signal transduction of RANK/RANKL is activated, and expression of various cytokines/chemokines related to the migration of osteoclast progenitor cells/osteoclast differentiation/bone resorption/inflammation increases.

The above results reveal that alveolar bone destruction and initiation/aggravation of inflammation, which result from digestion of keratin in the gingival epithelial tissue by periodontal bacterial enzymes, followed by stimulation of the growth of T cells by keratin and a degradation product thereof transferred into the blood, which induces autoimmune response thereto, as well as induction of expression of RANKL in T cells by keratin and a degradation product thereof, and induction of differentiation of osteoclast progenitor cell into osteoclast by the activated T cells to promote bone resorption, are deeply involved in the onset and progression of periodontal diseases, as well as the onset of systemic complications. Therefore, it is possible to prevent the onset of a periodontal disease, suppress the progression thereof, and prevent the onset of systemic complications by suppressing the generation of keratin degradation products, rapidly removing the generated degradation products from the mouth cavity to prevent transfer thereof into the blood, preventing initial immunization and/or booster effect, suppressing differentiation of osteoclast via RANKL by activated T cells and production of autoantibody, and removing the autoantibody to the degradation product from the mouth cavity to prevent the gingival epithelial tissue from being attacked, thus suppressing inflammation.

The present inventors have conducted further studies based on these findings and completed the present invention.

Accordingly, the present invention provides the following.

[1] A peptide consisting of the amino acid sequence shown by any of SEQ ID NOs: 1-10.

[2] The peptide of the above-mentioned [1], which is a diagnostic marker of a periodontal disease.

[3] An antibody specifically recognizing the peptide of the above-mentioned [1].

[4] A diagnostic reagent for a periodontal disease, comprising the antibody of the above-mentioned [3].

[5] A test method for the diagnosis of a periodontal disease of a test animal, comprising measuring an amount of one or more peptides selected from the group of peptides consisting of amino acid sequences which are the same or substantially the same as respective amino acid sequences shown by SEQ ID NOs: 1-10, and/or one or more autoantibodies selected from the group consisting of autoantibodies to respective peptides of said group of peptides, in a biological sample obtained from the test animal.

[6] The method of the above-mentioned [5], wherein the biological sample is a body fluid.

[7] The method of the above-mentioned [6], wherein the body fluid is selected from the group consisting of blood, plasma, serum, interdental liquid, urine and saliva.

[8] The method of any of [5]-[7], comprising applying the biological sample to mass spectrometry.

[9] The method of any of [5]-[7], comprising using one or more antibodies selected from the group consisting of antibodies to respective peptides consisting of amino acid sequences which are the same or substantially the same as respective amino acid sequences shown by SEQ ID NOs: 1-10, and/or one or more peptides selected from the group of peptides consisting of amino acid sequences which are the same or substantially the same as respective amino acid sequences shown by SEQ ID NOs: 1-10.

[10] The method of the above-mentioned [5] or [9], comprising measuring the aforementioned peptides and/or the aforementioned autoantibodies according to a method selected from ELISA method, RIA method, nephelometry and SPR method.

[11] The method of any of [5]-[10], comprising collecting biological samples from patients in a chronological order, and measuring time course changes of an amount of one or more peptides selected from the group of peptides consisting of amino acid sequences which are the same or substantially the same as respective amino acid sequences shown by SEQ ID NOs: 1-10, and/or one or more autoantibodies selected from the group consisting of autoantibodies to respective peptides of said group of peptides in the samples.

[12] A method of evaluating a treatment effect in a patient with a periodontal disease, comprising measuring changes of an amount of one or more peptides selected from the group of peptides consisting of amino acid sequences which are the same or substantially the same as respective amino acid sequences shown by SEQ ID NOs: 1-10, and/or one or more autoantibodies selected from the group consisting of autoantibodies to respective peptides of said group of peptides, in biological samples obtained from said patient before and after the treatment.

[13] An inhibitor of an autoimmune response to keratin in gingival epithelium or a periodontal bacterial enzymatic degradation product thereof in a mammal having a periodontal bacterium in the oral cavity, comprising a substance having affinity to said keratin or a degradation product thereof and/or a substance having affinity to an autoantibody to said keratin or a degradation product thereof.

[14] The inhibitor of the above-mentioned [13], which is for the prophylaxis and/or treatment of a periodontal disease and/or a complication thereof.

[15] The inhibitor of the above-mentioned [13] or [14], wherein the aforementioned substance having affinity to keratin or a degradation product thereof is an antibody to said keratin or a degradation product thereof.

[16] The inhibitor of the above-mentioned [13] or [14], wherein the aforementioned substance having affinity to an autoantibody to keratin or a degradation product thereof is said keratin or a degradation product thereof or a peptide comprising all or a part of an amino acid sequence thereof.

[17] The inhibitor of any of the above-mentioned [13]-[16], wherein the keratin is Keratin 5, Keratin 6, Keratin 14 or Keratin 17.

[18] The inhibitor of any of the above-mentioned [13]-[17], wherein the aforementioned degradation product is one or more peptides selected from the group of peptides consisting of amino acid sequences which are the same or substantially the same as the respective amino acid sequences shown by SEQ ID NOs: 1-10.

[19] The inhibitor of any of the above-mentioned [13]-[18], which is combined with a periodontal bacterial enzyme inhibitor.

[20] The inhibitor of any of the above-mentioned [13]-[19], which is a composition for mouth cavity.

[21] A method of screening for a substance inhibiting an autoimmune response to keratin in gingival epithelium or a periodontal bacterial enzymatic degradation product thereof, in a mammal having a periodontal bacterium in the oral cavity, which method comprising (1) a step of contacting an autoantibody to said keratin or a degradation product thereof with a test substance, (2) a step of measuring their binding level, and (3) a step of selecting a test substance bound to said autoantibody as a candidate inhibitory substance of said autoimmune response.

[22] A RANKL expression inhibitor in a mammal having a periodontal bacterium in the oral cavity, comprising a substance having affinity to keratin in gingival epithelium or a periodontal bacterial enzymatic degradation product thereof.

[23] The inhibitor of the above-mentioned [22], which is for the prophylaxis and/or treatment of a periodontal disease and/or a complication thereof.

[24] The inhibitor of the above-mentioned [22] or [23], wherein the aforementioned substance having affinity to keratin or a degradation product thereof is an antibody to said keratin or a degradation product thereof.

[25] The inhibitor of any of the above-mentioned [22]-[24], wherein the keratin is Keratin 5, Keratin 6, Keratin 14 or Keratin 17.

[26] The inhibitor of any of the above-mentioned [22]-[25], wherein the aforementioned degradation product is one or more peptides selected from the group of peptides consisting of amino acid sequences which are the same or substantially the same as respective amino acid sequences shown by SEQ ID NOs: 1-10.

[27] A method of screening for an inhibitory substance of RANKL expression in a mammal having a periodontal bacterium in the oral cavity, comprising (1) a step of contacting keratin in gingival epithelium or a periodontal bacterial enzymatic degradation product thereof with a test substance, (2) a step of measuring their binding level, and (3) a step of selecting a test substance bound to said keratin or a degradation product thereof as a candidate inhibitory substance of RANKL expression.

[28] A method of screening for an inhibitory substance of RANKL expression in a mammal having a periodontal bacterium in the oral cavity, comprising (1) a step of contacting, in the presence and absence of a test substance, non-human mammal-derived T cell immunized with keratin in gingival epithelium or a periodontal bacterial enzymatic degradation product thereof with said keratin or a degradation product thereof, (2) a step of measuring one or more selected from the group consisting of
   a) a binding level of said keratin or a degradation product thereof to the T cell,
   b) a level of T cell proliferation, and
   c) an expression level of RANKL in the T cell, each of which in the presence and absence of the test substance, and (3) a step of selecting a test substance that decreased any of the above-mentioned a)-c) as a candidate inhibitory substance of RANKL expression.

[29] A method of producing a periodontal disease animal model, comprising immunizing a non-human mammal with keratin in gingival epithelium or a periodontal bacterial enzymatic degradation product thereof.

Furthermore, the present invention provides the following.

[30] A keratin degradation promoter comprising a periodontal bacterial enzyme.

[31] The promoter of the above-mentioned [30], which is applied to a nail, a hair or a skin.

[32] A method of detecting the activity of a periodontal bacterium, comprising contacting a subject bacterium, a secretion product thereof or a processed product thereof with keratin, and evaluating degradation of the keratin.

[33] A method of screening for a periodontal disease inhibitory or promoting substance, comprising contacting, in the presence and absence of a test substance, a periodontal bacterium, a secretion product thereof or a processed product thereof with keratin, and comparing the degradation of the keratin under both conditions.

Effect Of The Invention

By removing keratin or a degradation product by periodontal bacterial enzyme, which becomes an autoantigen, from the oral cavity, transfer of the keratin or a degradation product thereof into the blood is suppressed, and the production of autoantibody can be suppressed. In addition, the attack of the autoantibody on gingival epithelium can be prevented by removing the produced autoantibody from the oral cavity, whereby periodontal diseases can be treated and the onset of systemic complications associated with the periodontal disease can be prevented. Moreover, by inhibiting the activation of T cells (proliferation and increased expression of RANKL) by the keratin or a degradation product thereof, alveolar bone destruction by differentiation of osteoclast, and initiation and aggravation of periodontitis by induction of inflammatory cytokine can be suppressed and periodontal diseases can be prevented or treated.

In addition, since a periodontal disease can be judged rapidly, conveniently and accurately by detecting a keratin degradation product by periodontal bacterial enzyme, early detection and rapid cure of the disease can be enabled.

Moreover, a periodontal bacterial enzyme can be used, due to its keratin degradation action, for removal of stratum corneum, prevention of wavy hair, removal of unwanted hair, enhancement of skin permeability of medicaments, deformation or discoloration of nail such as ingrown toenail and the like, treatment of *Trichophyton* infections such as tinea unguium, and the like.

Furthermore, using keratin degradation as an index, identification of novel periodontal bacterium and screening for a therapeutic drug for a periodontal disease are enabled.

BRIEF DESCRIPTION OF THE DRAWINGS

FIG. 2 shows the results of on spot profiling of human Keratin 6(T1) and its Kgp reaction product (S1) (upper panel), and human Keratin 17(T2) and its RgpB reaction product (S2) (lower panel), wherein the vertical axis shows relative peak intensity and the horizontal axis shows m/z values.

FIG. 3 shows the identification results of (a) a Kgp degradation product of human Keratin 6 and (b) an RgpB degradation product of human Keratin 17.

FIG. 9A shows differentiation induction into polynuclear giant cells by stimulation of T cells obtained from periodontal disease patients and healthy subjects with FL or K6F, and suppression of the differentiation induction by the addition of RANKL inhibitor OPG-Fc. B shows the results of pit formation assay after stimulating T cells obtained from periodontal disease patients (upper panel) and healthy subjects (lower panel) with FL or K6F.

FIG. 15 shows time-course changes of the expression of MMP-2 and MMP-3(A), MCP-1(B), IL-8(C) and IL-6(D) in gingival fibroblasts stimulated with K6F or scramble peptide (Sc). RK6 or Rec-K6 shows recombinant Keratin 6.

FIG. 16 shows (A) time-course changes of the levels of phosphorylated p38 MAPK (top), IκB-α (middle) and phosphorylated p65 NFκB (lower) in the gingival fibroblasts stimulated with K6F or scramble peptide (Sc), and (B) time-course changes of the activation of various serine/threonine kinases in the gingival epithelial cells stimulated with K6F or scramble peptide (Sc).

Figure 1:
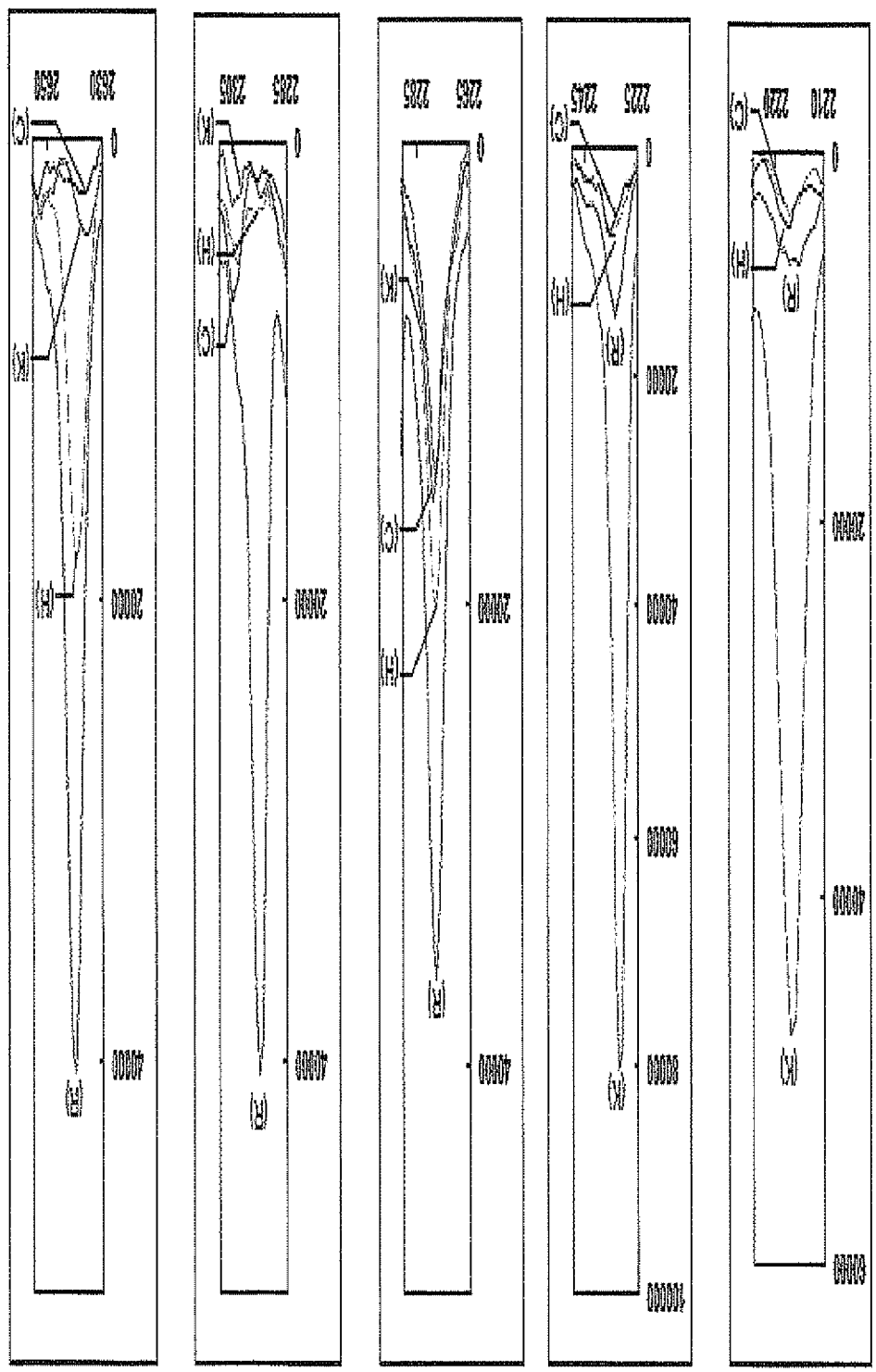
FIG. 1 shows the results of mass spectrometry of degradation products obtained when rat gingival epithelial cells are treated with 3 kinds of periodontal bacterial enzymes, wherein the vertical axis shows relative peak intensity and the horizontal axis shows m/z values. (K) Kgp treatment; (H)HRgpA treatment; (R) RgpB treatment; (C) control (non-treatment)

DESCRIPTION OF EMBODIMENTS (I) Keratin Degradation Products by Periodontal Bacterial Enzyme Present in Gingival Epithelium (the Peptide of the Present Invention)

The present invention provides a novel group of peptides that can become a biomarker and therapeutic target of periodontal diseases. All of such peptides (hereinafter sometimes to be referred to as "the peptide of the present invention") have keratin, which is present in gingival epithelial tissues, as a parental protein, and are produced by the degradation of said protein by periodontal bacterial enzymes.

Keratin (cytokeratin) is a generic term of proteins having a molecular weight about 40-68 kDa and constituting intermediate (diameter about 8-11 nm) filaments that form the cytoskeleton of epithelial cells. It is divided into approximately 20 to 30 kinds depending on the molecular weight and biochemical characteristics, and largely divided into type I having a small molecular weight (acidic keratin; Keratin 10-20) and type II having a high molecular weight (neutral/basic keratin; Keratin 1-9), and a heterodimer made of these two types in combination constitutes a reticular filament.

Keratin which is the parental protein of the peptide of the present invention is not particularly limited as long as it is a protein classified as keratin present in a gingival epithelial tissue and, for example, Keratin 1-20 etc., preferably Keratin 1, 2, 4, 5, 6, 8, 10, 11, 13, 14, 15, 16, 17, 18, 19 etc., more preferably Keratin 5, 6, 14 and 17, can be mentioned. These keratin proteins are known to have many subtypes, and any subtype is encompassed therein as long as it is present in a gingival epithelial tissue.

As the periodontal bacterial enzyme, gingipain produced by *P. gingivalis*, for example, Kgp, RgpB and HRgpA, can be preferably mentioned.

The peptide of the present invention is not particularly limited as long as it is a peptide fragment formed by partial digestion of any of the above-mentioned keratins by, for example, a periodontal bacterial enzyme such as gingipain (e.g., Kgp, RgpB, HRgpA) and the like, and to which an autoantibody is produced when it is transferred into the blood of a mammal infected with a periodontal bacterium. In consideration of the blood transferability, for example, it is a peptide having a molecular weight of not more than about 10,000, preferably not more than about 5000 and, in consideration of immunogenicity, for example, it is a peptide having a molecular weight of not less than about 500, preferably not less than about 1000. Such peptide can be easily identified by, for example, treating a purified keratin protein with one or more kinds of periodontal bacterial enzymes, preferably gingipain, and analyzing a keratin degradation product contained in the obtained enzyme reaction mixture by a method known per se, for example, blotchip (registered trade mark) technique of Protosera, a method using general two-dimensional gel electrophoresis and mass spectrometry in combination, LC-MS, LC-MS/MS and the like.

Preferable specific examples of the peptide of the present invention include, as Kgp degradation products of Keratin 6, a peptide consisting of the 360-378-position partial amino acid sequence (SEQ ID NO: 1) of human keratin 6B (registered in UniprotKB database under accession No. P04259; SEQ ID NO: 11) (peptide 1), a peptide consisting of the 260-271-position partial amino acid sequence thereof (SEQ ID NO: 4) (peptide 6), a peptide consisting of the 339-359-position partial amino acid sequence thereof (SEQ ID NO: 5) (peptide 7) and the like. Peptides 1, 6 and 7 also include, in human Keratin 6B paralogs (e.g., human Keratin 6A (UniprotKB/Swiss-prot 902538), human Keratin 6C (UniprotKB/Swiss-prot P48668), human Keratin 5 (UniprotKB/Swiss-prot P13647) etc.) and orthologs thereof (e.g., rat Keratin 6A (UniprotKB/Swiss-prot Q4FZU2), mouse Keratin 6A (UniprotKB/Swiss-prot P50446), mouse Keratin 6B (UniprotKB/Swiss-prot Q9Z331), rat Keratin 5 (UniprotKB/Swiss-prot Q6P6Q2), mouse Keratin 5 (UniprotKB/Swiss-prot Q922U2), chimpanzee Keratin 5 (UniprotKB/Swiss-prot A5A6M8), bovine Keratin 5 (UniprotKB/Swiss-prot Q5XQN5) etc.), peptides consisting of partial amino acid sequences each corresponding thereto (see Tables 3-1-3-3 and Table 4), naturally-occurring variants or polymorphisms thereof (substitution, deletion, insertion of 1-2 amino acids; e.g., polymorphism wherein, in peptide 1, the 365-position Ile is substituted by Val (registered in NCBI SNP database as rs437014)).

Since the cleavage site by periodontal bacterial enzymes may not always be strict, peptides 1, 6 and 7 also encompass those wherein the N-terminal and/or the C-terminal of peptides 1, 6 and 7 is/are displaced by about 1-3 residues from the above-mentioned partial amino acid sequences toward the N-terminal side or C-terminal side of the parental protein.

Other preferable specific examples of the peptide of the present invention include, as Kgp degradation products of Keratin 5, a peptide consisting of the 365-383-position partial amino acid sequence (SEQ ID NO: 15) of human keratin 5 (registered in UniprotKB database under accession No. P13647; SEQ ID NO: 12) (peptide 2), a peptide consisting of the 265-276-position partial amino acid sequence thereof, a peptide consisting of the 344-364-position partial amino acid sequence thereof and the like. These peptides also include, in human Keratin 5 paralogs (e.g., human Keratin 6A (UniprotKB/Swiss-prot P02538), human keratin 6B (UniprotKB/Swiss-prot P04259), human Keratin 6C (UniprotKB/Swiss-prot P48668) etc.) and orthologs thereof (e.g., rat Keratin 5 (UniprotKB/Swiss-prot Q6P6Q2), mouse Keratin 5 (UniprotKB/Swiss-prot Q922U2), chimpanzee Keratin 5 (UniprotKB/Swiss-prot A5A6M8), bovine Keratin 5 (UniprotKB/Swiss-prot Q5XQN5), rat Keratin 6A (UniprotKB/Swiss-prot Q4FZU2), mouse Keratin 6A (UniprotKB/Swiss-prot P50446), mouse Keratin 6B (UniprotKB/Swiss-prot Q9Z331) etc.), peptides consisting of partial amino acid sequences each corresponding thereto (see Tables 3-1-3-3 and Table 4), naturally-occurring variants or polymorphisms thereof (substitution, deletion, insertion of 1-2 amino acids; e.g., polymorphism wherein, in human Keratin 5, the 352-position Arg is substituted by Ser (Br. J. Dermatol. 155:313-317 (2006)). Since Keratin 5 is a paralog of Keratin 6, peptide 2 is encompassed in "peptide 1" in a wide sense in the present invention. Similarly, a peptide consisting of the 265-276-position partial amino acid sequence of Keratin 5, and a peptide consisting of the 344-364-position partial amino acid sequence are encompassed in peptides 6 and 7 in a wide sense.

Since the cleavage site by periodontal bacterial enzymes may not always be strict, the peptides also encompass those wherein the N-terminal and/or the C-terminal of peptide is/are displaced by about 1-3 residues from the above-mentioned partial amino acid sequences toward the N-terminal side or C-terminal side of the parental protein. Furthermore, those with possible amino acid modification such as acetylation of N-terminal, amidation of C-terminal, pyroglutamylation of N-terminal glutamic acid, phosphorylation of Ser, The, Tyr, Asp or H is, hydroxylation of Asn, Asp, Pro or Lys, methylation of Lys or Arg, sulfation of Tyr, oxidization of Met and the like are also encompassed.

Other preferable specific examples of the peptide of the present invention include, as the Rgp degradation product of Keratin 14, peptides consisting of the 450-469-position partial amino acid sequence (SEQ ID NO: 2) of human keratin 14 (registered in UniprotKB database under accession No. P02533; SEQ ID NO: 13) (peptides 3 and 4), a peptide consisting of the 7-30-position partial amino acid sequence thereof, a peptide consisting of the 202-2,1-position partial amino acid sequence thereof, a peptide consisting of the 289-299-position partial amino acid sequence thereof, a peptide consisting of the 316-335-position partial amino acid sequence thereof and the like. These peptides also include, in human Keratin 14 paralogs (e.g., human Keratin 17 (UniprotKB/Swiss-prot Q04695), human Keratin 16 (UniprotKB/Swiss-prot P08779) etc.) and orthologs thereof (e.g., rat Keratin 14 (UniprotKB/Swiss-prot Q6IFV1), mouse Keratin 14 (Q61781), rat Keratin 17 (Q6IFU8), mouse Keratin 17 (Q9QWL7), chimpanzee Keratin 17 (A5A6M0), bovine Keratin 17 (A1L595) etc.), peptides consisting of partial amino acid sequences each corresponding thereto (see Table 5 and Table 6), naturally-occurring variants or polymorphisms thereof (substitution, deletion, insertion of 1-2 amino acids; e.g., polymorphism wherein, in human Keratin 14, the 211-position Arg is substituted by Pro (Hum. Mutat. 27:719-720 (2006))). Since Keratin 14 is a paralog of Keratin 17, a peptide consisting of the 7-30-position partial amino acid sequence of Keratin 14, a peptide consisting of the 202-211-position partial amino acid sequence of Keratin 14, a peptide consisting of 289-299-position partial amino acid sequence of Keratin 14 and a peptide consisting of the 316-335-position partial amino acid sequence of Keratin 14 are encompassed in peptides 8, 9, 11 and 12 in a wide sense.

Since the cleavage site by periodontal bacterial enzymes may not always be strict, the peptides also encompass those wherein the N-terminal and/or the C-terminal of peptide is/are displaced by about 1-3 residues from the above-mentioned partial amino acid sequences toward the N-terminal side or C-terminal side of the parental protein. Furthermore, those with possible amino acid modification such as acetylation of N-terminal, amidation of C-terminal, pyroglutamylation of N-terminal glutamic acid, phosphorylation of Ser, The, Tyr, Asp or His, hydroxylation of Asn, Asp, Pro or Lys, methylation of Lys or Arg, sulfation of Tyr, oxidization of Met and the like are also encompassed.

Other preferable specific examples of the peptide of the present invention include, as the Rgp degradation product of Keratin 17, a peptide consisting of the 410-432-position partial amino acid sequence (SEQ ID NO: 3) of human keratin 17 (registered in UniprotKB database under accession No. Q04695; SEQ ID NO: 14) (peptide 5), a peptide consisting of the 171-180-position partial amino acid sequence thereof (SEQ ID NO: 6) (peptide 8), a peptide consisting of the 258-268-position partial amino acid sequence thereof (SEQ ID NO: 7) (peptide 9), a peptide consisting of the 410-424-position partial amino acid sequence thereof (SEQ ID NO: 8) (peptide 10), a peptide consisting of the 7-26-position partial amino acid sequence thereof (SEQ ID NO: 9) (peptide 11), a peptide consisting of the 285-304-position partial amino acid sequence thereof (SEQ ID NO: 10) (peptide 12) and the like. Peptides 5 and 8-12 also include, in human Keratin 17 paralogs (e.g., human Keratin 14 (UniprotKB/Swiss-prot Q04695), human Keratin 16 (UniprotKB/Swiss-prot P08779) etc.) and orthologs thereof (e.g., rat Keratin 17 (Q61FU8), mouse Keratin 17 (Q9QWL7), chimpanzee Keratin 17 (A5A6M0), bovine Keratin 17 (A1L595), rat Keratin 14 (UniprotKB/Swiss-prot Q61FV1), mouse Keratin 14 (Q61781) etc.), peptides consisting of partial amino acid sequences each corresponding thereto (see Table 5 and Table 6), naturally-occurring variants or polymorphisms thereof (substitution, deletion, insertion of 1-2 amino acids).

Since the cleavage site by periodontal bacterial enzymes may not always be strict, the peptides 5 and 8-12 also encompass those wherein the N-terminal and/or the C-terminal of peptide is/are displaced by about 1-3 residues from the above-mentioned partial amino acid sequences toward the N-terminal side or C-terminal side of the parental protein. Furthermore, those with possible amino acid modification such as acetylation of N-terminal, amidation of C-terminal, pyroglutamylation of N-terminal glutamic acid, phosphorylation of Ser, The, Tyr, Asp or His, hydroxylation of Asn, Asp, Pro or Lys, methylation of Lys or Arg, sulfation of Tyr, oxidization of Met and the like are also encompassed.

(II) Substance Having Affinity to Keratin or the Peptide of the Present Invention/Substance Having Affinity to Autoantibody to Keratin or the Peptide As mentioned above, a periodontal bacterial enzyme digests keratin in a gingival epithelial tissue, and the produced peptide of the present invention or keratin itself enters into the blood to stimulate T cell proliferation and RANKL expression and induce an autoimmune response to the peptide and differentiation of osteoclast, which is deeply involved in the onset and progression of periodontal diseases, as well as the onset of systemic complications. Therefore, using a substance having affinity to keratin or the peptide of the present invention, or a substance having affinity to an autoantibody to keratin or the peptide (hereinafter to be also referred to as "the autoantibody of the present invention"), keratin or the peptide and/or the autoantibody are/is trapped and removed from the mouth cavity to suppress an autoimmune response wherein keratin or the peptide is an antigen, whereby the onset of periodontal diseases and systemic complications can be prevented or their progression can be suppressed.

Examples of the substance having affinity to keratin or the peptide of the present invention include an antibody to keratin or the peptide (hereinafter to be also referred to as "therapeutic antibody"). Examples of the substance having affinity to the autoantibody of the present invention include a peptide containing the amino acid sequence of the epitope recognized by the autoantibody (hereinafter to be also referred to as "therapeutic peptide"), namely, a peptide containing all or a part of the amino acid sequence of the peptide of the present invention.

(II-1) Therapeutic Peptide

The therapeutic peptide of the present invention may have any of a carboxyl group, carboxylate, amide or ester at the C-terminal. When the peptide has a carboxyl group (or carboxylate) at a position other than the C-terminal, the carboxyl group may be amidated or esterified. Furthermore, in the peptide, an amino group of the amino acid residue at the N terminal may be substituted by, for example, a formyl group, an acetyl group and the like, the glutamine residue at the N terminal may be pyroglutamylated, or a substituent on the side chain of an amino acid in a molecule (for example, —OH, —SH, an amino group, an imidazole group, an indole group, a guanidino group and the like) may be substituted by other substituent (e.g., a formyl group, an acetyl group and the like).

In addition, the therapeutic peptide of the present invention may be a salt with an acid or base, and an acid addition salt is particularly preferable. As such salt, for example, salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like can be used As the peptide containing the amino acid sequence of the peptide of the present invention, the peptide itself or a peptide having an amino acid sequence wherein one or more amino acids are added to the N-terminal and/or the C-terminal of the amino acid sequence, which retains a binding ability to the autoantibody of the present invention, can be mentioned. Preferable examples of the latter include, but are not limited to, the full-length of keratin, which is the parental protein of the peptide of the present invention, and a fragment thereof, which contains the amino acid sequence of the peptide.

The peptide having the amino acid sequence of the peptide of the present invention can be chemically synthesized based on the above-mentioned information of the amino acid sequence of the peptide of the present invention, or can also be obtained by digesting keratin, which is the parental protein of the peptide of the present invention, with a suitable protease (e.g., periodontal bacterial enzyme such as gingipain and the like, and the like) as necessary, and isolating the object peptide fragment from the obtained enzymatic degradation product by a method known per se. A keratin protein can be isolated from a cell or tissue producing same (e.g., gingival epithelium) by a protein separation technique known per se, or recombinantly produced by isolating cDNA based on the gene sequence information registered in a known database.

On the other hand, the peptide containing a part of the amino acid sequence of the peptide of the present invention is not particularly limited as long as it is recognized by the autoantibody of the present invention and, for example, a peptide containing not less than 3, preferably not less than 4, more preferably not less than 5, further preferably not less than 6, continuous amino acid residues in the amino acid sequence of the peptide of the present invention can be mentioned. Examples of the peptide containing a part of the amino acid sequence of the peptide of the present invention include a peptide containing not more than 20, preferably not more than 18, more preferably not more than 15, further preferably not more than 12, continuous amino acid residues in the amino acid sequence of the peptide of the present invention.

A peptide containing a part of the amino acid sequence of the peptide of the present invention is preferably chemically synthesized based on the above-mentioned information of the amino acid sequence of the peptide of the present invention. The synthesis method of the peptide may be any of the solid phase synthesis process and the liquid phase synthesis process. That is, the object peptide can be produced by condensing a partial peptide or amino acid capable of constituting the peptide and the remaining portion, and eliminating the protecting group when the resultant product has a protecting group. As the known condensation method and elimination of the protecting group, the methods described in the following 1) or 2) and the like can be mentioned.

1) M. Bodanszky and M. A. Ondetti, Peptide Synthesis, Interscience Publishers, New York (1966)

2) Schroeder and Luebke, The Peptide, Academic Press, New York (1965)

After the reaction, the peptide can be purified and isolated by a general purification method, such as solvent extraction, distillation, column chromatography, liquid chromatography, recrystallization and the like in combination. When the peptide obtained by the above-mentioned method is in a free form, it can be converted to a suitable salt by a known method. Conversely, when it is obtained as a salt, it can be converted to a free form or other salt by a known method.

As mentioned above, in the present invention, a degradation product of keratin, which is present in the gingival epithelium, by periodontal bacterial enzyme is preferably a degradation product of Keratin 5, Keratin 6, Keratin 14 or Keratin 17 or an analog thereof (for example, paralog) by the enzyme (e.g., gingipain), more preferably, peptides consisting of amino acid sequences which are the same or substantially the same as the respective amino acid sequences shown by SEQ ID NOs: 1-10. As used herein, the "substantially the same amino acid sequence" includes an ortholog of a parental protein of the peptide shown by each Sequence No. in other mammal, a protein which is a paralog in human or other mammal, or an amino acid sequence of the part corresponding to the amino acid sequence shown by the Sequence No. in a naturally-occurring allele variant or polymorphism thereof, the amino acid sequence wherein the N-terminal and/or the C-terminal are/is displaced by about 1-3 amino acids toward the N-terminal side or C-terminal side of the parental protein (e.g., amino acid sequence of Kgp degradation product of human Keratin 5, which is shown by SEQ ID NO: 15, is substantially the same as the amino acid sequence (SEQ ID NO: 1) of Kgp degradation product of human Keratin 6B (paralog)). Therefore, the therapeutic peptide of the present invention is preferably a peptide recognized and bound by an autoantibody to a degradation product of Keratin 5, Keratin 6, Keratin 14 or Keratin 17 or an analog thereof (for example, paralog) by the enzyme (e.g., gingipai), more preferably, a peptide recognized and bound by an autoantibody to a peptide consisting of an amino acid sequence which is the same or substantially the same as each amino acid sequence shown by SEQ ID NO: 1-10. That is, the therapeutic peptide of the present invention is preferably a peptide containing all or a part of the amino acid sequence of a degradation product of Keratin 5, Keratin 6, Keratin 14 or Keratin 17 or an analog thereof (for example, paralog) by the enzyme (e.g., gingipain), more preferably, a peptide containing all or a part of an amino acid sequence which is the same or substantially the same as each amino acid sequence shown by SEQ ID NOs: 1-10.

(II-2) Therapeutic Antibody

The therapeutic antibody of the present invention is not particularly limited as long as it specifically recognizes keratin or the peptide of the present invention of the above-mentioned (I), and may be a complete antibody molecule or, for example, a fragment such as Fab, Fab', F(ab')2 and the like, a conjugate molecule produced by genetic engineering such as scFv, scFv-Fc, minibody, diabody and the like, or a derivative thereof which is modified by a molecule having a protein stabilizing action such as polyethylene glycol (PEG) and the like, and the like, and the like.

When the antibody of the present invention is a monoclonal antibody, it can be prepared, for example, by the following method.

Keratin or the peptide of the present invention or a fragment thereof is prepared by any method described in the above-mentioned (II-1). Insolubilized peptide may be directly immunized as long as it has immunogenicity. When a low-molecular-weight antigen is used, such antigen peptide can be generally immunized as a complex conjugated or adsorbed to a suitable carrier, since it is a hapten molecule with low immunogenicity. As a carrier, a natural or synthetic polymer can be used. As the natural polymer, serum albumin of a mammal such as bovine, rabbit, human and the like, silo globulin of a mammal such as bovine, rabbit and the like, ovalbumin of, for example, chicken, hemoglobin of a mammal such as bovine, rabbit, human, sheep and the like, keyhole limpet hemocyanin (KLH) and the like are used. Examples of the synthetic polymer include various latexes and the like of polymer substance or copolymer and the like of polyamino acids, polystyrenes, polyacryls, polyvinyls, polypropylenes and the like can be mentioned. The mixing ratio of the carrier and hapten may be any as long as an antibody to an antigen conjugated or adsorbed to a carrier is efficiently produced, and any of the carriers and haptens may be conjugated or adsorbed. Generally, the above-mentioned natural or synthetic polymer carriers normally used for the production of an antibody to hapten can be conjugated or adsorbed at a weight ratio of 0.1-100 to hapten as 1.

For coupling of hapten and a carrier protein, various condensing agents can be used. For example, diazonium compounds such as bisdiazotized benzidine that crosslinks tyrosine, histidine or tryptophan and the like, dialdehyde compounds such as glutaraldehyde that crosslinks amino groups to each other and the like, diisocyanate compounds such as toluene-2,4-diisocyanate and the like, dimaleimide compounds such as N,N'-o-phenylenedimaleimide that crosslinks thiol groups to each other and the like, a maleimide active ester compound that crosslinks amino group and thiol group, a carbodiimide compound that crosslinks amino group and carboxyl group and the like are conveniently used. In addition, when amino groups are crosslinked to each other, it is possible to react one of the amino groups with an active ester reagent (e.g., SPDP and the like) having a dithiopyridyl group and reduce same to introduce a thiol group, introduce a maleimide group into the other amino group by a maleimide active ester reagent, and react them. It is also possible to add a cysteine residue to the N-terminal or C-terminal of hapten (peptide), introduce a maleimide group into an amino group of a carrier protein by a maleimide active ester reagent and react them.

An antigen peptide is administered to a warm-blooded animal by, for example, an administration method such as intraperitoneal injection, intravenous injection, subcutaneous injection, intradermal injection and the like, to a site capable of producing an antibody, by itself or together with a carrier or a diluent. To enhance antibody producibility during administration, complete Freund's adjuvant or incomplete Freund's adjuvant may be administered. Administration is generally performed 2 to 10 times in total once every 1 to 6 weeks. Examples of the warm-blooded animal include rabbit, goat, bovine, chicken, mouse, rat, hamster, sheep, swine, horse, camel, cat, dog, monkey, chimpanzee and the like, and mouse, rat, rabbit and the like are generally used preferably for producing a monoclonal antibody.

For production of a monoclonal antibody producing cell, an animal confirmed to have a serum antibody titer is selected from warm-blooded animals, for example, mouse, immunized with an antigen, spleen or lymph node is isolated 2-5 days after the final immunization, and an antibody producing cell contained therein is fused with myeloma cells, whereby a monoclonal antibody producing hybridoma can be prepared. The antibody titer in the antiserum is measured by, for example, reacting a solid-phase-immobilized antigen peptide with antiserum, and detecting an antigen peptide specific antibody bound to the solid phase using an antibody to an antibody of an immunized animal species labeled with a radioactive substance or enzyme. Fusion operation can be performed by a known method, for example, the method of Köhler and Milstein [Nature, vol. 256, page 495 (1975)]. Examples of the fusion promoter include polyethylene glycol (PEG), Sendai virus and the like, and PEG is preferably used.

Examples of the myeloma cell include NS-1, P3U1, SP2/0 and the like, with preference given to P3U1. A preferable ratio of the number of antibody producing cells (spleen cell) and the number of myeloma cells is about 1:1-20:1, and cell fusion is efficiently performed by adding PEG (preferably, PEG1000-PEG6000) at a concentration of about 10-80%, and incubating the mixture at about 20-40° C., preferably about 30-37° C. for about 1-10 min.

Fused cell (hybridoma) can be selected by a method known per se or a method analogous thereto. Generally, it can be selected in an animal cell medium added with HAT (hypoxanthine, aminopterine, thymidine) and the like. As a medium for selection and breeding, any medium can be used as long as hybridoma can grow. For example, RPMI1640 medium containing 1-20%, preferably 10-20%, of fetal bovine serum, GIT medium containing 1-10% of fetal bovine serum (Wako Pure Chemical Industries, Ltd.) or serum-free medium for hybridoma culture (SFM-101, Nissui Pharmaceutical Co., Ltd.) and the like can be used. The culture temperature is generally 20-40° C., preferably about 37° C. The culture time is generally 5 days-3 weeks, preferably 1 week ~2 weeks. The culture can be generally performed in 5% carbonic acid gas.

Various methods can be used for screening for a monoclonal antibody producing hybridoma. For example, a method including adding a hybridoma culture supernatant to a solid phase (e.g., microplate) to which antigen peptide is directly adsorbed or adsorbed together with a carrier, then adding an anti-immunoglobulin antibody (when antibody producing cell used for cell fusion is mouse, anti-mouse immunoglobulin antibody is used) labeled with a radioactive substance, an enzyme and the like or protein A, and detecting a monoclonal antibody bound to the solid phase, a method including adding a hybridoma culture supernatant to a solid phase to which anti-immunoglobulin antibody or protein A is adsorbed, adding an antigen peptide labeled with a radioactive substance, an enzyme and the like, and the like, and detecting a monoclonal antibody bound to the solid phase and the like can be mentioned.

The monoclonal antibody can be separated and purified by, like general separation and purification of polyclonal antibody, a separation and purification method of immunoglobulin [e.g., salting out method, alcohol precipitation method, isoelectric point precipitation method, electrophoresis, adsorption and desorption method using an ion exchanger (e.g., DEAE), ultracentrifugation method, gel filtration method, or a specific purification method including obtaining an antibody alone by an active adsorbent such as antigen conjugated solid phase, protein A, protein G and the like, and dissociating the binding to give an antibody].

When an antibody medicament is administered to human as a subject, the antibody is generally desirably an antibody with a reduced risk of antigenicity when administered to human, specifically, complete human antibody, humanized antibody, non-human-human chimera antibody and the like. When desired, such humanized antibody can also be used in the present invention. A humanized antibody and a chimera antibody can be produced by genetic engineering by a method known per se. A complete human antibody can also be produced from human-human (or human-mouse) hybridoma; however, it is desirably produced using a human antibody producing animal (e.g., mouse, bovine) or phage display method.

In the autoimmune response inhibitor of the present invention, however, since the therapeutic antibody is bound to the orally-present peptide of the present invention, and immediately removed extracorporeally after trapping same, the probability of an adverse influence due to the production of a human antibody to the antibody is low even with an antibody derived from a non-human animal. Therefore, a polyclonal antibody that can be produced in a large amount from a non-human warm-blooded animal can be used even without using a humanized monoclonal antibody with a high production cost.

The polyclonal antibody of the present invention can be produced by a method known per se or a method analogous thereto. For example, a warm-blooded animal is immunized with a complex of keratin, the peptide of the present invention of the above-mentioned (I) or a fragment thereof and a carrier protein in the same manner as in the above-mentioned production method of a monoclonal antibody, obtaining a material containing an antibody to the antigen from the immunized animal, and separating and purifying the antibody.

As for a complex of hapten and a carrier protein used for immunizing a warm-blooded animal, the kind of the carrier protein and the mixing ratio of a carrier and hapten may be any as long as the antibody to hapten used for immunization by crosslinking with a carrier is efficiently produced, and any of the carriers and haptens may be crosslinked at any ratio. For example, a method including conjugating bovine serum albumin, bovine thyroglobulin, KLH and the like at a weight ratio of about 0.1-20, preferably about 1-5, to hapten as 1 is used.

For coupling of hapten and a carrier protein, various condensing agents can be used, and active ester reagents containing glutaraldehyde, carbodiimide, maleimide active ester, thiol group or dithiopyridyl group, and the like are used.

A condensation product is administered to a warm-blooded animal at a site capable of producing an antibody by itself or together with a carrier and a diluent. To enhance antibody productivity for administration, complete Freund's adjuvant or incomplete Freund's adjuvant may be administered. The administration is generally performed once every about 2-6 weeks and about 3-10 times in total.

A polyclonal antibody can be collected from the blood, ascites, breast milk, egg and the like of a warm-blooded animal immunized by the above-mentioned method.

The polyclonal antibody titer in an antiserum can be measured in the same manner as in the above-mentioned measurement of the antibody titer in a serum. The polyclonal antibody can be separated and purified according to a separation and purification method of immunoglobulin in the same manner as in the above-mentioned separation and purification of monoclonal antibody.

As mentioned above, in the present invention, the degradation product of keratin, which is present in the gingival epithelium, by periodontal bacterial enzyme is preferably a degradation product of Keratin 5, Keratin 6, Keratin 14 or Keratin 17 or an analog thereof (for example, paralog) by the enzyme (e.g., gingipain), more preferably, a peptide consisting of an amino acid sequence which is the same or substantially the same as each amino acid sequence shown by SEQ ID NOs: 1-10. The "substantially the same amino acid sequence" is as defined for the above-mentioned (II-1). Therefore, the therapeutic antibody of the present invention is preferably an antibody that specifically recognizes and binds to a degradation product of Keratin 5, Keratin 6, Keratin 14 or Keratin 17 or an analog thereof (for example, paralog) by the enzyme (e.g., gingipain), more preferably, a peptide that specifically recognizes and binds to a peptide consisting of an amino acid sequence which is the same or substantially the same as each amino acid sequence shown by SEQ ID NOs: 1-10.

(II-3) Other Substance Having Affinity to Keratin or the Peptide of the Present Invention/Other Substance Having Affinity to Autoantibody to Keratin or the Peptide Examples of other substance having affinity to keratin or the peptide of the present invention include aptamer to keratin or the peptide and the like, and examples of other substance having affinity to the autoantibody of the present invention include a secondary antibody and an aptamer to the antibody, and the like. Aptamer to keratin or the peptide of the present invention/aptamer to the autoantibody of the present invention can be obtained by a SELEX technique known per se. A secondary antibody to the autoantibody of the present invention can be obtained according to the method described in the above-mentioned (II-2) and using the autoantibody or a fragment thereof (e.g., F(ab')2, Fab) as an immunogen. The autoantibody of the present invention to be subjected to SELEX method and immunization of animal can be isolated from interdental liquid, serum, plasma and the like of periodontal disease patients by utilizing the affinity to the peptide of the present invention. The desired fragment can be obtained by digesting the obtained autoantibody with pepsin or papain.

(III) Preparation of Autoimmune Response Inhibitor

Substance having affinity to keratin or the peptide of the present invention and/or substance having affinity to autoantibody of the present invention obtained as mentioned above can be formulated into an autoimmune response inhibitor by itself alone or as a suitable composition. As the composition, one containing a substance having affinity to keratin or the peptide of the present invention and/or a substance having affinity to the autoantibody of the present invention, and a pharmacologically acceptable additive can be mentioned. Preferably, the composition is a composition suitable for intraoral administration (composition for mouth cavity). The composition for mouth cavity is combined with various additives according to the form thereof, and can be provided as toothpaste, liquid dentifrice, mouthwash, mouth cavity gel and the like.

The amount of the substance having affinity to keratin or the peptide of the present invention and a substance having affinity to the autoantibody of the present invention to be blended in an autoimmune response inhibitor of the present invention is not particularly limited as long as it is sufficient for adsorbing and removing orally present keratin, the peptide of the present invention and the autoantibody of the present invention. For example, it can be appropriately selected from the range of 50-0.01 wt %, preferably 5-0.1 wt %, of the whole composition. One kind of a substance having affinity to keratin or the peptide of the present invention or a substance having affinity to the autoantibody of the present invention may be used or two or more kinds thereof may be used in combination. For example, the presence or absence of keratin or the peptide of the present invention and/or the autoantibody of the present invention in interdental liquid is preferably tested by the below-mentioned test method for the diagnosis of periodontal disease, and one or more kinds of substances selected from the substances having affinity to keratin or peptide and/or autoantibody confirmed to be present are combined.

Examples of the additive to be used for the composition for mouth cavity include antimicrobial agent, surfactant, abrasive, wetting agent, monovalent alcohol, binder, flavor, sweetening agent, pH adjuster, preservative, dye and the like. Each of them can be appropriately combined as long as the effect of the present invention is not impaired.

Examples of the antimicrobial agent include quaternary ammonium salt, bisbiguanide, phenol, and non-cationic antimicrobial agent. Examples of the quaternary ammonium salt include cetylpyridinium chloride, benzethonium chloride, distearyldimethylammonium chloride, stearyldimethylbenzylammonium chloride, stearyltrimethylammonium chloride, cetyltrimethylammonium chloride, lauryltrimethylammonium chloride, laurylpyridinium chloride and the like. Examples of the bisbiguanide antimicrobial agent include bisbiguanide hexanes, bisbiguanide propylethers, bisbiguanide xylenes, bisbiguanide decanes, bisbiguanide dodecanes, and a chemically acceptable salt thereof and the like. Examples of the bisbiguanide hexanes include chlorhexidine salts such as chlorhexidine gluconate, chlorhexidine hydrochloride and the like. Examples of the phenol antimicrobial agent include isopropylmethylphenol and hinokitiol. Examples of the non-cationic antimicrobial agent include triclosan.

As the surfactant, nonionic, cationic or amphoteric surfactants can be used alone or two or more kinds thereof may be combined. Examples of the nonionic surfactant include sugar fatty acid esters such as sucrose fatty acid ester, maltose fatty acid ester and the like, sugar alcohol fatty acid esters such as multitol fatty acid ester and the like, sorbitan fatty acid esters such as monolauric acid sorbitan and the like, polyoxyethylene sorbitan fatty acid esters such as polyoxyethylene sorbitan monolaurate, polyoxyethylene sorbitan monostearate and the like, fatty acid alkanolamides such as lauric acid diethanolamide, polyoxyethylene alkyl ethers such as polyoxyethylene stearyl ether, polyoxyethylene oleyl ether and the like, polyethylene glycol fatty acid esters such as monooleic acid polyethylene glycol, monolauric acid polyethylene glycol and the like, polyglycerol fatty acid ester, polyoxyethylene glycerol fatty acid ester, polyoxyethylene fatty acid ester, alkylglucosides, polyoxyethylene hydrogenated castor oil, glycerol fatty acid ester, polyoxyethylene propylene block copolymer and the like. Examples of the amphoteric surfactant include amino acid type, alkylbetaine type, alkylamidebetaine type, sulfobetaine type, imidazoline type and the like, preferably 2-alkyl-N-carboxymethyl-N-hydroxyethylimidazolinium betaine, palm oil fatty acid amidepropylbetaine and the like.

As the abrasive, calcium carbonate, calcium phosphate, dibasic calcium phosphate, pyrrocalcium phosphate, insoluble sodium metaphosphate, titanium oxide, amorphous silica, crystalline silica, aluminosilicate, aluminum oxide, aluminum hydroxide, resin and the like may be used alone or two or more kinds thereof may be used in combination.

Examples of the wetting agent include polyvalent alcohols such as glycerol, sorbitol, polyethylene glycol, propylene glycol, ethylene glycol, hexylene glycol, 1,3-butylene glycol, polypropylene glycol, xylitol, maltitol, lactitol and the like. These may be used alone or two or more kinds thereof may be used in combination.

Examples of the monovalent alcohol include ethanol, propyl alcohol, isopropyl alcohol and the like, and ethanol is particularly preferable. These monovalent alcohols may be used alone or two or more kinds thereof may be used in combination.

Examples of the binder include cellulose derivatives such as carageenan, carboxymethylcellulose and the like, alkali metal alginates such as sodium alginate and the like, gums such as xanthan gum, gum tragacanth, gum arabic and the like, synthetic binders such as polyvinyl alcohol, sodium polyacrylate and the like, inorganic binders such as silica gel, aluminum silica gel, veegum and the liker, and the like.

As the flavor, anethole, menthol, peppermint oil, spearmint oil, lemon oil, orange oil, sage oil, rosemary oil, cinnamon oil, *perilla* oil, wintergreen oil, clove oil, eucalyptus oil, pimento oil, carvon, cinnamic aldehyde, cineole, menton, limonene, methyl salicylate and the like can be used alone or two or more kinds thereof may be used in combination as long as the effect of the present invention is not impaired.

Examples of the sweetening agent include palatinit, saccharin sodium, acesulfame potassium, stevioside, neohesperidyl dihydrochalcone, glycyrrhizin, perillartine, thaumatin, aspartylphenylalanyl methyl ester, p-methoxy cinnamic aldehyde and the like. These may be used alone or two or more kinds thereof may be used in combination.

Examples of the pH adjuster include citric acid, phosphoric acid, malic acid, pyrrophosphoric acid, lactic acid, tartaric acid, glycerophosphoric acid, acetic acid, nitric acid, a chemically acceptable salt or sodium hydroxide thereof, and the like. These may be used alone or two or more kinds thereof may be used in combination such that the composition has a pH of 5-9.

Moreover, the composition for mouth cavity of the present invention can contain vitamin Es such as dl-α-tocopherol acetate, tocopherol succinate, tocopherol nicotinate and the like, enzymes such as dextranase, amylase, protease, mutanase, lysozyme, lytic enzyme and the like, anti-plasmin agents such as tranexamic acid, epsilon aminocaproic acid, aluminum chlorhydroxylallantoin, dihydrocholesterol, glycyrrhizin salts, glycyrrhetinic acid, glycerolphosphate, chlorophyll, sodium chloride, callopeptide, water-soluble inorganic phosphate compound, fluorides such as sodium fluoride, potassium fluoride, ammonium fluoride, calcium fluoride, copper fluoride, zinc fluoride, lithium fluoride, cesium fluoride, zirconium fluoride, tin fluoride, hydrofluoric acid, sodium monofluorophosphate, potassium monofluorophosphate, sodium titanium fluoride, potassium titanium fluoride, hexylamine hydrofluoride, laurylamine hydrofluoride, glycine hydrofluoride, alanine hydrofluoride, fluorosilane, diammine silver fluoride and the like. These may be used alone or two or more kinds thereof may be used in combination. The composition for mouth cavity of the present invention can be produced by mixing these components and according to a generally method.

Therefore, to enhance oral mucosa retentivity, natural polymers such as gelatin, collagen, konjak mannan, pullulan, chitosan, starch and the like, synthetic polymers such as polyethylene glycol, carboxyvinyl polymer and the like, polysaccharides such as dextran, polyacryldextran and the like, lecithins such as soybean lecithin, egg-yolk lecithin and the like, polylactic acid, polyglycolic acid, albumin, cyclodextrin and the like. These may be used alone or two or more kinds thereof may be used in combination.

The substance having affinity to keratin or the peptide of the present invention, and the substance having affinity to the autoantibody of the present invention may be combined in a free state in the composition for mouth cavity. In another preferable embodiment, for example, it can also be combined by solid-phase-immobilization on an insoluble carrier such as microbeads.

The composition for mouth cavity containing a substance having affinity to keratin or the peptide of the present invention and/or a substance having affinity to the autoantibody of the present invention can be applied, for example, in a single dose of about 1-30 g, about one to 5 times per one day.

An autoimmune response in a periodontal disease is initiated by the production of an autoantibody to keratin, which is present in the gingival epithelium, or its degradation product by periodontal bacterial enzyme. Therefore, an autoimmune response inhibitory effect can be further improved by using a periodontal bacterial enzyme inhibitor in combination with the autoimmune response inhibitor of the present invention, which is effective for the prophylaxis or treatment and the like of periodontal diseases and complications thereof. Examples of the periodontal bacterial enzyme inhibitor include those described in the above-mentioned patent documents 1-4 and non-patent documents 4-7, and a novel periodontal bacterial enzyme inhibitor selected by the below-mentioned screening method. The inhibitor may be combined with the autoimmune response inhibitor of the present invention or separately formulated. When the autoimmune response inhibitor and the periodontal bacterial enzyme inhibitor of the present invention are separately applied, they may be intraorally administered simultaneously or in a staggered manner.

In another embodiment, the autoimmune response inhibitor of the present invention can be applied to an autoantibody removal method known as an immunoadsorption therapy. This method can be applied to, for example, patients with a high risk of fatal complication such as a patient having an underlying disease such as diabetes, arteriosclerosis and Alzheimer's disease, and a pregnant woman with a risk of preterm delivery with a low birth weight baby, and severe autoimmune response in a periodontal disease. For example, an adsorption column wherein a substance having affinity to keratin or the peptide of the present invention and/or a substance having affinity to the autoantibody of the present invention are/is conjugated with a suitable insoluble carrier is produced and inserted into the flow path of plasma components in a plasma separator known per se, which is used for artificial dialysis and the like, whereby keratin or the peptide of the present invention and/or the autoantibody of the present invention, which are present in the plasma, can be adsorbed and removed. In addition, by contacting a blood cell component with the adsorption column, an antigen-presenting cell for a keratin fragment or the peptide of the present invention or a fragment thereof, and an autoantibody producing cell can also be adsorbed and removed.

(IV) Screening for Substance Inhibiting Autoimmune Response to Keratin or A Degradation Product Thereof.

A peptidic substance such as a secondary antibody to the aforementioned keratin or the peptide of the present invention or the autoantibody of the present invention, and the like, or a substance other than a nucleic acid substance such as an aptamer of the autoantibody of the present invention and the like can be utilized as an active ingredient of the autoimmune response inhibitor of the present invention as long as it has affinity to the autoantibody of the present invention. Therefore, the present invention also provides a screening method of a substance inhibiting an autoimmune response to keratin or the peptide of the present invention, which comprises selecting a substance having affinity to the autoantibody of the present invention. Said method includes the following steps:

(1) a step of contacting the autoantibody of the present invention with a test substance,
(2) a step of measuring their binding level, and
(3) a step of selecting a test substance bound to said autoantibody as a candidate inhibitory substance of said autoimmune response.

The autoantibody of the present invention can be obtained from interdental liquid, serum, plasma and the like of periodontal disease patients by the aforementioned method.

Examples of the test substance include protein, peptide, nonpeptidic compound, synthetic compound, fermentation product, cell extract, plant extract, animal tissue extract and the like, and these substances may be novel or known.

The binding level of the autoantibody of the present invention and a test substance can be measured by an appropriate combination of various methods known per se. For example, it can be measured by immobilizing a test substance on a solid phase, contacting the solid phase with the autoantibody of the present invention (e.g., addition of an autoantibody solution to solid phase etc.), removing unreacted antibody, contacting a labeled secondary antibody to the antibody with the solid phase, and measuring the amount of label that was bound to the solid phase. Alternatively, it can also be measured by immobilizing the autoantibody of the present invention on a solid phase, reacting labeled keratin or a degradation product by periodontal bacterial enzyme, which is an antigen to the antibody, with the solid phase in the presence or absence of a test substance, and measuring and comparing the amount of label bound to the solid phase. Furthermore, their binding level can also be measured by immobilizing one of the autoantibody of the present invention and a test substance on a sensorchip, contacting the other with a sensorchip, and using a surface plasmon resonance (SPR) method.

(V) RANKL Expression Inhibitor

Keratin or the peptide of the present invention that transferred from a gingival tissue into the blood not only stimulate the proliferation of T cells and induce an autoimmune response thereto, but also induces expression of RANKL in T cells. The activated T cell stimulates macrophage to induce inflammatory cytokines such as TNF-α, IL-1, IL-6 and the like, initiate and aggravate periodontitis, as well as induce expression of RANKL in osteoblast and bone marrow stromal cells. It is considered that these RANKL expressing cells induce differentiation of osteoclast progenitor cell into osteoclast and promote bone resorption, whereby alveolar bone is destroyed. Since a substance having affinity to keratin or the peptide of the present invention can shut off an action of keratin or the peptide on T cells and the like, expression of RANKL in T cells and the like can be inhibited and alveolar bone destruction and initiation or aggravation of periodontitis can be suppressed. Accordingly, the present invention also provides a RANKL expression inhibitor and an agent for the prophylaxis or treatment of periodontal diseases and complications thereof, which contain a substance having affinity to keratin or the peptide of the present invention.

Examples of the substance having affinity to keratin or the peptide of the present invention include, but are not limited to, the aforementioned antibody to keratin or the peptide of the present invention, an aptamer to keratin or the peptide of the present invention and the like.

A substance having affinity to keratin or the peptide of the present invention can be directly administered or administered as a suitable pharmaceutical composition. The pharmaceutical composition used for the administration may contain a substance having affinity to keratin or the peptide of the present invention, and a pharmacologically acceptable carrier, diluent or excipient. Such pharmaceutical composition is provided in a dosage form suitable for oral or parenteral administration.

As a composition for parenteral administration, injection, suppository, intranasal agent and the like are used. Injection may include dosage forms of intravenous injection, subcutaneous injection, intradermal injection, muscular injection, drip injection and the like. Such injection can be prepared according to a known method. A preparation method of injection include dissolving, suspending or emulsifying with a substance having affinity to keratin or the peptide of the present invention in an aseptic aqueous liquid or an oily liquid generally used for injection. As aqueous liquid for injection, saline, isotonic solution containing glucose or other auxiliary agent and the like are used, and may be used in combination with a suitable solubilizing agent, such as alcohol (e.g., ethanol), polyalcohol (e.g., propylene glycol, polyethylene glycol), nonionic surfactant [e.g., polysorbate 80, HCO-50 (polyoxyethylene (50 mol) adduct of hydrogenated castor oil)] and the like. As an oily liquid, sesame oil, soybean oil and the like are used, and as a solubilizing agent, benzyl benzoate, benzyl alcohol and the like may be used in combination. The prepared injection is preferably filled in a suitable ampoule. A suppository to be used for rectal administration may be prepared by mixing a substance having affinity to keratin or the peptide of the present invention with a general base for suppository.

Examples of the composition for oral administration include solid or liquid dosage form, specifically tablet (including sugar-coated tablet, film-coated tablet), pill, granule, powder, capsule (including soft capsule), syrup, emulsion, suspension and the like. Such composition is produced by a known method, and optionally contains a carrier, a diluent or an excipient generally used in the pharmaceutical field. As carriers and excipients for tablets, lactose, starch, saccharose and magnesium stearate are used.

The above-mentioned parenteral or oral pharmaceutical composition is conveniently prepared in a dosage form with a dosage unit compatible with the dose of the active ingredient. Examples of the dosage form with a dosage unit include tablet, pill, capsule, injection (ampoule) and suppository. A m substance having affinity to keratin or the peptide of the present invention is preferably contained in generally 0.1-500 mg per dosage form with a dosage unit, 5-100 mg for injection and 10-250 mg for other dosage form.

While the dose of the above-mentioned medicament containing a substance having affinity to keratin or the peptide of the present invention varies depending on the subject of administration, symptom, administration route and the like, for example, a single dose of a substance having affinity to keratin or the peptide of the present invention is generally about 0.0001-20 mg/kg body weight, which is orally or parenterally administered about 1-5 times per day when it is a low-molecular-weight compound, and when it is antibody, nucleic acid and the like, it is conveniently administered once a day—once in several months by intravenous injection. In the case of other parenteral administration and oral administration, an amount analogous thereto can be administered. When the symptom is particularly severe, the dose may be increased according to the symptom.

(VI) Screening for Substance Inhibiting RANKL Expression (1)

A substance other than peptidic or nucleic acid substance such as an antibody or an aptamer to the aforementioned keratin or the peptide of the present invention can be utilized as an active ingredient of the RANKL expression inhibitor of the present invention as long as it has affinity to keratin or the peptide of the present invention. Therefore, the present invention also provides a screening method of a substance inhibiting RANKL expression, which comprises selecting a substance having affinity to keratin or the peptide of the present invention. Said method includes the following steps:

(1) a step of contacting keratin or the peptide of the present invention with a test substance,
(2) a step of measuring their binding level, and
(3) a step of selecting a test substance bound to keratin or the peptide as a candidate inhibitory substance of RANKL expression.

Keratin or the peptide of the present invention can be obtained by the aforementioned method.

Examples of the test substance include protein, peptide, nonpeptidic compound, synthetic compound, fermentation product, cell extract, plant extract, animal tissue extract and the like. These substances may be novel or known.

The binding level of keratin or the peptide of the present invention and a test substance can be measured by an appropriate combination of various methods known per se. For example, it can be measured by immobilizing a test substance on a solid phase, contacting the solid phase with keratin or the peptide of the present invention, removing unreacted keratin or peptide, contacting a labeled antibody to keratin or the peptide with the solid phase, and measuring the amount of the label that was bound to the solid phase. Alternatively, it can also be measured by immobilizing keratin or the peptide of the present invention on a solid phase, reacting a labeled antibody to keratin or the peptide with the solid phase in the presence or absence of a test substance, and measuring and comparing the amount of label bound to the solid phase. Furthermore, their binding level can also be measured by immobilizing one of keratin or the peptide of the present invention and a test substance on a sensorchip, contacting the other with a sensorchip, and using a surface plasmon resonance (SPR) method.

(VII) Screening for Substance Inhibiting RANKL Expression (2)

Keratin or the peptide of the present invention that transferred from a gingival tissue into the blood is considered to induce expression of RANKL in T cells via a receptor on the cell surface. Therefore, a substance showing an antagonistic activity on the receptor (that is, an action to shut off induction of RANKL expression by keratin or the peptide of the present invention, which is a ligand, by competitively binding to the receptor) is useful as a substance inhibiting the RANKL expression, like a substance having affinity to keratin or the peptide of the present invention. That is, the present invention also provides a method of screening for a substance inhibiting RANKL expression, comprising selecting a substance showing an antagonistic activity on a receptor of keratin or the peptide of the present invention. Said method includes the following steps:

(1) a step of contacting, in the presence and absence of a test substance, non-human mammal-derived T cell immunized with keratin or the peptide of the present invention with said keratin or peptide, (2) a step of measuring one or more selected from the group consisting of
 a) a binding level of said keratin or peptide to the T cell,
 b) a level of T cell proliferation, and
 c) an expression level of RANKL in the T cell, each of which in the presence and absence of the test substance, and (3) a step of selecting a test substance that decreased any of the above-mentioned a)-c) as a candidate inhibitory substance of RANKL expression.

As a method of immunizing a non-human mammal (e.g., mouse, rat, rabbit and the like) with keratin or the peptide of the present invention, a method similar to immunization of animal when preparing an antibody to keratin or the peptide of the present invention can be used. The T cell derived from an animal can be obtained by, for example, collecting a blood sample from the animal, and separating and collecting, for example, CD3 positive cells by using FACS, though not limited thereto. Keratin or the peptide of the present invention can be obtained by the aforementioned method.

Examples of the test substance include protein, peptide, nonpeptidic compound, synthetic compound, fermentation product, cell extract, plant extract, animal tissue extract and the like, and these substances may be novel or known.

The binding level of keratin or the peptide of the present invention to T cell can be obtained by, for example, immobilizing T cell on a plate, contacting keratin or the peptide of the present invention therewith, removing unreacted keratin or peptide, contact a labeled antibody to keratin or peptide with the cell, and measuring the amount of the label bound to the cell. The level of T cell proliferation can be examined by, for example, using a drug induced lymphocyte stimulation test (DLST). The expression of RANKL in T cell can be measured at an RNA level by quantitative RT-PCR, real-time RT-PCR, Northern blotting and the like, or at a protein level by ELISA, RIA, immunohistostaining, Western blotting and the like using an anti-RANKL antibody.

As a result of the above-mentioned measurement, a test substance that decreased the binding level of keratin or the peptide of the present invention to T cell, the level of T cell proliferation, or the expression level of RANKL in T cell by not less than 20%, preferably not less than 30%, more preferably not less than 40%, particularly preferably not less than 50%, as compared to the absence of the test substance, can be selected as a candidate RANKL expression inhibitory substance.

(VIII) Screening for Receptor of Keratin or the Peptide of the Present Invention Once a receptor of keratin or the peptide of the present invention, which is present on the T cell surface, is isolated, an RANKL expression inhibitory substance can be more efficiently screened for, by using the binding level of the receptor and a test substance, growth of T cell with forced expression of the receptor, or the expression level of RANKL in the cell as an index. A receptor of keratin or the peptide of the present invention can be isolated using affinity to keratin or the peptide as an index and by, for example, SPR method, dual polarization interferometry (DPI), two-hybrid method, the method described in WO 02/056026 which is a combination of membrane protein library (MPL) and mass spectrometry, and the like. Using the two-hybrid method, a DNA encoding a receptor of keratin or the peptide of the present invention can be directly obtained, and therefore, T cell with forced expression of the receptor can be produced rapidly.

(IX) Periodontal Disease Diagnosis

Since the peptide of the present invention and the autoantibody of the present invention are specifically detected in periodontal bacterium patients, it can be utilized as a diagnostic marker of a periodontal disease. That is, the present invention provides a test method for the diagnosis of a periodontal disease of a test animal, comprising measuring an amount of one or more peptides selected from the group of peptides consisting of amino acid sequences which are the same or substantially the same as respective amino acid sequences shown by SEQ ID NOs: 1-10, and/or one or more autoantibodies selected from the group consisting of autoantibodies to respective peptides of said group of peptides, in a biological sample obtained from the test animal. The "substantially the same amino acid sequence" here is as defined for the above-mentioned (II-1). The "examination for diagnosis" means measurement of the amount of the peptide and/or the autoantibody, and comparison with the measured value of the control sample where necessary. As the subject animal, a mammal (e.g., human, dog, cat, bovine, swine, sheep, goat, monkey, mouse, rat etc.) suspected of being affected with a periodontal disease can be mentioned.

While a biological sample derived from a test animal to be the test sample is not particularly limited, it is preferably less invasive to the animal. Examples thereof include those easily obtained from the body such as blood, plasma, serum, interdental liquid, urine, saliva and the like. When serum and plasma are used, blood samples can be prepared by collecting blood from a test animal according to a conventional method, and a separating a liquid component. When an interdental liquid is used, for example, a sample can be prepared according to the method described in the below-mentioned Examples and the like.

When the detection target is the peptide of the present invention, a high-molecular-weight protein fraction and the like can also be separated and removed in advance where necessary by using a spin column and the like. When the detection target is the autoantibody of the present invention, a low-molecular-weight peptide fraction and the like can also be separated and removed in advance.

(IX-1) Detection of Peptide of the Present Invention (1)

The peptide of the present invention in a biological sample can be detected by, though not limited to, applying a biological sample to a method based on a combination of various molecular weight determination methods, such as gel electrophoresis, various separation and purification methods (e.g., ion exchange chromatography, hydrophobic chromatography, affinity chromatography, reversed-phase chromatography and the like), ionization method (e.g., electron impact ionization method, field desorption method, secondary ionization method, fast atom bombardment method, matrix-assisted laser desorption ionization (MALDI), electrospray ionization method and the like), mass spectrometer (e.g., double-focusing mass spectrometer, quadrupole analyzer, time-of-flight mass spectrometer, Fourier-transform mass spectrometer, ion cyclotron mass spectrometer and the like) and the like, and detecting a band, spot or peak corresponding to the molecular weight of the peptide. Since the peptide of the present invention has a known amino acid sequence, a method including producing an antibody recognizing the amino acid sequence, and detecting the peptide according to Western blotting and various immunoassays is more preferably used. Furthermore, the hybrid detection method in the above-mentioned method is also effective.

While the peptides consisting of the respective amino acid sequences shown by SEQ ID NOs: 1-10 have molecular weights (calculated) of 2215.10, 2277.18 (2293.18 when Met is oxidized), 2638.37, 1377.73, 2543.20, 1221.64, 1410.66, 1658.88, 1885.91 and 2175.10, respectively, it is needless to say that the measured values may slightly vary depending on the measurement methods and measurement devices to be used. For example, when the method uses a mass spectrometer, the peak intensity appearing at the position of calculated value±0.5% (preferably ±0.3%, more preferably ±0.1%) is preferable measured.

One of the particularly preferable measurement methods in the test methods of the present invention is, for example, a method including contacting a test sample with a surface of a plate to be used for time-of-flight mass spectrometry, and measuring the mass of a component trapped on the surface of said plate by a time-of-flight mass spectrometer. A plate applicable to a time-of-flight mass spectrometer may be any as long as it has a surface structure capable of efficiently adsorbing the peptide of the present invention, which is the detection target. Examples of such surface structure include coating with a functional group-added glass, Si, Ge, GaAs, GaP, $SiO_2$, $SiN_4$, modified silicon, wide range of gels and polymers (e.g., (poly)tetrafluoroethylene, (poly)vinylidene difluoride, polystyrene, polycarbonate, or a combination thereof and the like). Examples of the surface structure having plural monomers or polymer sequences include coating with linear and cyclic polymers of nucleic acid, polysaccharide, lipid, peptide having α-, β- or ω-amino acid, carrier on gel surface used for chromatography (carriers crosslinked with anionic/cationic compound, $C_{1-18}$ hydrophobic compound, hydrophilic compound (e.g., silica, nitrocellulose, celluloseacetate, agarose etc.) and the like), artificial homopolymer (e.g., polyurethane, polyester, polycarbonate, polyurea, polyamide, polyethyleneimine, polyarylenesulfide, polysiloxane, polyimide, polyacetate etc.), heteropolymer wherein any of the above-mentioned compounds bound (covalent and noncovalent bond) with known medicaments or natural compounds and the like.

In a preferable embodiment, a support to be used as a mass spectrometry plate is a base thin layer-coated with polyvinylidene difluoride (PVDF), nitrocellulose or silica gel, particularly preferably PVDF [generally, it is not particularly limited as long as it is used for mass spectrometry plates and, for example, insulator (glass, ceramics, plastic resin etc.), metal (aluminum, stainless steel etc.), a conductive polymer, a complex thereof and the like can be mentioned, with preference given to an aluminum plate] (see WO 2004/031759). The shape of the support can be appropriately designed to particularly match a sample inlet port of a mass spectrometer to be used, though not limited thereto. Examples of such plate for mass spectrometry, which is thin layer-coated with PVDF, preferably include blotchip (registered trade mark, Protosera) and the like.

Preferably, the coating means a thin layer formed by depositing a coating molecule in a dispersed state on the support, rather than overlaying a structure formed in advance such as a membrane on a support. While the mode of depositing coating molecules is not particularly limited, the method exemplified as the preparation method of a plate for mass spectrometry mentioned below is preferably used.

While the thickness of the thin layer can be appropriately selected from the range that does not exert an unpreferable influence on the transcription efficiency, mass spectrometry measurement sensitivity and the like of molecules contained in the tissue or cell, it is, for example, about 0.001-about 100 μm, preferably about 0.01-about 30 μm.

A plate (support) for mass spectrometry can be prepared according to a method known per se. For example, the above-mentioned preferable plate for mass spectrometry is prepared by thin layer-coating the surface of the support with a coating molecule such as PVDF and the like. Preferable examples of the coating method include spreading, spraying, vapor deposition, immersion, printing, sputtering and the like.

For "spreading", a solution of a coating molecule dissolved in a suitable solvent, for example, an organic solvent such as dimethyl formamide (DMF) and the like at a suitable concentration (e.g., about 1-about 100 mg/mL) (coating molecule-containing solution) can be applied to a substrate with a suitable instrument such as brush and the like.

For "spraying", a coating molecule-containing solution prepared in the same manner as above is charged in an atomizer, and sprayed such that PVDF is uniformly deposited on the substrate.

For "vapor deposition", a thin layer of coating molecule (may be solid or solution) can be formed on the surface of a substrate by using a conventional vacuum vapor deposition equipment for production of organic thin film, and heating and vaporizing said molecule in a vacuum chamber containing the substrate.

For "immersion", a substrate only needs to be immersed in a coating molecule-containing solution prepared in the same manner as above.

For "printing", various printing techniques that can be generally used according to the material of a substrate can be appropriately selected and utilized; for example, screen printing and the like are preferably used.

For "sputtering", a thin layer can be formed by, for example, applying a high voltage DC between a substrate and coating molecule while introducing an inert gas (e.g., Ar gas etc.) under vacuum, colliding the ionized gas against said molecule, and depositing the flicked coating molecule on the substrate.

The coating may be applied on the whole surface of a substrate or only a surface subjected to mass spectrometry (fraction).

A coating molecule can be used in an appropriate, preferable form according to the coating means. For example, a form of a coating molecule-containing solution, a coating molecule-containing vapor, a solid coating molecule and the like can be applied to a substrate, and a form of coating molecule-containing solution is preferably applied. "Apply" means contacting the coating molecule to a support such that the coating molecules remain or are deposited on the support after contact. While the amount of application is not particularly limited, the amount of the coating molecule is, for example, about 10-about 100,000 μg/cm$^2$, preferably about 50-about 5,000 μg/cm$^2$. The solvent is removed by air drying, vacuum drying and the like after application.

The surface of a substrate for mass spectrometry plate may be modified (processed) in advance by a suitable physical or chemical method before coating with coating molecules. Specifically, methods such as polishing, damaging, acid treatment, alkali treatment, glass treatment (tetramethoxysilane and the like) of the surface of the plate and the like can be recited as examples.

A test sample is transferred to a plate (support) for mass spectrometry by directly applying an untreated biological sample from a patient, which becomes a test sample, or after removing high-molecular-weight proteins and concentrating the sample by using an antibody column or other method, to SDS-polyacrylamide gel electrophoresis or isoelectric focusing, and contacting the gel with the plate after electrophoresis to allow transcription thereof (blotting). As a transcription apparatus, a known one can be used. The method for transcription per se is known. Preferably, electric transcription is used. A sample developed on the gel after electrophoresis is transferred to a plate for mass spectrometry by various methods (diffusion, electric force, etc.). As a buffer to be used for electric transcription, a buffer having pH 7-9 and a low salt concentration is preferably used. Specific examples include Tris buffer, phosphate buffer, borate buffer, acetate buffer and the like. Examples of the Tris buffer include Tris/glycine/methanol buffer, SDS-Tris-tricine buffer and the like, examples of the phosphate buffer include ACN/NaCl/isotonic phosphate buffer, sodium phosphate/ACN and the like, examples of the borate buffer include sodium borate-hydrochloric acid buffer, Tris-borate/EDTA, borate/ACN and the like, and examples of the acetate buffer include Tris-acetate/EDTA and the like. Preferred is Tris/glycine/methanol buffer or sodium borate-hydrochloric acid buffer. As the composition of the Tris/glycine/methanol buffer, for example, Tris about 10-15 mM, glycine 70-120 mM, and methanol 7-13% can be mentioned. As the composition of the sodium borate-hydrochloric acid buffer, for example, sodium borate about 5-20 mM can be mentioned.

In this way, molecules present in a test sample including target molecule are efficiently trapped on the surface of a support. After drying the plate, a reagent called matrix may be added to absorb laser light and promote ionization of the analysis target molecule by energy transfer, which is advantageous for the subsequent mass spectrometry (by MALDI method). As said matrix, those known in mass spectrometry can be used. Examples thereof include, but are not limited to, sinapinic acid (SPA (=3,5-dimethoxy-4-hydroroxycinnamic acid)), indoleacrylic acid (IAA), 2,5-dihydroxybenzoic acid (DHB), α-cyano-4-hydroxycinnamic acid (CHCA) and the like. Preferred is DHB or CHCA.

The presence and amount of the peptide of the present invention, which is the target molecule, can be identified from the information relating to the molecular weight, which is obtained by mass spectrometry of the molecules in a test sample trapped on the surface of the support by the above-mentioned method.

Mass spectrometer is an apparatus for measuring and detecting the molecular weight of a substance by ionizing a gaseous sample, injecting the molecules and molecule fragments thereof into the electromagnetic field, separating the molecules and molecule fragments based on the mass number/charge number from the movement thereof and determining the spectrum of the substance. Mass spectrometers based on the principles of MALDI-TOFMS method using, in combination, matrix assisted laser desorption ionization (MALDI) including mixing a sample and matrices absorbing a laser light, drying same to allow crystallization, and directing, into the vacuum, an ionized analysis target obtained by ionization by energy transfer from the matrix and instant heating by laser irradiation, and time-of-flight mass spectrometry (TOFMS) including analyzing mass number from the difference in the flying time of sample molecule ions by initial acceleration, a method of direct, electric ionization from liquid by placing one analysis target on one droplet, a nanoelectrospray mass spectrometry (nano-ESMS) method including electrically spraying a sample solution in the air and leading individual analysis target polyvalent ions in an unfolded state to the gaseous phase and the like can be used.

The method per se of mass spectrometry of the molecules on a mass spectrometry plate is known. For example, the method described in WO 2004/031759 can be used after appropriate alteration as necessary.

The presence or absence of the target molecule in the test sample and the amount thereof can be identified based on the molecular weight information of the target molecule from the results of mass spectrometry. In this step, the information from the mass spectrometer can also be compared to the mass spectrometry data of a biological sample from a healthy subject by using any program, and output as differential information. Such program is well known, and it will be appreciated that those of ordinary skill in the art can construct or alter such program with ease by using a known information processing technique.

In a particularly preferable embodiment, each of the above-mentioned steps are performed using a blotchip by Protosera as a plate for mass spectrometry, the peptide of the present invention is subjected to quantification and comparison (differential analysis) by an MALDI type mass spectrometer. Moreover, where necessary, the peptide remaining in the same chip can also be identified. Alternatively, it is possible to perform the steps up to quantification and comparison (differential analysis) of a test sample by the blotchip system of Protosera, identify the peptide by a combination equipment of high performance liquid chromatography and ion spray type mass spectrometer (LC-MS/MS).

(IX-2) Detection of Peptide of the Present Invention (2)

In the test method of the present invention, the peptide of the present invention can also be measured by using an antibody thereto. Such method is particularly useful since the peptide can be detected with high sensitivity and high precision without using a special apparatus such as the above-mentioned mass spectrometer, by constructing an optimized immunoassay system and producing a kit containing same.

As an antibody against the peptide of the present invention, the same antibody as the therapeutic antibody of the above-mentioned (II-2) can be utilized. The test method of the present invention using the antibody is not particularly limited, and any measurement method may be used as long as the amount of an antibody, antigen or antibody-antigen complex corresponding to the amount of antigen in a test sample is detected by a chemical or physical means, and its amount is calculated from a standard curve produced using a standard solution containing a known amount of antigen. For example, nephelometry, competitive method, immunometric method, sandwich method, Western blotting, SPR, turbidimetry and the like are preferably used.

As a label to be used for a measurement method using a labeling substance, radioisotope, enzyme, fluorescent substance, luminescent substance and the like are used. As the radioisotope, [$^{125}$I], [$^{131}$I], [$^{3}$H], [$^{14}$C] and the like are used. As the above-mentioned enzyme, a stable enzyme having a large specific activity is preferable and, for example, β-galactosidase, β-glucosidase, alkaline phosphatase, peroxidase, malate dehydrogenase and the like are used. As the fluorescent substance, fluorescamine, fluorescein isothiocyanate and the like are be used. As the luminescent substance, luminol, luminol derivative, luciferin, lucigenin and the like are used. Furthermore, biotin-avidin system can be used for the conjugation of an antibody or antigen and a labeling agent.

For insolubilization of an antigen or antibody, physical adsorption can be used, or a method using chemical binding generally used for insolubilizing or immobilizing a protein, an enzyme and the like may also be used. Examples of the carrier include insoluble polysaccharides such as agarose, dextran, cellulose and the like, synthetic resins such as polystyrene, polyacrylamide, silicon and the like, and glass and the like.

In the sandwich method, the amount of the peptide of the present invention in a test sample can be quantified by reacting a test sample with an insolubilized antibody (first reaction), further reacting with other labeled antibody (second reaction), and measuring the amount (activity) of the labeling agent on an insolubilized carrier. The first reaction and the second reaction may be performed in a reverse order, or simultaneously or in a staggerd manner.

A monoclonal antibody against the peptide of the present invention can also be used for a measurement system other than the sandwich method, such as competitive method, immunometric method, nephelometry and the like.

In the competitive method, an antigen and a labeled antigen in a test sample are competitively reacted with an antibody, unreacted labeled antigen (F) and labeled antigen (B) bound to the antibody are separated (B/F separation), the amount of the label of B or F is measured, and the amount of antigen in the test sample is quantified. As this reaction method, a liquid phase method using a soluble antibody as an antibody, B/F separation with polyethylene glycol, a secondary antibody to the aforementioned antibody and the like, or a solid phase immobilization method using a solid-phase-immobilized antibody as a primary antibody, or a soluble primary antibody and a solid-phase-immobilized antibody as a secondary antibody is used.

In the immunometric method, an antigen and a solid-phase-immobilized antigen in a test sample are competitively reacted with a given amount of labeled antibody and the solid phase and the liquid phase are separated, or an antigen and an excess amount of a labeled antibody in a test sample are reacted, a solid-phase-immobilized antigen is added to bind unreacted labeled antibody to the solid phase, and the solid phase and the liquid phase are separated. Then, the amount of the label in one phase is measured and the amount of the antigen in the test sample is quantified.

In nephelometry, the amount of an insoluble precipitate resulting from an antigen antibody reaction in a gel or solution is measured. Even when the amount of antigen in the test sample is a trace amount, and only a small amount of precipitate can be obtained, and laser nephelometry utilizing scattering of laser and the like are preferably used.

When such individual immunological measurement methods are applied to the quantification method of the present invention, special conditions, operation and the like are not necessary. The measurement system of the peptide of the present invention can be constructed by adding general technical consideration by those of ordinary skill in the art to the general conditions and operation for each method. The detail of such general technical means can be found by reference to reviews, books and the like.

For example, "Radioimmunoassay" edited by Hiroshi IRIE (Kodansha, published in 1974), "Supplementary Radioimmunoassay" edited by Hiroshi IRIE (Kodansha, published in 1979), "Enzyme Immunoasssay" edited by Eiji ISHIKAWA et al. (Igaku-Shoin, published in 1978), "Enzyme Immunoasssay" edited by Eiji ISHIKAWA et al. (2nd edition, Igaku-Shoin, published in 1982), "Enzyme Immunoasssay" edited by Eiji ISHIKAWA et al. (3rd edition, Igaku-Shoin, published in 1987), "Methods in ENZYMOLOGY" Vol. 70 (Immunochemical Techniques (Part A)), ibidem Vol. 73 (Immunochemical Techniques (Part B)), ibidem Vol. 74 (Immunochemical Techniques (Part C)), ibidem Vol. 84 (Immunochemical Techniques (Part D: Selected Immunoassays)), ibidem Vol. 92 (Immunochemical Techniques (Part E: Monoclonal Antibodies and General Immunoassay Methods)), ibidem Vol. 121 (Immunochemical Techniques (Part I: Hybridoma Technology and Monoclonal Antibodies)) (all above published by Academic Press) and the like can be referred to.

Since the peptide of the present invention is comprised of a protein degradation product, various molecules such as undegraded protein, analogous peptides having a common cleavage site and the like may influence the measurement values in the general "sandwich ELISA system". In the first step, a so-called immuno-mass spectrometry method can be utilized, wherein a biological sample is immunoaffinity-purified by an antibody, and a fraction bound to the antibody is subjected to mass spectrometry in the second step, and identified and quantified based on the precise molecular weight as the standard (e.g., see Rapid Commun. Mass Spectrom. 2007, 21: 352-358). For example, in the case of using a blood sample as a biological sample, even when said sample is directly measured with a MALDI type mass spectrometer, a peak of biomarker is not observed. However, according to an immuno-mass spectrometry method, undegraded protein and analogous peptide are completely separated with a mass spectrometer, and can be quantified using a precise molecular weight of the biomarker as standard at high specificity and sensitivity.

Alternatively, as other test method of the present invention using the antibody of the present invention, a method including immobilizing the antibody on the surface of a probe applicable to a mass spectrometer as mentioned above, contacting a test sample with the antibody on the probe, analyzing a biological sample component trapped by the antibody by mass spectrometry, and detecting a peak corresponding to the molecular weight of a marker peptide recognized by the antibody can be mentioned.

(IX-3) Detection of Autoantibody of the Present Invention

In the test method of the present invention, the autoantibody of the present invention can be measured by using a peptide recognized by the autoantibody, secondary antibody to the autoantibody, an antibody that recognizes a peptide recognized by the autoantibody and the like. As the peptide recognized by the autoantibody of the present invention, the same therapeutic peptide as in the above-mentioned (II-1) can be utilized. As a secondary antibody to the autoantibody of the present invention, the same therapeutic secondary antibody as in the above-mentioned (II-3) can be utilized. As an antibody that recognizes a peptide recognized by the autoantibody of the present invention, the same antibody as the therapeutic antibody of the above-mentioned (II-2) can be utilized. The test method of the present invention is not particularly limited, and any measurement method may be used as long as the amount of an antigen, antibody, or antigen-antibody complex corresponding to the amount of autoantibody in a test sample is detected by a chemical or physical means, and its amount is calculated from a standard curve produced using a standard solution containing a known amount of antibody. For example, nephelometry, competitive method, immunometric method, sandwich method, Western blotting and the like are preferably used.

As a label used for a measurement method using a labeling substance, a method for insolubilizing an antigen or antibody and the like, those exemplified in the above-mentioned (IX-2) can be used in the same manner.

In one preferable embodiment, the amount of the autoantibody of the present invention in a test sample can be quantified by reacting a test sample with an insolubilized peptide recognized by an autoantibody (first reaction), further reacting with a labeled secondary antibody or labeled antigen to the autoantibody (second reaction), and measuring the amount (activity) of the labeling agent on an insolubilized carrier. The first reaction and the second reaction may be performed in a reverse order, simultaneously or in a staggered manner.

In the competitive method, an autoantibody in a test sample and a labeled antibody that recognizes the same antigen are competitively reacted with an antigen peptide, unreacted labeled antibody (F) and labeled antibody (B) bound to the antigen are separated (B/F separation), the amount of the label of B or F is measured, and the amount of autoantibody in the test sample is quantified.

In the immunometric method, an autoantibody in a test sample, and a solid-phase-immobilized antibody that recognizes the same antigen are competitively reacted with a given amount of labeled antigen and the solid phase and the liquid phase are separated, or an autoantibody in a test sample and an excess amount of a labeled antigen are reacted, a solid-phase-immobilized antibody is added to bind unreacted labeled antigen to the solid phase, and the solid phase and the liquid phase are separated. Then, the amount of the label in one phase is measured and the amount of the autoantibody in the test sample is quantified.

In nephelometry, the amount of an insoluble precipitate resulting from an antigen antibody reaction in a gel or solution is measured. Even when the amount of autoantibody in the test sample is a trace amount, and only a small amount of precipitate can be obtained, and laser nephelometry utilizing scattering of laser and the like are preferably used.

Alternatively, using a surface plasmon resonance (SPR) method, a peptide recognized by an autoantibody is immobilized on the surface of a commercially available sensor-chip (e.g., manufactured by Biacore) by a conventional method, contacting the peptide with a test sample, a light having a particular wavelength is irradiated on the sensor-chip from a particular angle, and the presence or absence of the binding of the autoantibody to the immobilized peptide can be determined using the change of resonance angle as an index. Also, the autoantibody of the present invention can also be measured by a method including immobilizing a peptide recognized by an autoantibody on the surface of a probe applicable to a mass spectrometer as mentioned above, contacting a test sample with the peptide on the probe, analyzing a biological sample component trapped by the peptide by mass spectrometry, and detecting a peak corresponding to the molecular weight of an autoantibody recognizing the peptide, and the like.

When the level of the peptide of the present invention and/or the autoantibody of the present invention in a sample derived from a test animal as measured by any of the above-mentioned methods significantly increases as compared to the level of the marker in a control sample of a normal animal, the subject animal can be diagnosed to have a high possibility of being affected with a periodontal disease.

The test method of the present invention preferably includes collecting biological samples from patients (animal patients) in a chronological order, and examining time course changes of expression of the peptide of the present invention and/or the autoantibody of the present invention in each sample. While the interval of collection of biological sample is not particularly limited, it is desirable to collect samples as often as possible unless the QOL of the patients (animal patients) is impaired. When the level of the marker decreases over time, the pathology of periodontal disease in the patients (animal patients) is judged to have high likelihood of improvement.

The test method of periodontal diseases by the above-mentioned sampling in a chronological order can be used to evaluate the treatment effect of a treatment measure applied between the previous sampling and the most recent sampling in test subjects (patients (animal patients)). That is, in samples before and after the treatment, when the condition after the treatment provides improvement of the pathology as compared to the condition before the treatment, the treatment can be evaluated to provide effects. On the other hand, when the condition after the treatment does not show improvement of pathology as compared to the condition before the treatment, or judged to have been aggravated, the treatment can be evaluated to provide no effect.

(X) Production Method of Periodontal Disease Animal Model

As shown in the below-mentioned Examples, when a non-human mammal is immunized with keratin or the peptide of the present invention, alveolar bone destruction occurs in the animal. Therefore, the present invention also provides a production method of a periodontal disease animal model by immunizing a non-human mammal with keratin or the peptide of the present invention. As a method for immunizing an animal with keratin or the peptide of the present invention, the above-mentioned method can also be utilized. The keratin or the peptide is intragingivally administered for stimulation, whereby the symptom of the periodontal disease can be remarkably reproduced.

(XI) Keratin Degradation Promoter

The present invention has clarified for the first time that periodontal bacterial enzymes such as gingipain and the like have a keratin degrading activity. Therefore, the present invention also provides a keratin degradation promoter containing a periodontal bacterial enzyme. A keratin degradation promoter can be utilized for, for example, improvement of skin cornification of finger, heel, knee, elbow, ankle and the like, improvement of wavy hair, treatment of deformation or discoloration of nail such as ingrown toenail and the like, treatment of nail infections such as tinea unguium and the like, facilitation of skin permeability of medicaments such as ointment, cream and the like, and the like.

As the periodontal bacterial enzyme, preferred is gingipain produced by *P. gingivalis*, for example, Kgp, RgpB and HRgpA. These enzymes can be isolated and purified from the periodontal bacterium according to, for example, the method described in Curr Protoc Protein Sci. 2007 August; Chapter 21: Unit 21.20. In addition, the enzymes can also be obtained by, based on the sequence information shown by GeneIDs: 6330196 (kgp), 6330928 (rgpB) and 6330747 (rgpA), from among the total genome sequences of *P. gingivalis* ATCC33277 strain registered in the NCBI database as Refseq No. NC_010729.1, cloning these enzyme genes according to a conventional method, introducing the clone into a suitable host cell, culturing the resulting transformant, and recovering a recombinant enzyme protein from the culture medium.

The periodontal bacterial enzyme obtained as mentioned above can be directly, or as a suitable composition, formulated into cosmetic agents, pharmaceutical products and the like including quasi-drugs. Examples of the composition include those containing a periodontal bacterial enzyme and a pharmacologically acceptable additive. Preferably, the composition is an external composition for the skin, hair, nail and the like, such as aqueous liquid, ointment, cream, powder, gel, oil, spray, wax, facial mask, adhesive preparation and the like.

The amount of the periodontal bacterial enzyme to be contained in the external composition is not particularly limited, and can be appropriately selected from the range of, for example, 0.1-99.9 wt %, preferably 1-99 wt %, relative to the whole composition. Only one kind of the periodontal bacterial enzyme may be used or two or more kinds thereof may be used in combination.

Examples of the additive to be used for the external composition include oil, surfactant, powder, coloring material, water, alcohols, thickener, chelating agent, silicones, antioxidant, active oxygen elimination agent, UV absorber, moisturizer, flavor, various medicinal components, preservative, pH adjuster, neutralizer and the like. They can be combined as appropriate as long as the effect of the present invention is not impaired.

An external composition containing a periodontal bacterial enzyme can be topically applied, for example, to the skin, hair, nail and the like at a single dose of about 1-10 g, 1 to 5 times per day.

(XII) Evaluation of Periodontal Bacterium Activity

The present invention also provides a method of evaluating the periodontal bacterium activity of a microorganism (whether or not it can be a causative bacterium of periodontal disease, or pathogenicity level thereof), using a keratin degradation action of the microorganism as an index. To be specific, a test bacterium, a secretion product thereof (e.g., culture supernatant) or a processed product thereof (e.g., concentrated liquid, purified fraction) is contacted with keratin, incubated for a given time, and the presence or absence of keratin degradation, and the level thereof are evaluated. As the keratin to be a substrate, keratin present in the gingival epithelium in the above-mentioned (I) (cytokeratin), a hard keratin having high sequence similarity to the keratin and the like can also be used. The incubation can be performed, for example, at 20-40° C., preferably 30-40° C., for 0.5-24 hr, preferably 1-12 hr. Keratin can be degraded by detecting a decrease of keratin protein amount, and production of a low-molecular-weight degradation product by, for example, gel electrophoresis, Western blotting, mass spectrometry and the like.

When the degradation of keratin is found in the presence of a subject bacterium, a secretion product thereof or a processed product thereof by the above-mentioned method, the microorganism is judged to have a periodontal bacterium activity, that is, it may cause a periodontal disease when a mammal is infected therewith in the oral cavity.

(XIII) Screening for Periodontal Disease Control Substance

Using an inhibitory or promoting action on keratin degradation by a periodontal bacterium as an index, a substance that suppresses or promotes a periodontal disease can be screened for. Such screening can be performed, for example, by using, in the evaluation method of periodontal bacterium activity in the above-mentioned (XII), a known periodontal bacterium (e.g., *P. gingivalis*) or a secretion product thereof or a processed product thereof (e.g., purified gingipain) instead of the subject bacterium and in the presence of a test substance during contact with keratin.

As the test substance, any known compound or novel compound can be used and, for example, nucleic acid, carbohydrates, lipid, protein, peptide, organic low-molecular-weight compound, a compound library and a random peptide library prepared by a combinatorial chemistry technique, or a natural component derived from microorganism, animals and plants, marine organism and the like, and the like can be mentioned. Particularly, for screening for a periodontal disease promoting substance, various food components, food additives and the like can be mentioned.

After the completion of incubation, the keratin degradation is measured in the same manner, and when keratin degradation decreased significantly by incubation in the presence of a test substance as compared to incubation in the absence of the test substance, the test substance can be selected as a candidate periodontal disease inhibitory substance. On the other hand, when keratin degradation increased significantly by incubation in the presence of a test substance as compared to incubation in the absence of the test substance, the test substance can be selected as a candidate periodontal disease promoting substance.

The thus-selected periodontal disease inhibitory substance can be subjected to further research and development as a candidate substance of a novel therapeutic drug for a periodontal disease. On the other hand, for example, a certain food additive is judged to be a periodontal disease promoting substance, information useful for the development of food suitable for the prophylaxis of a periodontal disease, which uses an additive free of a keratin degradation promoting action and which can replace said substance, can be provided.

The present invention is explained in more detail in the following by referring to Examples, which are not to be construed as limitative.

EXAMPLES

Example 1

Analysis of Periodontal Bacterial Enzymatic Degradation Product Derived from Rat Gingival Epithelial Cell (GEC)

Primary gingival epithelial cells (GEC; $6.4 \times 10^6$ cells) scraped from a rat were rinsed twice with phosphate buffered saline (PBS). The cells were divided into 4 groups (no treatment, Kgp treatment, RgpB treatment, HRgpA treatment). Three kinds of purified gingipains were respectively added thereto, and the mixtures were incubated at 37° C. for 1 hr. After completion of incubation, each treatment solution (1.5 µL) was mixed with a sample treatment solution for electrophoresis (NuPAGE (registered trade mark) LDS Sample Buffer 4×; Invitrogen, 4.5 µL), and the mixture was heat-treated at 70° C. for 10 min, and applied to 4-12% gradient polyacrylamide gel (Invitorigen) to perform electrophoresis. After completion of electrophoresis, the gel was cut out, laminated on BLOTCHIP (registered trade mark, Protosera, Inc.), and transcribed in a buffer for electric transcription (BLOTBuffer™; Protosera, Inc.) at 90 mA for 120 min. After completion of transcription, the surface of the chip was rinsed with ultrapure water, matrix (α-cyano-4-hydroxy cinnamic acid) was applied to the whole chip, and subjected to mass spectrometry by a matrix-assisted laser desorption ionization time-of-flight (MALDI-TOF) mass spectrometer (manufactured by Bruker Daltnics, Ultra-FlexII). The measurement parameter was Detector voltage 1685 V, Supression 1000, Fuzzy mode, Laser Intensity of 28-35, laser irradiation at 415 points per chip, 500 times of laser irradiations per point, 207,500 times in total of laser irradiation. Each peak intensity in the obtained spectrum was integrated for each M/z and converted to one integrated spectrum. The integrated spectrum was subjected to differential profiling analysis between treated solutions using ClinProTools (Bruker Daltonik GmbH). Furthermore, the thus-obtained analysis results were compared to the peak in the actual integrated spectrum.

As a result, in the Kgp-treated GEC, peptides having molecular weights of about 2215 and about 2230, which showed remarkable increase as compared to non-treatment and other gingipain treatment (peak 1 and peak 2); in the RgpB-treated GEC, peptides having molecular weights of about 2277 and about 2293, which showed remarkable increase as compared to non-treatment and other gingipain treatment (peak 3 and peak 4); and in RgpB- or HRgpA-treated GEC, peptide having a molecular weight of about 2638, which showed remarkable increase as compared to non-treatment and Kgp treatment (peak 5), were found (FIG. 1, Tables 1 and 2).

TABLE 1

Peak intensity ratio
(ratio of each peak intensity relative to enzyme-free group)

| | | Peak intensity ratio relative to control | | | |
|---|---|---|---|---|---|
| No | MW (calc) | Kgp | HRgpA | RgpB | Note |
| 1 | 2215.10 | 11.6 | | | |
| 2 | 2230.07 | 14.9 | | | |
| 3 | 2277.18 | | | 1.4 | |
| 4 | 2293.18 | | | 23.5 | Oxidized product of No. 3 |
| 5 | 2638.37 | | 8.4 | 18.7 | |

TABLE 2 p value (significant difference in each peak intensity relative to enzyme-free group)

| | MW | p value in T-test | | | |
|---|---|---|---|---|---|
| No | (calc) | Kgp | HRgpA | RgpB | Note |
| 1 | 2215.10 | 0.00105 | | | |
| 2 | 2230.07 | 0.00027 | | | |
| 3 | 2277.18 | | | 0.04790 | |
| 4 | 2293.18 | | | 0.02112 | Oxidized product of No. 3 |
| 5 | 2638.37 | | 0.00066 | 0.00242 | |

Example 2

Identification of Periodontal Bacterial Enzymatic Degradation Product Derived from GEC For identification, matrix-assisted laser desorption ionization time-of-flight (MALDI-TOF) mass spectrometer (Ultra-FlexII manufactured by Bruker Daltnics) was used, and mass calibration was performed using Bradykinin, Angiotensin II, Angiotensin I, Substance 9, Bombesin, Renin Substrate, ACTH Clip{1-17}, ACTH Clip{18-39}, and Somatostatin. Thereafter, profiling was performed on the refrectron measurement mode, and identification was performed by MS/MS analysis based on the selected peptide peak and fragment ion thereof by matching with NCBInr and SwissProt database through MASCOT search engine installed in Biotools (Bruker Daltonik GmbH).

As a result, peptides of peak Nos. 1, 2, 3 and 5 (to be referred to as peptides 1, 2, 3 and 5, respectively) were identified as peptides consisting of the amino acid sequences shown by SEQ ID NOs: 1, 15, 2 and 3, respectively. The peptide of peak No. 4 (to be also referred to as peptide 4) was peptide 3 with oxidized Met residue. As a result of homology search, it was clarified that peptide 1 was a fragment of Keratin 6A, peptide 2 was a fragment of Keratin 5, peptides 3 and 4 were fragments of Keratin 14, and peptide 5 was a fragment of Keratin 17. Furthermore, the results of homology search of ortholog and paralog of other mammals including human are shown in Tables 3-6. The amino acid sequences of the regions corresponding to peptides 1-5 were well conserved between mammals.

TABLE 3-1

| peptide No. | identified sequence [SEQ ID NO] | substrate | enzyme |
|---|---|---|---|
| 1 | YEELQITAGRHGDDLRNTK[1] | rat gingival epithelial cell | Kgp |
| 2 | YEELQQTAGRHGDDLRNTK[15] | rat gingival epithelial cell | Kgp |
| 3 | TKVMDVHDGKVVSTHEQVLR[2] | rat gingival epithelial cell | RgpB |
| 4 | TKVMDVHDGKVVSTHEQVLR + (O)[2] | rat gingival epithelial cell | RgpB |
| 5 | TIVEEVQDGKVISSREQVHQTTR[3] | rat gingival epithelial cell | RgpB/HRgpA |
| 6 | RTAAENEFVTLK[4] | human Keratin 6 | Kgp |
| 7 | AQYEEIAQRSRAEAESWYQTK[5] | human Keratin 6 | Kgp |
| 8 | TKFETEQALR[6] | human Keratin 17 | RgpB |
| 9 | DQYEKMAEKNR[7] | human Keratin 17 | RgpB |
| 10 | TIVEEVQDGKVISSR[8] | human Keratin 17 | RgpB |
| 11 | QFTSSSSIKGSSGLGGGSSR[9] | human Keratin 17 | RgpB |
| 12 | EVATNSELVQSGKSEISELR[10] | human Keratin 17 | RgpB |

| | Homology search results[SEQ ID NO] | | |
|---|---|---|---|
| peptide | Keratin 6B | | |
| No. | human | rat | mouse |
| 1 | YEELQITAGRHGDDLRNTK[1] | YEELQITAGRHGDDLRNTK[1] | YEELQVTAGRHGDDLRNTK[16] |
| 2 | | | |
| 3 | | | |
| 4 | | | |

TABLE 3-1-continued

| | |
|---|---|
| 5 | |
| 6 RTAAENEFVTLK[4] | RTKAENEFVTVK[17] |
| 7 AQYEEIAQRSRAEAESWYQTK[5] | AQYEDIAGRSRAEAESWY-QTK[18] |
| 8 | |
| 9 | |
| 10 | |
| 11 | |
| 12 | |

TABLE 3-2

| Peptide No. | identified sequence [SEQ ID NO] | substrate | enzyme |
|---|---|---|---|
| 1 | YEELQITAGRHGDDLRNTK[1] | rat gingival epithelial cell | Kgp |
| 2 | YEELQQTAGRHGDDLRNTK[15] | rat gingival epithelial cell | Kgp |
| 3 | TKVMDVHDGKVVSTHEQVLR[2] | rat gingival epithelial cell | RgpB |
| 4 | TKVMDVHDGKVVSTHEQVLR + (O)[2] | rat gingival epithelial cell | RgpB |
| 5 | TIVEEVQDGKVISSREQVHQTTR[3] | rat gingival epithelial cell | RgpB/HRgpA |
| 6 | RTAAENEFVTLK[4] | human Keratin 6 | Kgp |
| 7 | AQYEEIAQRSRAEAESWYQTK[5] | human Keratin 6 | Kgp |
| 8 | TKFETEQALR[6] | human Keratin 17 | RgpB |
| 9 | DQYEKMAEKNR[7] | human Keratin 17 | RgpB |
| 10 | TIVEEVQDGKVISSR[8] | human Keratin 17 | RgpB |
| 11 | QFTSSSSIKGSSGLGGGSSR[9] | human Keratin 17 | RgpB |
| 12 | EVATNSELVQSGKSEISELR[10] | human Keratin 17 | RgpB |

| | Homology search results[SEQ ID NO] Keratin 6A | | |
|---|---|---|---|
| Peptide No. | human | rat | mouse |
| 1 | YEELQVTAGRHGDDLRNTK[16] | YEELQITAGRHGDDLRNTK[1] | YEELQVTAGRHGDDLRNTK[16] |
| 2 | | | |
| 3 | | | |
| 4 | | | |
| 5 | | | |
| 6 | RTAAENEFVTLK[4] | RTAAENEFVTLK[4] | RTAAENEFVTVK[4] |
| 7 | AQYEEIAQRSRAEAESWYQTK[5] | AQYEEIAKRSRAEAESWYQTK[19] | AQYEDIAQRSRAEAESWY-QTK[18] |
| 8 | | | |
| 9 | | | |
| 10 | | | |
| 11 | | | |
| 12 | | | |

TABLE 3-3

| peptide No. | identified sequence [SEQ ID NO] | substrate | enzyme | Homology search results[SEQ ID NO] Keratin 6C human |
|---|---|---|---|---|
| 1 | YEELQITAGRHGDDLRNTK[1] | rat gingival epithelial cell | Kgp | YEELQVTAGRHGDDLRNTK[16] |
| 2 | YEELQQTAGRHGDDLRNTK[15] | rat gingival epithelial cell | Kgp | |
| 3 | TKVMDVHDGKVVSTHEQVLR[2] | rat gingival epithelial cell | RgpB | |
| 4 | TKVMDVHDGKVVSTHEQVLR + (O)[2] | rat gingival epithelial cell | RgpB | |
| 5 | TIVEEVQDGKVISSREQVHQTTR[3] | rat gingival epithelial cell | RgpB/HRgpA | |
| 6 | RTAAENEFVTLK[4] | human Keratin 6 | Kgp | RTAAENEFVTLK[4] |
| 7 | AQYEEIAQRSRAEAESWYQTK[5] | human Keratin 6 | Kgp | AQYEEIAQRSRAEAESWYQTK[5] |
| 8 | TKFETEQALR[6] | human Keratin 17 | RgpB | |

TABLE 3-3-continued

| peptide No. | identified sequence [SEQ ID NO] | substrate | enzyme | Homology search results[SEQ ID NO] Keratin 6C human |
|---|---|---|---|---|
| 9 | DQYEKMAEKNR[7] | human Keratin 17 | RgpB | |
| 10 | TIVEEVQDGKVISSR[8] | human Keratin 17 | RgpB | |
| 11 | QFTSSSSIKGSSGLGGGSSR[9] | human Keratin 17 | RgpB | |
| 12 | EVATNSELVQSGKSEISELR[10] | human Keratin 17 | RgpB | |

TABLE 4

| peptide No. | identified sequence [SEQ ID NO] | substrate | enzyme | Homology search results[SEQ ID NO] Keratin 5 human |
|---|---|---|---|---|
| 1 | YEELQITAGRHGDDLRNTK[1] | rat gingival epithelial cell | Kgp | |
| 2 | YEELQQTAGRHGDDLRNTK[15] | rat gingival epithelial cell | Kgp | YEELQQTAGRHGDDLRNTK[15] |
| 3 | TKVMDVHDGKVVSTHEQVLR[2] | rat gingival epithelial cell | RgpB | |
| 4 | TKVMDVHDGKVVSTHEQVLR + (O)[2] | rat gingival epithelial cell | RgpB | |
| 5 | TIVEEVQDGKVISSREQVHQTTR[3] | rat gingival epithelial cell | RgpB/HRgpA | |
| 6 | RTAAENEFVTLK[4] | human Keratin 6 | Kgp | RTTAENEFVMLK[20] |
| 7 | AQYEEIAQRSRAEAESWYQTK[5] | human Keratin 6 | Kgp | AQYEEIANRSRTEAESWYQTK[21] |
| 8 | TKFETEQALR[6] | human Keratin 17 | RgpB | |
| 9 | DQYEKMAEKNR[7] | human Keratin 17 | RgpB | |
| 10 | TIVEEVQDGKVISSR[8] | human Keratin 17 | RgpB | |
| 11 | QFTSSSSIKGSSGLGGGSSR[9] | human Keratin 17 | RgpB | |
| 12 | EVATNSELVQSGKSEISELR[10] | human Keratin 17 | RgpB | |

| peptide No. | Homology search results[SEQ ID NO] Keratin 5 | | | |
|---|---|---|---|---|
| | chimpanzee | bovine | rat | mouse |
| 1 | | | | |
| 2 | YEELQQTAGRHGDDLRNTK[15] | YEELQQTAGRNGDDLRNTK[15] | YEELQQTAGRHGDDLRNTK[15] | YEELQQTAGRHGDDLRNTK[15] |
| 3 | | | | |
| 4 | | | | |
| 5 | | | | |
| 6 | RTTAENEFVMLK[20] | RTTAENEFVMLK[20] | RTTAENEFVMLK[20] | RTTAENEFVMLK[20] |
| 7 | AQYEEIANRSRTEAESWYQTK[21] | AQYEDIANRSRTEAESWYQTK[22] | AQYEDIANRSRTEAESWYQTK[22] | AQYEDIANRSRTEAESWYQTK[22] |
| 8 | | | | |
| 9 | | | | |
| 10 | | | | |
| 11 | | | | |
| 12 | | | | |

TABLE 5

| peptide No. | identified sequence[SEQ ID NO] | substrate | enzyme |
|---|---|---|---|
| 1 | YEELQITAGRHGDDLRNTK[1] | rat gingival epithelial cell | Kgp |
| 2 | YEELQQTAGRHGDDLRNTK[15] | rat gingival epithelial cell | Kgp |
| 3 | TKVMDVHDGKVVSTHEQVLR[2] | rat gingival epithelial cell | RgpB |
| 4 | TKVMDVHDGKVVSTHEQVLR + (O)[2] | rat gingival epithelial cell | RgpB |
| 5 | TIVEEVQDGKVISSREQVHQTTR[3] | rat gingival epithelial cell | RgpB/HRgpA |
| 6 | RTAAENEFVTLK[4] | human Keratin 6 | Kgp |

TABLE 5-continued

| | | | |
|---|---|---|---|
| 7 | AQYEEIAQRSRAEAESWYQTK[5] | human Keratin 6 | Kgp |
| 8 | TKFETEQALR[6] | human Keratin 17 | RgpB |
| 9 | DQYEKMAEKNR[7] | human Keratin 17 | RgpB |
| 10 | TIVEEVQDGKVISSR[8] | human Keratin 17 | RgpB |
| 11 | QFTSSSSIKGSSGLGGGSSR[9] | human Keratin 17 | RgpB |
| 12 | EVATNSELVQSGKSEISELR[10] | human Keratin 17 | RgpB |

| peptide No. | Homology search results[SEQ ID NO] Keratin 14 | | |
|---|---|---|---|
| | human | rat | mouse |
| 1 | | | |
| 2 | | | |
| 3 | TKVMDVHDGKVVSTHEQVLR[2] | TKVMDVHDGKVVSTHEQVLR[2] | TKVMDVHVGKVVSTHEQVLR[2] |
| 4 | | | |
| 5 | | | |
| 6 | | | |
| 7 | | | |
| 8 | TKYETELNLR[23] | TKFETEQSLR[24] | TKFETEQSLR[24] |
| 9 | DQYEKMAEKNR[7] | DQYEKMAEKNR[7] | DQYEKMAEKNR[7] |
| 10 | | | |
| 11 | QFTSSSSMKGSCGIGGGIGGGSSR[25] | QFTSSSSMKGSCGIGGGSSR[26] | QFTSSSSMKGSCGIGGGSSR[26] |
| 12 | EVATNSELVQSGKSEISELR[10] | EVATNSELVQSGKSEISELR[10] | EVATNSELVQSGKSEISELR[10] |

TABLE 6

| peptide No. | identified sequence [SEQ ID NO] | substrate | enzyme | Homology search results[SEQ ID NO] Keratin 17 human |
|---|---|---|---|---|
| 1 | YEELQITAGRHGDDLRNTK[1] | rat gingival epithelial cell | Kgp | |
| 2 | YEELQQTAGRHGDDLRNTK[15] | rat gingival epithelial cell | Kgp | |
| 3 | TKVMDVHDGKVVSTHEQVLR[2] | rat gingival epithelial cell | RgpB | |
| 4 | TKVMDVHDGKVVSTHEQVLR + (O)[2] | rat gingival epithelial cell | RgpB | |
| 5 | TIVEEVQDGKVISSREQVHQTTR[3] | rat gingival epithelial cell | RgpB/HRgpA | TIVEEVQDGKVISS-REQVHQTTR[3] |
| 6 | RTAAENEFVTLK[4] | human Keratin 6 | Kgp | |
| 7 | AQYEEIAQRSRAEAESWYQTK[5] | human Keratin 6 | Kgp | |
| 8 | TKFETEQALR[6] | human Keratin 17 | RgpB | TKFETEQALR[6] |
| 9 | DQYEKMAEKNR[7] | human Keratin 17 | RgpB | DQYEKMAEKNR[7] |
| 10 | TIVEEVQDGKVISSR[8] | human Keratin 17 | RgpB | TIVEEVQDGKVISSR[8] |
| 11 | QFTSSSSIKGSSGLGGGSSR[9] | human Keratin 17 | RgpB | QFTSSSSIKGSSGLGGGSSR[9] |
| 12 | EVATNSELVQSGKSEISELR[10] | human Keratin 17 | RgpB | EVATNSELVQSGKSEISELR[10] |

| peptide No. | Homology search results[SEQ ID NO] Keratin 17 | | | |
|---|---|---|---|---|
| | chimpanzee | bovine | rat | mouse |
| 1 | | | | |
| 2 | | | | |
| 3 | | | | |
| 4 | | | | |
| 5 | TIVEEVQDGKVISSREQVHQTTR[3] | TIVEEVQDGRVISSREQVHQTSH[27] | TIVEEVQDGKVISS-REQVHQTTR[3] | TIVEEVQDGKVISS-REQVHQTTR[3] |
| 6 | | | | |
| 7 | | | | |
| 8 | TKFETEQALR[6] | TKFETEQALR[6] | TKFETEQALR[6] | TKFETEQALR[6] |
| 9 | DQYEKMAEKNR[7] | DQYEKMAEKNR[7] | DQYEKMAEKNR[7] | DQYEKMAEKNR[7] |
| 10 | TIVEEVQDGKVISSR[8] | TIVEEVQDGKVISSR[28] | TIVEEVQDGKVISSR[8] | TIVEEVQDGKVISSR[8] |
| 11 | QFTSSSSIKGSSGLGGGSSR[9] | RHFSSGSIKGSSGLAGGSSR[29] | QFTSSSIKGSSGLGGGSSR[9] | QFTSSSSIKGSSGLGGGSSR[9] |
| 12 | EVATNSELVQSGKSEISELR[30] | EVATNSELVQSGKSEISELR[10] | EVATNSELVQSGKSEISELR[10] | EVATNSELVQSGKSEISELR[10] |

Example 3

On Spot Profiling and Identification of Periodontal Bacterial Enzymatic Degradation Product of Keratin To identify further periodontal bacterial enzymatic degradation product derived from keratin, on spot profiling was performed. Human Keratin 6 and Keratin 17 were treated with purified gingipain (Kgp for Keratin 6, RgpB for Keratin 17) in the same manner as in Example 1, and profiling of the enzymatic degradation product was performed by mass spectrometry in the same manner as in Example 1. The results are shown in FIG. 2. Besides peptide 1 identified in Example 2 (Kgp degradation product of Keratin 6) and peptide 5 (RgpB/HRgpA degradation product of Keratin 17), plural peaks of degradation products were detected.

In the same manner as in Example 2, the detected peaks were identified. As a result, peptides consisting of the amino acid sequences shown by SEQ ID NOs: 4 and 5 (peptides 6 and 7) were newly identified as Kgp degradation products of human Keratin 6, and peptides consisting of the amino acid sequences shown by SEQ ID NOs: 6-10 (peptides 8-12) were newly identified as RgpB degradation products of human Keratin 17 (FIG. 3). Furthermore, the results of homology search of ortholog and paralog of other mammals are shown in Tables 3-6. The amino acid sequences of the regions corresponding to peptides 6-12 were well conserved between mammals.

Example 4

Figure 4:
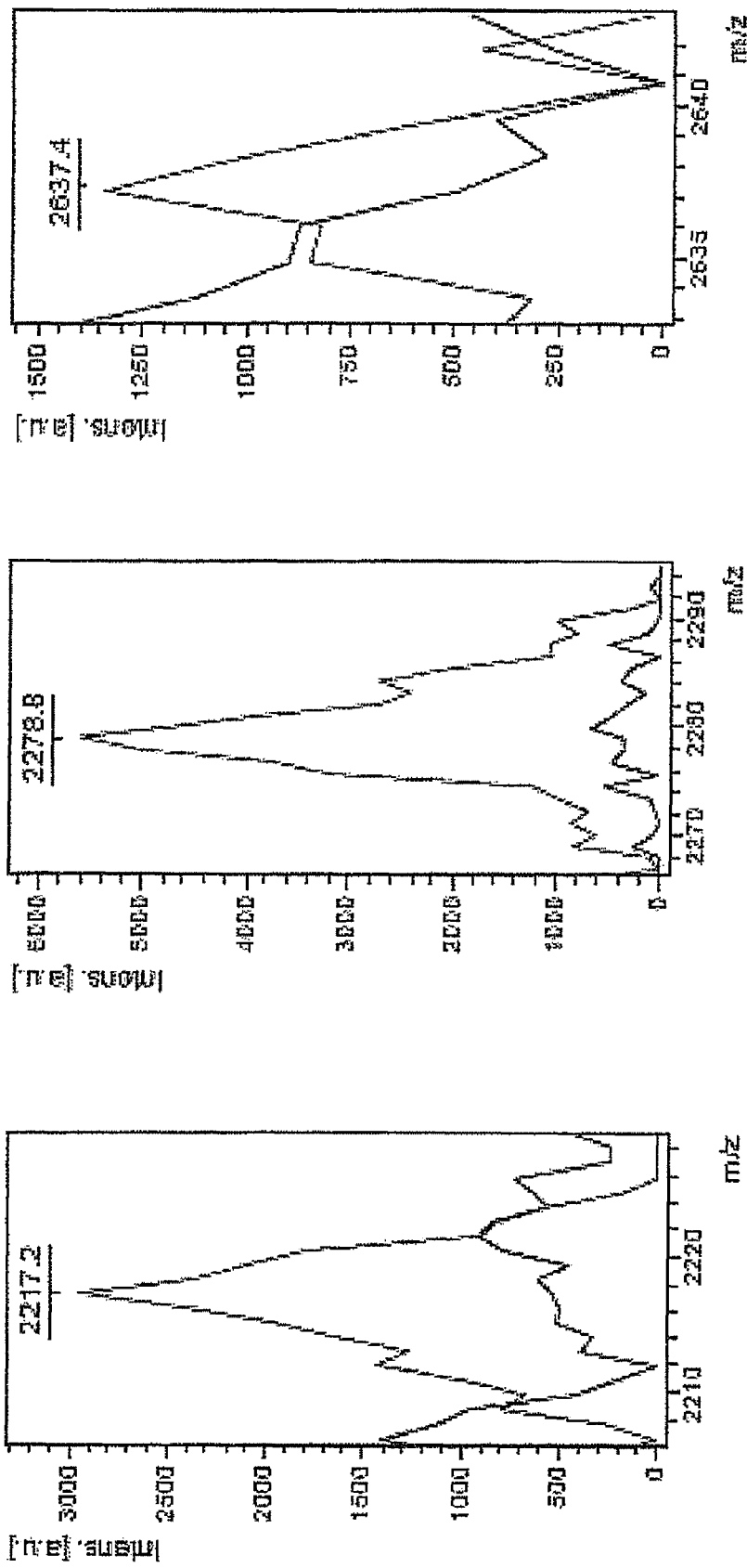
FIG. 4 shows the presence of peptides 1, 3 and 5 in dental plaque of periodontitis patients, wherein the vertical axis shows relative peak intensity and the horizontal axis shows m/z values. (P) periodontitis patients; (c) control (healthy subjects)

Confirmation of Presence of Biomarker in Interdental Liquid of Periodontal Disease Patients Sterile paper points were inserted into the gingival sulcus of periodontitis patients and healthy subjects for 5 min, and this procedure was repeated three times to collect interdental liquid. These paper points were immersed in saline to prepare interdental liquid samples. These interdental liquid samples were subjected to differential profiling in the same manner as in Example 1. The results are shown in FIG. 4. Clear peaks corresponding to peptides 1, 3 and 5 were detected in periodontitis patients, but otherwise in healthy subjects. The present Example has revealed that keratin degradation due to periodontal bacterial enzyme actually occurs in periodontal disease patients, and therefore, the keratin degradation products are useful as biomarkers of periodontal disease.

Example 5

Figure 5:
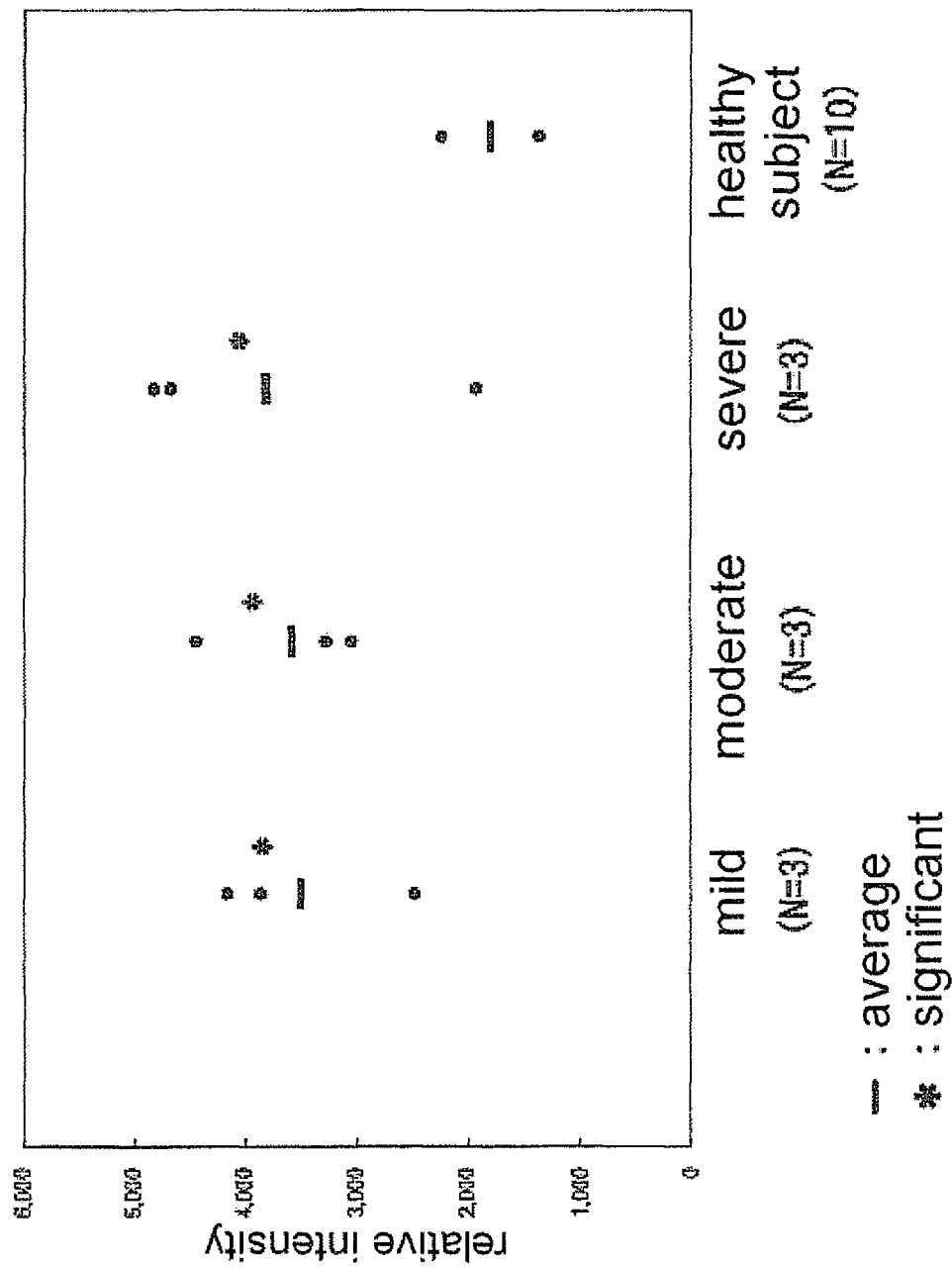
FIG. 5 shows the peptide 3 levels in the blood from periodontal disease patients with different severity, wherein the vertical axis shows relative peak intensity.

Confirmation of Presence of Biomarker in Serum of Periodontal Disease Patients Serum samples obtained from periodontal disease patients with different symptoms (mild, moderate and severe, 3 patients each) and healthy subjects (10 people) were subjected to differential profiling in the same manner as in Example 1, and the presence of keratin degradation products in blood was verified. As a result, peptide 3 was detected at significantly high levels in the sera of the periodontal disease patients regardless of symptom levels as compared to healthy subjects (FIG. 5). In addition, the patients with severe symptoms tended to show somewhat higher blood levels. The above-mentioned results have revealed that keratin degradation products are useful not only as biomarkers in an interdental liquid (dental plaque) but also in blood of periodontal disease.

Example 6

Figure 6:
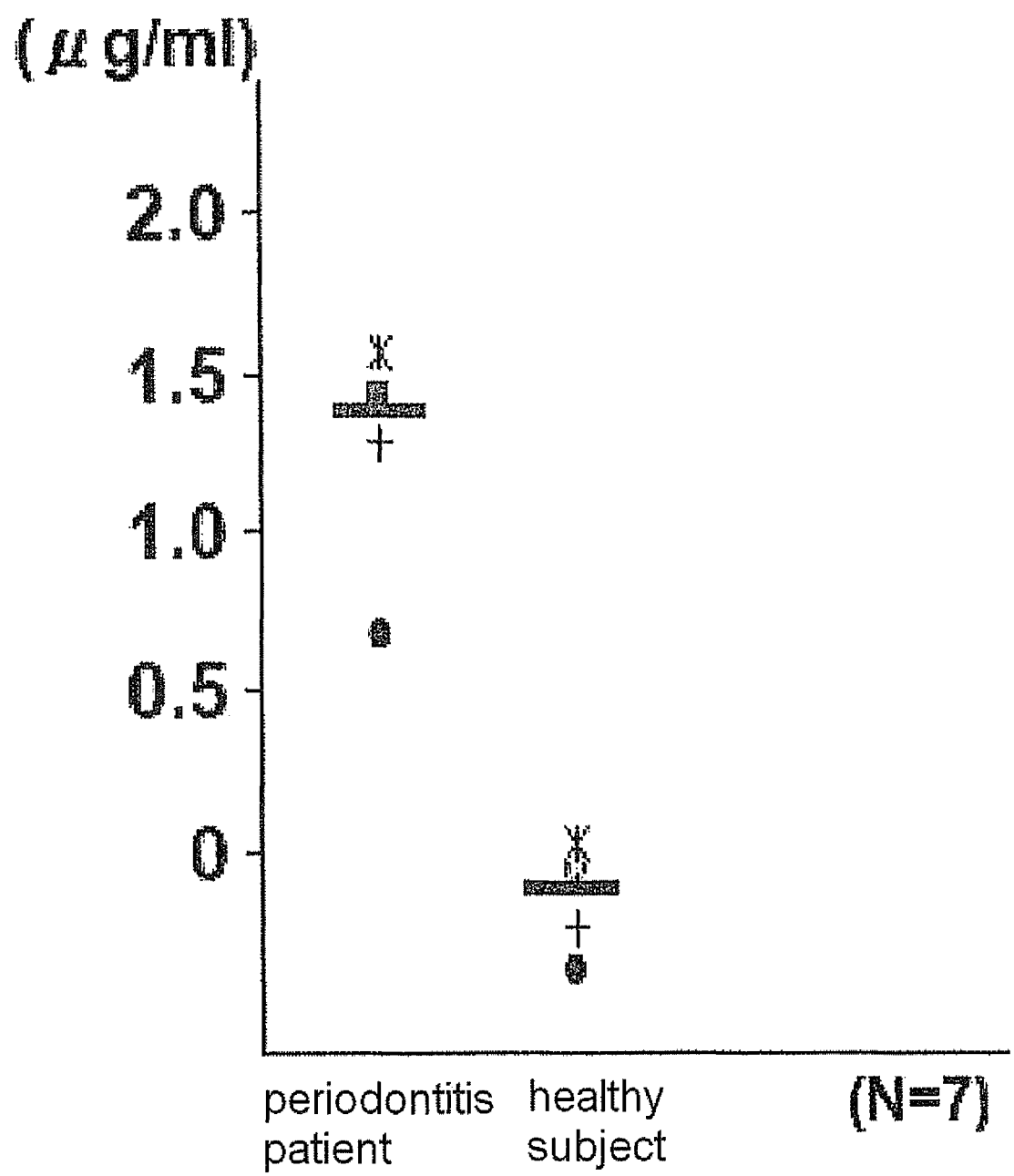
FIG. 6 shows the results of quantification, by the ELISA method, of peptide 1 in the plasma of periodontal disease patients (left) and healthy subjects.

Confirmation of Presence of Biomarker in Plasma of Periodontal Disease Patients by ELISA A monoclonal antibody to peptide 1 (Kgp degradation product of Keratin 6) was produced according to a conventional method, and the presence of the peptide in the plasma of periodontal disease patients and healthy subjects by ELISA method. The results are shown in FIG. 6. In the plasma derived from healthy subjects, peptide 1 was undetectable, whereas the peptide was detected in the plasma derived from the periodontitis patients. That is, it was shown that keratin is decomposed by periodontal bacterial enzymes to injure the gingival epithelial tissues of the patients, and the generated keratin degradation product penetrates into the blood from the gingival sulcus.

Example 7

T Cell Stimulation by Full-length Keratin and Fragment Thereof

Lymphocytes obtained from periodontitis patients and healthy subjects were subjected to a drug-induced lymphocyte stimulation test (DLST) using full-length human Keratin 6 and peptide 1 (fragment thereof) (periodontitis patients: N=22, healthy subjects: N=5). As a result, full-length human Keratin 6 and peptide 1 showed remarkable T cell proliferation induction potency in periodontitis patients as compared to healthy subjects (Table 7). This suggests involvement of autoimmune response to the degraded product of Keratin, which intravasated into the circulation, in the periodontal diseases.

TABLE 7

|  | Full-length human Keratin 6 | Peptide 1 | Scramble peptide |
|---|---|---|---|
| Periodontitis patients | 13/22 | 3/22 | 0/22 |
| Healthy subject | 2/5 | 0/5 | 0/5 |

Example 8

Figure 7:
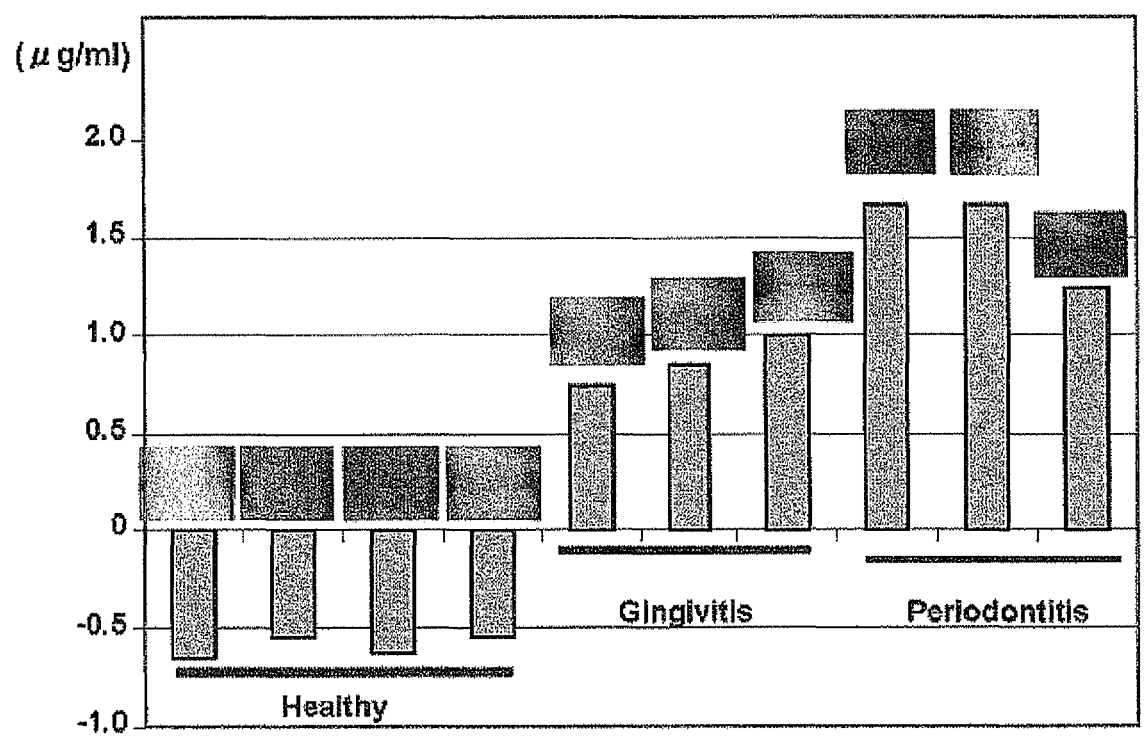
FIG. 7 shows the measurement results of peptide 1 and anti-human Keratin 6 autoantibody in the sera of gingivitis patients (Gingivitis), periodontitis patients (Periodontitis) and healthy subjects (Healthy), wherein the graph vertical axis shows peptide 1 concentration and the upper panel of the bar graph is a photograph of the band of anti-human Keratin 6 autoantibody by Western blotting.

Confirmation of Presence of Keratin 6 Degradation Product and Anti-Human Keratin 6 Autoantibody in Sera of Periodontal Disease Patients To verify the involvement of autoimmune responses to keratin degradation products in periodontal diseases, the presence of peptide 1 (fragment of Keratin 6) and autoantibody thereto in the sera of gingivitis and periodontitis patients was examined. Peptide 1 was detected by ELISA method using an anti-human peptide 1 monoclonal antibody, and anti-human Keratin 6 autoantibody was detected by Western blotting using full-length human Keratin 6 protein. The results are shown in FIG. 7. Peptide 1 and anti-human Keratin 6 autoantibody were not detected in any healthy subject sera, whereas peptide 1 and anti-human Keratin 6 autoantibody were detected in all sera derived from gingivitis and periodontitis patients. In addition, blood peptide level and blood autoantibody level tended to be higher in periodontitis patients with high severity.

Example 9

Increased Expression of RANKL in Lymphocytes of Periodontal Disease Patients

Figure 8:
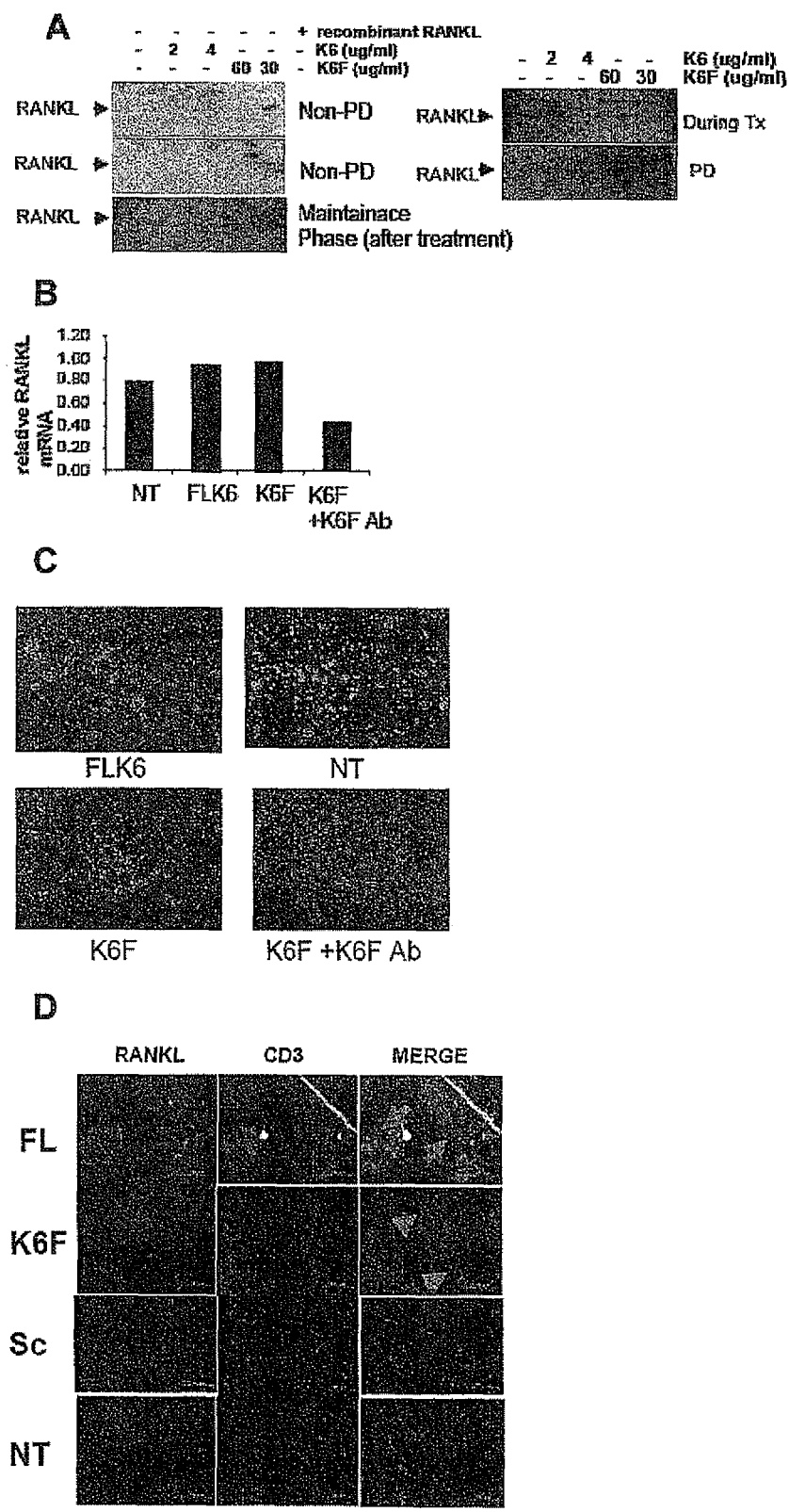
FIG. 8A shows expression of RANKL protein in lymphocytes derived from periodontitis patients who are untreated (PD), during treatment (During Tx) and after treatment (Maintenance Phase), and healthy subjects (Non-PD), when stimulated with FLK6 or K6F. B shows expression of RANKL mRNA in lymphocytes derived from periodontitis patients, wherein NT means untreated. C shows lymphoblast formation in lymphocytes derived from periodontitis patients. D shows immunostaining of peripheral blood mononuclear cells derived from periodontitis patients with RANKL and CD3.

Blood samples were collected from progressive (untreated) periodontitis patients, periodontitis patients during treatment and periodontitis patients after treatment to obtain lymphocytes, stimulated with full-length human Keratin 6 (K6; 2 or 4 µg/ml) or peptide 1 (K6F; 60 or 30 µg/ml), expression of RANKL in lymphocytes was examined by Western blot analysis using anti RANKL antibody. As a result, RANKL was not expressed in lymphocytes of healthy subject (Non-PD) and periodontitis patients after treatment (Maintenance Phase), and increased expression of RANKL was observed in the lymphocytes of untreated periodontitis patients and periodontitis patients during treatment (FIG. 8A). In addition, RT-PCR of RNA derived from the lymphocytes of periodontitis patients showed that expression of RANKL mRNA tended to increase by the stimulation with full-length human Keratin 6 (FLK6) or peptide 1 (K6F) and, in the co-presence of anti-peptide 1 antibody (K6F+K6F Ab), expression of RANKL mRNA was remarkably suppressed (FIG. 8B). Fluorescent staining was performed to examine induction of lymphoblast formation by the stimulation with full-length human Keratin 6 or peptide 1. As a result, it was correlated well with the expression of RANKL mRNA (FIG. 8C).

Peripheral blood monocytes derived from severe periodontitis patients were stimulated with full-length human Keratin 6 (FL) or peptide 1 (K6F), and immunostained with anti-RANKL antibody and anti-CD3 antibody. As a result, dut to the stimulation with FL or K6F, CD positive cells (T cells) that express RANKL remarkably increased (FIG. 8D). Stimulation with scramble peptide did not increase RANKL expressing T cells.

Example 10

Differentiative Induction to Osteoclast in Sera of Periodontal Disease Patients by Stimulation With Keratin or Periodontal Bacterial Enzymatic Degradation Product Thereof T cells obtained from peripheral blood of the periodontal disease patients and healthy subject were stimulated with full-length human Keratin 6 (FL) or peptide 1 (K6F), and differentiation into polynuclear giant cells was observed by tissue staining. As a result, remarkable differentiation into polynuclear giant cells was observed in periodontal disease patients by the stimulation with FL or K6F. Addition of OPG-Fc (RANKL inhibitor) remarkably suppressed the differentiation into polynuclear giant cells (FIG. 9A). In addition, as a result of a pit formation assay, formation of a marked bone resorption pit due to the stimulation with FL or K6F was observed in dentin section (FIG. 9B). The above results strongly suggest that induced expression of RANKL due to the stimulation with FL or K6F induces differentiation into osteoclast-like polynuclear giant cells via RANKL/RANK signal, and enhances bone resorption.

Example 11

Figure 10:
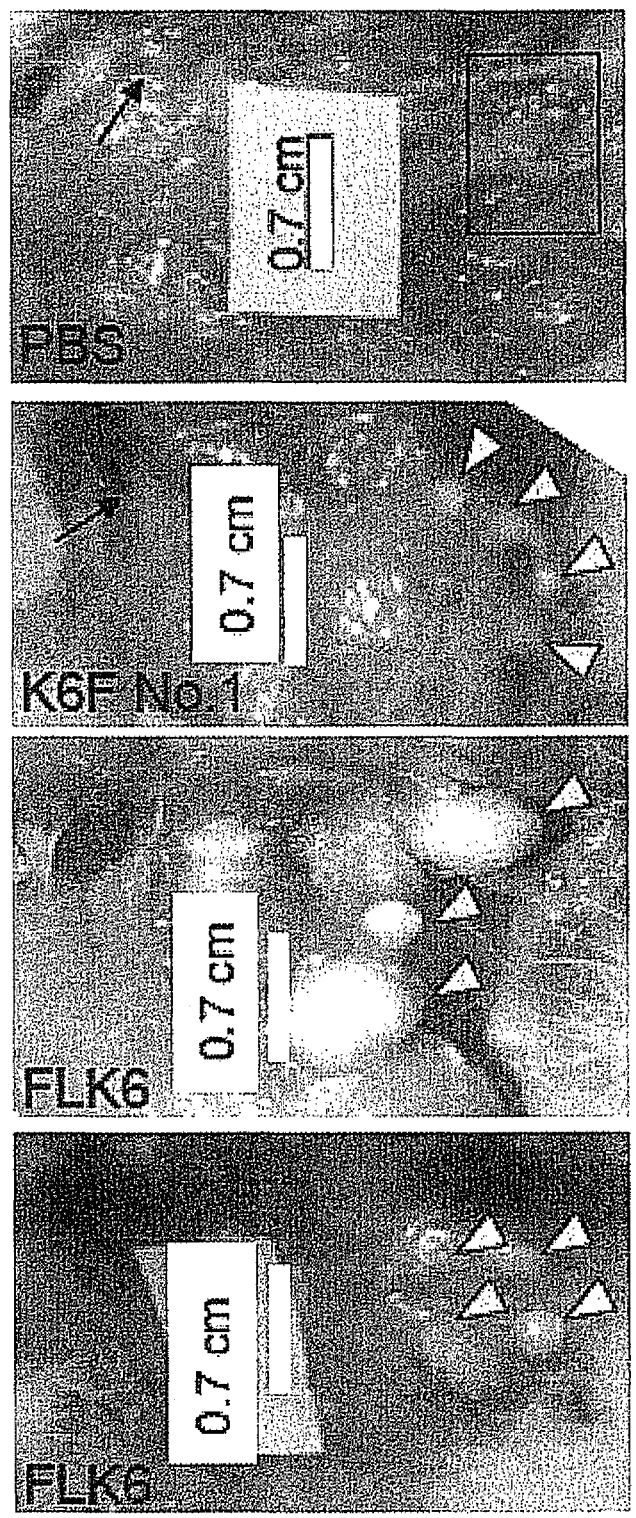
FIG. 10 shows tumentia of the lower jaw lymph node on the left side and the right side of the rats intragingivally injected with PBS, K6F or FLK6 into the left lower jaw.
Figure 11:
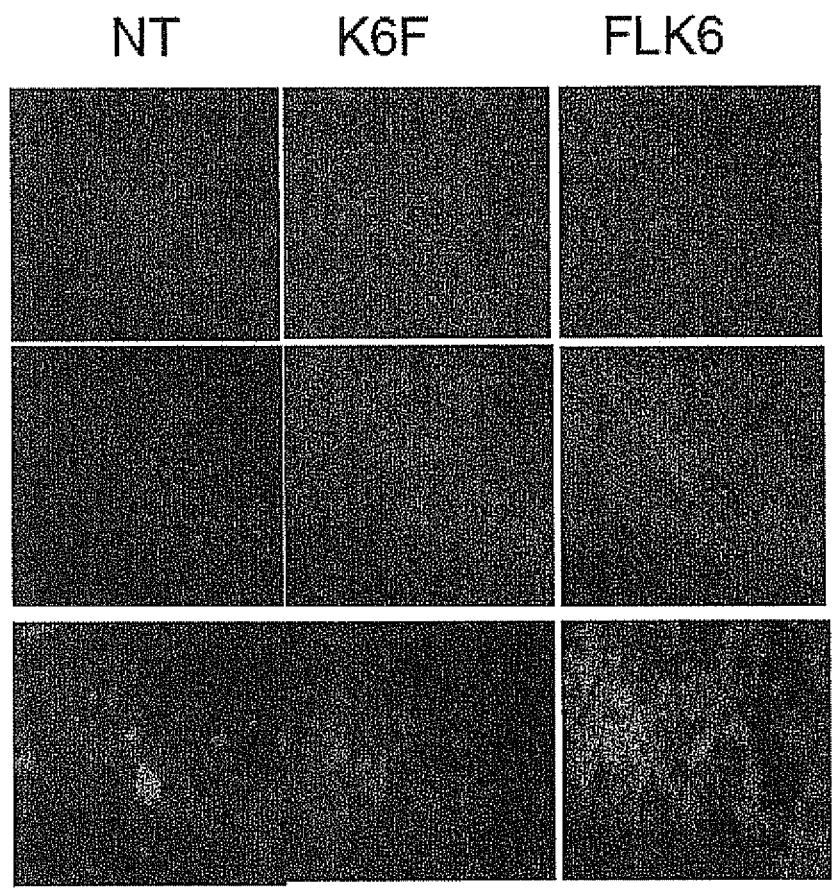
FIG. 11 shows lymphoblast formation in the lymphocytes of the rats injected with PBS (top), K6F (middle) or FLK6 (lower). Untreated, K6F-stimulated and FLK6-stimulated lymphocytes are shown from the left.
Figure 12:
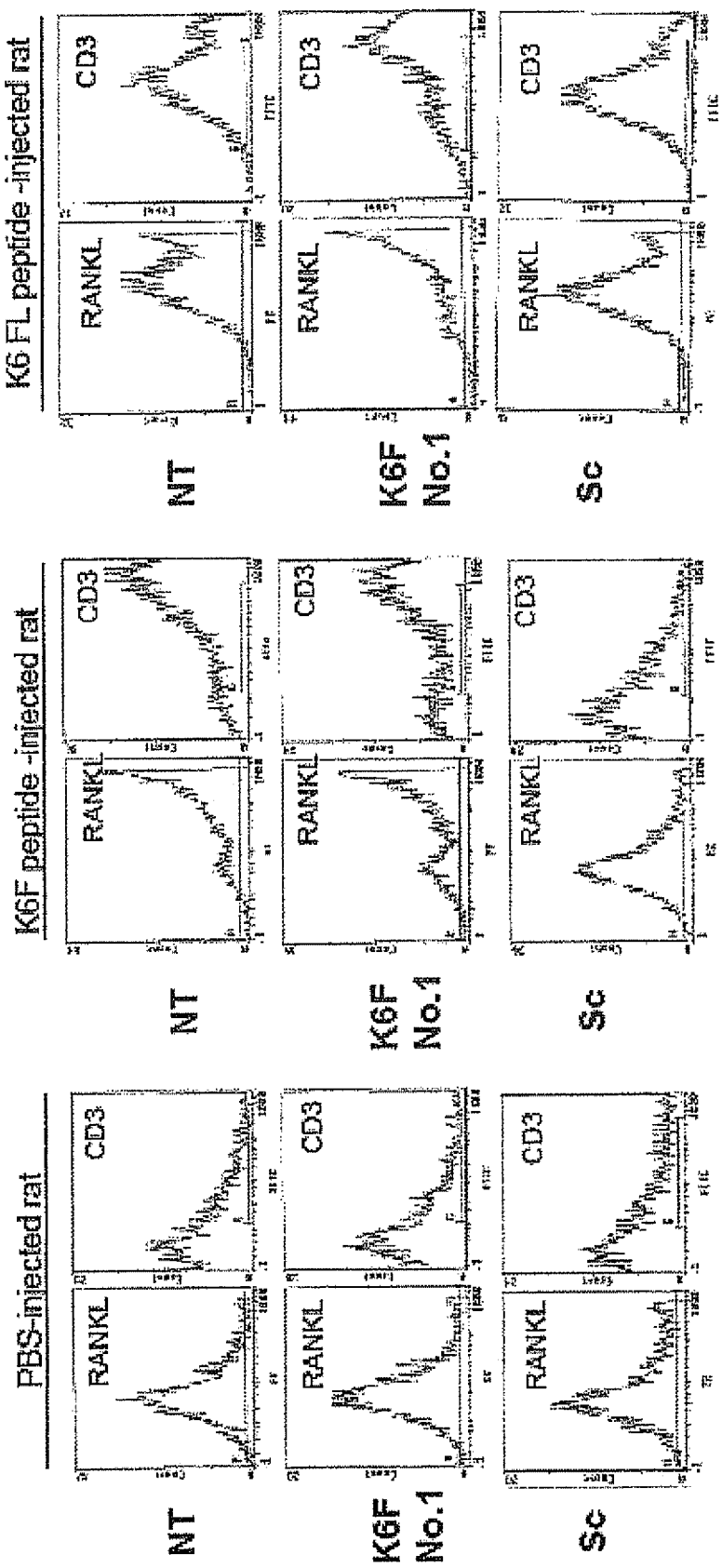
FIG. 12 shows expression of RANKL and CD3 in peripheral blood mononuclear leukocytes derived from the rats injected with PBS, K6F or FLK6, wherein NT means untreated, and Sc means scramble peptide-stimulated peripheral blood mononuclear leukocytes.
Figure 13:
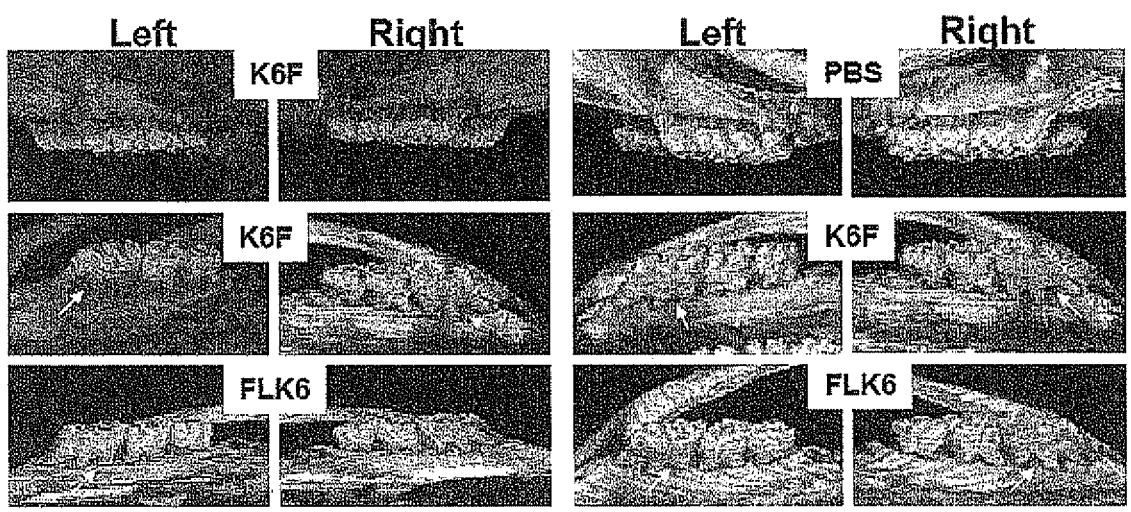
FIG. 13 shows the form of the teeth on the left side and the right side of the rats injected with PBS, K6F or FLK6.

Effect of Immunization of Rat with Keratin or Periodontal Bacterial Enzymatic Degradation Product Thereof PBS, full-length human Keratin 6 (FLK6) or peptide 1 (K6F) was administered by intragingival injection to the lower left jaw of rats. The rats injected with FLK6 or K6F showed tumentia of lower jaw lymph node (Lt), whereas the rats injected with PBS showed no change. No rat showed tumentia of lower jaw lymph node on the right side (Rt) which was free of injection (FIG. 10). The lymphocytes obtained from these rats were stimulated with FLK6 or K6F and cultured. Lymphoblast formation was observed in the lymphocytes of rats injected with FLK6 or K6F, and stimulation with FLK6 or K6F further enhanced lymphoblast formation (FIG. 11). In addition, peripheral blood mononuclear leukocytes were obtained from these rats, stimulated with K6F or scramble peptide (Sc), and expression of RANKL and CD3 were examined by FACS analysis. As a result, the rats injected with FL6 or K6F showed enhanced expression of RANKL and CD3 by stimulation with K6F. However, stimulation with Sc did not induce expression thereof (FIG. 12). Moreover, alveolar bone destruction in these rats was examined. As a result, alveolar bone destruction was observed in the lower jaw of the rats injected with FLK6 or K6F (FIG. 13).

Example 12

Figure 14:
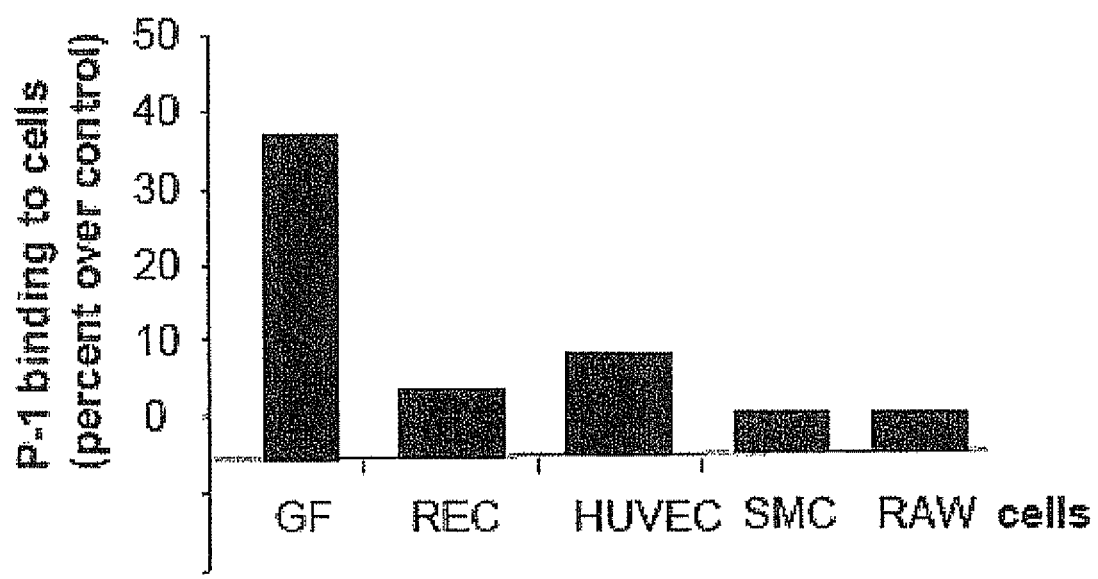
FIG. 14 shows the binding level of K6F(P-1) to various cells. The results show percentage of binding that exceeds the binding to the control cell.

Binding of Periodontal Bacterial Enzymatic Degradation Product of Keratin to Gingiva Fibroblast Various cells were stimulated with FITC-labeled peptide 1 (K6F, P-1), observed under a confocal microscope, and the binding level to K6F was shown by percentage higher than that of the control cell (FIG. 14). As a result, gingiva fibroblast (GF) showed far higher binding level to K6F as compared to other cells.

Example 13

Induced Expression of Various Cytokines and Activation of MAPK Pathway in Gingiva Fibroblast Due to Stimulation with Keratin Periodontal Bacterial Enzymatic Degradation Product Gingiva fibroblasts were stimulated with peptide 1 (K6F), recombinant Keratin 6 (RK6, Rec-K6) or scramble peptide (Sc) for 2-24 hr, and the expression levels of MMP-2, MMP-3, MCP-1, IL-6, IL-8 were measured by Western blot analysis. As a result, these cytokines and chemokines showed remarkably increased expression by the stimulation with K6F and were activated (FIG. 15 A-D). Then, gingiva fibroblast (GF) and gingival epithelial cell (GEC) were stimulated with peptide 1 (K6F) or scramble peptide (Sc), respectively, for 15 min-2 hr, and phosphorylation of p38 in GF, as well as expression of IκB-α and phosphorylation of p65 NFκB and activation of representative serine/threonine kinase in GEC were examined. As a result, K6F induced activation of p38 MAPK in GF, but did not induce degradation of IκB and activation of p65 NFκB (FIG. 16A). In addition, K6F induced activation of ERK and Akt in GEC (FIG. 16B).

The above results strongly suggest that keratin or a periodontal bacterial enzymatic degradation product thereof induces expression of various cytokines and chemokines in topical gingival tissues and develop inflammation and induce expression of RANKL in osteoblasts and the like, said keratin or a degradation product thereof that transferred into the blood stimulates growth of T cells and induces expression of RANKL on the cell surface, and these RANKL expressing cells act on RANK in osteoclast progenitor cells to induce differentiation into osteoclasts and enhance bone resorption, which causes destruction of alveolar bone, develops and aggravates periodontal diseases, and causes systemic complications.

INDUSTRIAL APPLICABILITY

Since a substance having affinity to keratin in gingival epithelium or a degradation product thereof and a substance having affinity to an autoantibody to said degradation product can suppress an autoimmune response caused by the degradation product, they are useful as agents for the prophylaxis or treatment of a periodontal disease and a systemic complication thereof. In addition, these substances are also useful as diagnostic reagents for periodontal diseases. Since a substance having affinity to keratin in gingival epithelium or a periodontal bacterial enzymatic degradation product thereof can also inhibit T cell proliferation and increased expression of RANKL in the cell due to the keratin or a degradation product thereof, it suppresses differentiation of osteoclast progenitor cell into osteoclast via RANKL/RANK signal and inhibits bone resorption. Therefore, it is useful as an agent for the prophylaxis or treatment of a periodontal disease and a systemic complication thereof.

Moreover, since a periodontal bacterial enzyme has a keratin degrading activity, it is useful for removal of stratum corneum, prevention of wavy hair, removal of unwanted hair, enhancement of skin permeability of medicaments, deformation or discoloration of nail such as ingrown toenail and the like, treatment of *Trichophyton* infections such as tinea unguium, and the like.

Furthermore, a screening method using degradation of keratin as an index is useful for identification of a novel periodontal bacterium and search for a candidate substance of a therapeutic drug for a periodontal disease.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

The contents disclosed in any publication cited herein, including patents and patent applications, are hereby incorporated in their entireties by reference, to the extent that they have been disclosed herein.

This application is based on a patent application No. 2010-061673 filed in Japan (filing date: Mar. 17, 2010), the contents of which are incorporated in full herein.

The invention claimed is:

1. A method of detecting a peptide and/or autoantibodies to said peptide, wherein the peptide is selected from the group of peptides consisting of respective amino acid sequences shown by SEQ ID NOs: 1-3, 5 and 7-9 or orthologs and paralogs thereof as shown by SEQ ID NOs: 15-22 and 24-30 in a test animal, comprising:
   (1) obtaining a biological sample selected from the group consisting of blood, plasma, serum, interdental liquid, urine and saliva from the test animal;
   (2) measuring amounts of one or more peptides selected from the group of peptides consisting of respective amino acid sequences shown by SEQ ID NOs: 1-3, 5 and 7-9 or orthologs and paralogs thereof as shown by SEQ ID NOs: 15-22 and 24-30, and/or one or more autoantibodies selected from the group consisting of autoantibodies to respective peptides of said group of peptides, in the biological sample, wherein the amount(s) of the peptides and/or autoantibodies are measured by applying the biological sample to mass spectrometry, or by a method selected from enzyme-linked immunosorbent assay, radioimmunoassay, nephelometry and surface plasmon resonance.

2. A method for the diagnosis and treatment of a periodontal disease of a test animal, comprising:
   (1) obtaining a biological sample selected from the group consisting of blood, plasma, serum, interdental liquid, urine and saliva from the test animal;
   (2) measuring amounts of one or more peptides selected from the group of peptides consisting of respective amino acid sequences shown by SEQ ID NOs: 1-10 or orthologs and paralogs thereof as shown by SEQ ID NOs: 15-30, and/or one or more autoantibodies selected from the group consisting of autoantibodies to respective peptides of said group of peptides, in the biological sample, wherein the amount(s) of the peptides and/or autoantibodies are measured by applying the biological sample to mass spectrometry, or by a method selected from enzyme-linked immunosorbent assay, radioimmunoassay, nephelometry and surface plasmon resonance;
   (3) diagnosing that the test animal has a high possibility of being affected with a periodontal disease when the amount(s) of the peptides and/or autoantibodies in the biological sample significantly increase as compared to those in a control sample obtained from a normal animal; and
   (4) administering an effective amount of any of the peptides to an oral cavity of the animal to trap and remove an autoantibody to the peptide.

3. A method for evaluating the improvement of the condition of a periodontal disease, comprising:
   (1) collecting biological samples selected from the group consisting of blood, plasma, serum, interdental liquid, urine and saliva from a patient in a chronological order;
   (2) measuring time course changes of an amount of one or more peptides selected from the group of peptides consisting of respective amino acid sequences shown by SEQ ID NOs: 1-10 or orthologs and paralogs thereof as shown by SEQ ID NOs: 15-30, and/or one or more autoantibodies selected from the group consisting of autoantibodies to respective peptides of said group of peptides in the samples; and
   (3) determining that the condition of the periodontal disease in the patient is improved when the amount(s) of the peptides and/or autoantibodies decrease over time,
      wherein the patient is treated by administering an effective amount of any of the peptides to an oral cavity of the patient to trap and remove an autoantibody to the peptide.

4. The method according to claim 3, further comprising treating the patient between a sampling and the next sampling, and evaluating the treatment effect in the patient by comparing changes of amounts of the peptides and/or autoantibodies in biological samples obtained from said patient before and after the treatment.

* * * * *

SEQUENCE LISTING

```
<160> NUMBER OF SEQ ID NOS: 30

<210> SEQ ID NO 1
<211> LENGTH: 19
<212> TYPE: PRT
<213> ORGANISM: Homo sapiens

<400> SEQUENCE: 1

Tyr Glu Glu Leu Gln Ile Thr Ala Gly Arg His Gly Asp Asp Leu Arg
1               5                   10                  15

Asn Thr Lys

<210> SEQ ID NO 2
<211> LENGTH: 20
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Methionine residue may be oxidized.

<400> SEQUENCE: 2

Thr Lys Val Met Asp Val His Asp Gly Lys Val Val Ser Thr His Glu
1               5                   10                  15

Gln Val Leu Arg
            20

<210> SEQ ID NO 3
<211> LENGTH: 23
<212> TYPE: PRT
<213> ORGANISM: Homo sapiens

<400> SEQUENCE: 3
```

Thr Ile Val Glu Glu Val Gln Asp Gly Lys Val Ile Ser Ser Arg Glu
1               5                   10                  15

Gln Val His Gln Thr Thr Arg
            20

<210> SEQ ID NO 4
<211> LENGTH: 12
<212> TYPE: PRT
<213> ORGANISM: Homo sapiens

<400> SEQUENCE: 4

Arg Thr Ala Ala Glu Asn Glu Phe Val Thr Leu Lys
1               5                   10

<210> SEQ ID NO 5
<211> LENGTH: 21
<212> TYPE: PRT
<213> ORGANISM: Homo sapiens

<400> SEQUENCE: 5

Ala Gln Tyr Glu Glu Ile Ala Gln Arg Ser Arg Ala Glu Ala Glu Ser
1               5                   10                  15

Trp Tyr Gln Thr Lys
            20

<210> SEQ ID NO 6
<211> LENGTH: 10
<212> TYPE: PRT
<213> ORGANISM: Homo sapiens

<400> SEQUENCE: 6

Thr Lys Phe Glu Thr Glu Gln Ala Leu Arg
1               5                   10

<210> SEQ ID NO 7
<211> LENGTH: 11
<212> TYPE: PRT
<213> ORGANISM: Homo sapiens

<400> SEQUENCE: 7

Asp Gln Tyr Glu Lys Met Ala Glu Lys Asn Arg
1               5                   10

<210> SEQ ID NO 8
<211> LENGTH: 15
<212> TYPE: PRT
<213> ORGANISM: Homo sapiens

<400> SEQUENCE: 8

Thr Ile Val Glu Glu Val Gln Asp Gly Lys Val Ile Ser Ser Arg
1               5                   10                  15

<210> SEQ ID NO 9
<211> LENGTH: 20
<212> TYPE: PRT
<213> ORGANISM: Homo sapiens

<400> SEQUENCE: 9

Gln Phe Thr Ser Ser Ser Ser Ile Lys Gly Ser Ser Gly Leu Gly Gly
1               5                   10                  15

Gly Ser Ser Arg
            20

```
<210> SEQ ID NO 10
<211> LENGTH: 20
<212> TYPE: PRT
<213> ORGANISM: Homo sapiens

<400> SEQUENCE: 10

Glu Val Ala Thr Asn Ser Glu Leu Val Gln Ser Gly Lys Ser Glu Ile
1               5                   10                  15

Ser Glu Leu Arg
            20

<210> SEQ ID NO 11
<211> LENGTH: 564
<212> TYPE: PRT
<213> ORGANISM: Homo sapiens

<400> SEQUENCE: 11

Met Ala Ser Thr Ser Thr Thr Ile Arg Ser His Ser Ser Arg Arg
1               5                   10                  15

Gly Phe Ser Ala Asn Ser Ala Arg Leu Pro Gly Val Ser Arg Ser Gly
                20                  25                  30

Phe Ser Ser Ile Ser Val Ser Arg Ser Arg Gly Ser Gly Gly Leu Gly
                35                  40                  45

Gly Ala Cys Gly Gly Ala Gly Phe Gly Ser Arg Ser Leu Tyr Gly Leu
    50                  55                  60

Gly Gly Ser Lys Arg Ile Ser Ile Gly Gly Gly Ser Cys Ala Ile Ser
65                  70                  75                  80

Gly Gly Tyr Gly Ser Arg Ala Gly Gly Ser Tyr Gly Phe Gly Gly Ala
                85                  90                  95

Gly Ser Gly Phe Gly Phe Gly Gly Gly Ala Gly Ile Gly Phe Gly Leu
                100                 105                 110

Gly Gly Gly Ala Gly Leu Ala Gly Gly Phe Gly Gly Pro Gly Phe Pro
            115                 120                 125

Val Cys Pro Pro Gly Gly Ile Gln Glu Val Thr Val Asn Gln Ser Leu
130                 135                 140

Leu Thr Pro Leu Asn Leu Gln Ile Asp Pro Ala Ile Gln Arg Val Arg
145                 150                 155                 160

Ala Glu Glu Arg Glu Gln Ile Lys Thr Leu Asn Asn Lys Phe Ala Ser
                165                 170                 175

Phe Ile Asp Lys Val Arg Phe Leu Glu Gln Gln Asn Lys Val Leu Asp
                180                 185                 190

Thr Lys Trp Thr Leu Leu Gln Glu Gln Gly Thr Lys Thr Val Arg Gln
            195                 200                 205

Asn Leu Glu Pro Leu Phe Glu Gln Tyr Ile Asn Asn Leu Arg Arg Gln
    210                 215                 220

Leu Asp Asn Ile Val Gly Glu Arg Gly Arg Leu Asp Ser Glu Leu Arg
225                 230                 235                 240

Asn Met Gln Asp Leu Val Glu Asp Leu Lys Asn Lys Tyr Glu Asp Glu
                245                 250                 255

Ile Asn Lys Arg Thr Ala Ala Glu Asn Glu Phe Val Thr Leu Lys Lys
                260                 265                 270

Asp Val Asp Ala Ala Tyr Met Asn Lys Val Glu Leu Gln Ala Lys Ala
            275                 280                 285

Asp Thr Leu Thr Asp Glu Ile Asn Phe Leu Arg Ala Leu Tyr Asp Ala
    290                 295                 300

Glu Leu Ser Gln Met Gln Thr His Ile Ser Asp Thr Ser Val Val Leu
```

```
                305                 310                 315                 320
        Ser Met Asp Asn Asn Arg Asn Leu Asp Leu Asp Ser Ile Ile Ala Glu
                        325                 330                 335

Val Lys Ala Gln Tyr Glu Glu Ile Ala Gln Arg Ser Arg Ala Glu Ala
                        340                 345                 350

Glu Ser Trp Tyr Gln Thr Lys Tyr Glu Glu Leu Gln Ile Thr Ala Gly
                        355                 360                 365

Arg His Gly Asp Asp Leu Arg Asn Thr Lys Gln Glu Ile Ala Glu Ile
                        370                 375                 380

Asn Arg Met Ile Gln Arg Leu Arg Ser Glu Ile Asp His Val Lys Lys
        385                 390                 395                 400

Gln Cys Ala Asn Leu Gln Ala Ala Ile Ala Asp Ala Glu Gln Arg Gly
                        405                 410                 415

Glu Met Ala Leu Lys Asp Ala Lys Asn Lys Leu Glu Gly Leu Glu Asp
                        420                 425                 430

Ala Leu Gln Lys Ala Lys Gln Asp Leu Ala Arg Leu Leu Lys Glu Tyr
                        435                 440                 445

Gln Glu Leu Met Asn Val Lys Leu Ala Leu Asp Val Glu Ile Ala Thr
                        450                 455                 460

Tyr Arg Lys Leu Leu Glu Gly Glu Glu Cys Arg Leu Asn Gly Glu Gly
        465                 470                 475                 480

Val Gly Gln Val Asn Ile Ser Val Val Gln Ser Thr Val Ser Ser Gly
                        485                 490                 495

Tyr Gly Gly Ala Ser Gly Val Gly Ser Gly Leu Gly Leu Gly Gly Gly
                        500                 505                 510

Ser Ser Tyr Ser Tyr Gly Ser Gly Leu Gly Val Gly Gly Gly Phe Ser
                        515                 520                 525

Ser Ser Ser Gly Arg Ala Thr Gly Gly Gly Leu Ser Ser Val Gly Gly
                        530                 535                 540

Gly Ser Ser Thr Ile Lys Tyr Thr Thr Thr Ser Ser Ser Ser Arg Lys
        545                 550                 555                 560

Ser Tyr Lys His

<210> SEQ ID NO 12
<211> LENGTH: 590
<212> TYPE: PRT
<213> ORGANISM: Homo sapiens

<400> SEQUENCE: 12

Met Ser Arg Gln Ser Ser Val Ser Phe Arg Ser Gly Gly Ser Arg Ser
        1               5                   10                  15

Phe Ser Thr Ala Ser Ala Ile Thr Pro Ser Val Ser Arg Thr Ser Phe
                        20                  25                  30

Thr Ser Val Ser Arg Ser Gly Gly Gly Gly Gly Gly Phe Gly Arg
                        35                  40                  45

Val Ser Leu Ala Gly Ala Cys Gly Val Gly Gly Tyr Gly Ser Arg Ser
                50                  55                  60

Leu Tyr Asn Leu Gly Gly Ser Lys Arg Ile Ser Ile Ser Thr Ser Gly
        65                  70                  75                  80

Gly Ser Phe Arg Asn Arg Phe Gly Ala Gly Ala Gly Gly Gly Tyr Gly
                        85                  90                  95

Phe Gly Gly Gly Ala Gly Ser Gly Phe Gly Phe Gly Gly Gly Ala Gly
                        100                 105                 110

Gly Gly Phe Gly Leu Gly Gly Gly Ala Gly Phe Gly Gly Gly Phe Gly
```

```
                115                 120                 125
Gly Pro Gly Phe Pro Val Cys Pro Pro Gly Ile Gln Glu Val Thr
            130                 135                 140
Val Asn Gln Ser Leu Leu Thr Pro Leu Asn Leu Gln Ile Asp Pro Ser
145                 150                 155                 160
Ile Gln Arg Val Arg Thr Glu Glu Arg Glu Gln Ile Lys Thr Leu Asn
                165                 170                 175
Asn Lys Phe Ala Ser Phe Ile Asp Lys Val Arg Phe Leu Glu Gln Gln
            180                 185                 190
Asn Lys Val Leu Asp Thr Lys Trp Thr Leu Leu Gln Glu Gln Gly Thr
        195                 200                 205
Lys Thr Val Arg Gln Asn Leu Glu Pro Leu Phe Glu Gln Tyr Ile Asn
    210                 215                 220
Asn Leu Arg Arg Gln Leu Asp Ser Ile Val Gly Glu Arg Gly Arg Leu
225                 230                 235                 240
Asp Ser Glu Leu Arg Asn Met Gln Asp Leu Val Glu Asp Phe Lys Asn
                245                 250                 255
Lys Tyr Glu Asp Glu Ile Asn Lys Arg Thr Thr Ala Glu Asn Glu Phe
            260                 265                 270
Val Met Leu Lys Lys Asp Val Asp Ala Ala Tyr Met Asn Lys Val Glu
        275                 280                 285
Leu Glu Ala Lys Val Asp Ala Leu Met Asp Glu Ile Asn Phe Met Lys
    290                 295                 300
Met Phe Phe Asp Ala Glu Leu Ser Gln Met Gln Thr His Val Ser Asp
305                 310                 315                 320
Thr Ser Val Val Leu Ser Met Asp Asn Asn Arg Asn Leu Asp Leu Asp
                325                 330                 335
Ser Ile Ile Ala Glu Val Lys Ala Gln Tyr Glu Glu Ile Ala Asn Arg
            340                 345                 350
Ser Arg Thr Glu Ala Glu Ser Trp Tyr Gln Thr Lys Tyr Glu Glu Leu
        355                 360                 365
Gln Gln Thr Ala Gly Arg His Gly Asp Asp Leu Arg Asn Thr Lys His
    370                 375                 380
Glu Ile Ser Glu Met Asn Arg Met Ile Gln Arg Leu Arg Ala Glu Ile
385                 390                 395                 400
Asp Asn Val Lys Lys Gln Cys Ala Asn Leu Gln Asn Ala Ile Ala Asp
                405                 410                 415
Ala Glu Gln Arg Gly Glu Leu Ala Leu Lys Asp Ala Arg Asn Lys Leu
            420                 425                 430
Ala Glu Leu Glu Glu Ala Leu Gln Lys Ala Lys Gln Asp Met Ala Arg
        435                 440                 445
Leu Leu Arg Glu Tyr Gln Glu Leu Met Asn Thr Lys Leu Ala Leu Asp
    450                 455                 460
Val Glu Ile Ala Thr Tyr Arg Lys Leu Leu Glu Gly Glu Glu Cys Arg
465                 470                 475                 480
Leu Ser Gly Glu Gly Val Gly Pro Val Asn Ile Ser Val Val Thr Ser
                485                 490                 495
Ser Val Ser Ser Gly Tyr Gly Ser Gly Ser Gly Tyr Gly Gly Gly Leu
            500                 505                 510
Gly Gly Gly Leu Gly Gly Gly Leu Gly Gly Gly Leu Ala Gly Gly Ser
        515                 520                 525
Ser Gly Ser Tyr Tyr Ser Ser Ser Ser Gly Gly Val Gly Leu Gly Gly
    530                 535                 540
```

Gly Leu Ser Val Gly Gly Ser Gly Phe Ser Ala Ser Ser Gly Arg Gly
545                 550                 555                 560

Leu Gly Val Gly Phe Gly Ser Gly Gly Gly Ser Ser Ser Val Lys
            565                 570                 575

Phe Val Ser Thr Thr Ser Ser Arg Lys Ser Phe Lys Ser
            580                 585                 590

<210> SEQ ID NO 13
<211> LENGTH: 472
<212> TYPE: PRT
<213> ORGANISM: Homo sapiens

<400> SEQUENCE: 13

Met Thr Thr Cys Ser Arg Gln Phe Thr Ser Ser Ser Met Lys Gly
1               5                   10                  15

Ser Cys Gly Ile Gly Gly Gly Ile Gly Gly Ser Ser Arg Ile Ser
            20                  25                  30

Ser Val Leu Ala Gly Gly Ser Cys Arg Ala Pro Ser Thr Tyr Gly Gly
            35                  40                  45

Gly Leu Ser Val Ser Ser Ser Arg Phe Ser Ser Gly Gly Ala Cys Gly
50                  55                  60

Leu Gly Gly Gly Tyr Gly Gly Phe Ser Ser Ser Ser Ser Ser Phe
65                  70                  75                  80

Gly Ser Gly Phe Gly Gly Tyr Gly Gly Leu Gly Ala Gly Leu
                85                  90                  95

Gly Gly Gly Phe Gly Gly Phe Ala Gly Gly Asp Gly Leu Leu Val
                100                 105                 110

Gly Ser Glu Lys Val Thr Met Gln Asn Leu Asn Asp Arg Leu Ala Ser
                115                 120                 125

Tyr Leu Asp Lys Val Arg Ala Leu Glu Glu Ala Asn Ala Asp Leu Glu
130                 135                 140

Val Lys Ile Arg Asp Trp Tyr Gln Arg Gln Arg Pro Ala Glu Ile Lys
145                 150                 155                 160

Asp Tyr Ser Pro Tyr Phe Lys Thr Ile Glu Asp Leu Arg Asn Lys Ile
                165                 170                 175

Leu Thr Ala Thr Val Asp Asn Ala Asn Val Leu Leu Gln Ile Asp Asn
            180                 185                 190

Ala Arg Leu Ala Ala Asp Asp Phe Arg Thr Lys Tyr Glu Thr Glu Leu
            195                 200                 205

Asn Leu Arg Met Ser Val Glu Ala Asp Ile Asn Gly Leu Arg Arg Val
            210                 215                 220

Leu Asp Glu Leu Thr Leu Ala Arg Ala Asp Leu Glu Met Gln Ile Glu
225                 230                 235                 240

Ser Leu Lys Glu Glu Leu Ala Tyr Leu Lys Lys Asn His Glu Glu Glu
                245                 250                 255

Met Asn Ala Leu Arg Gly Gln Val Gly Gly Asp Val Asn Val Glu Met
            260                 265                 270

Asp Ala Ala Pro Gly Val Asp Leu Ser Arg Ile Leu Asn Glu Met Arg
            275                 280                 285

Asp Gln Tyr Glu Lys Met Ala Glu Lys Asn Arg Lys Asp Ala Glu Glu
            290                 295                 300

Trp Phe Phe Thr Lys Thr Glu Glu Leu Asn Arg Glu Val Ala Thr Asn
305                 310                 315                 320

Ser Glu Leu Val Gln Ser Gly Lys Ser Glu Ile Ser Glu Leu Arg Arg

```
                       325                 330                 335
Thr Met Gln Asn Leu Glu Ile Glu Leu Gln Ser Gln Leu Ser Met Lys
                   340                 345                 350
Ala Ser Leu Glu Asn Ser Leu Glu Glu Thr Lys Gly Arg Tyr Cys Met
                355                 360                 365
Gln Leu Ala Gln Ile Gln Glu Met Ile Gly Ser Val Glu Glu Gln Leu
            370                 375                 380
Ala Gln Leu Arg Cys Glu Met Glu Gln Asn Gln Gly Tyr Lys Ile
385                 390                 395                 400
Leu Leu Asp Val Lys Thr Arg Leu Glu Gln Glu Ile Ala Thr Tyr Arg
                405                 410                 415
Arg Leu Leu Glu Gly Glu Asp Ala His Leu Ser Ser Ser Gln Phe Ser
                420                 425                 430
Ser Gly Ser Gln Ser Ser Arg Asp Val Thr Ser Ser Arg Gln Ile
            435                 440                 445
Arg Thr Lys Val Met Asp Val His Asp Gly Lys Val Val Ser Thr His
            450                 455                 460
Glu Gln Val Leu Arg Thr Lys Asn
465                 470

<210> SEQ ID NO 14
<211> LENGTH: 432
<212> TYPE: PRT
<213> ORGANISM: Homo sapiens

<400> SEQUENCE: 14

Met Thr Thr Ser Ile Arg Gln Phe Thr Ser Ser Ser Ile Lys Gly
1               5                   10                  15
Ser Ser Gly Leu Gly Gly Gly Ser Ser Arg Thr Ser Cys Arg Leu Ser
                20                  25                  30
Gly Gly Leu Gly Ala Gly Ser Cys Arg Leu Gly Ser Ala Gly Gly Leu
            35                  40                  45
Gly Ser Thr Leu Gly Gly Ser Ser Tyr Ser Ser Cys Tyr Ser Phe Gly
        50                  55                  60
Ser Gly Gly Gly Tyr Gly Ser Ser Phe Gly Gly Val Asp Gly Leu Leu
65                  70                  75                  80
Ala Gly Gly Glu Lys Ala Thr Met Gln Asn Leu Asn Asp Arg Leu Ala
                85                  90                  95
Ser Tyr Leu Asp Lys Val Arg Ala Leu Glu Glu Ala Asn Thr Glu Leu
                100                 105                 110
Glu Val Lys Ile Arg Asp Trp Tyr Gln Arg Gln Ala Pro Gly Pro Ala
            115                 120                 125
Arg Asp Tyr Ser Gln Tyr Tyr Arg Thr Ile Glu Glu Leu Gln Asn Lys
        130                 135                 140
Ile Leu Thr Ala Thr Val Asp Asn Ala Asn Ile Leu Leu Gln Ile Asp
145                 150                 155                 160
Asn Ala Arg Leu Ala Ala Asp Asp Phe Arg Thr Lys Phe Glu Thr Glu
                165                 170                 175
Gln Ala Leu Arg Leu Ser Val Glu Ala Asp Ile Asn Gly Leu Arg Arg
            180                 185                 190
Val Leu Asp Glu Leu Thr Leu Ala Arg Ala Asp Leu Glu Met Gln Ile
        195                 200                 205
Glu Asn Leu Lys Glu Glu Leu Ala Tyr Leu Lys Lys Asn His Glu Glu
210                 215                 220
```

Glu Met Asn Ala Leu Arg Gly Gln Val Gly Glu Ile Asn Val Glu
225                 230                 235                 240

Met Asp Ala Ala Pro Gly Val Asp Leu Ser Arg Ile Leu Asn Glu Met
                245                 250                 255

Arg Asp Gln Tyr Glu Lys Met Ala Glu Lys Asn Arg Lys Asp Ala Glu
            260                 265                 270

Asp Trp Phe Phe Ser Lys Thr Glu Glu Leu Asn Arg Glu Val Ala Thr
        275                 280                 285

Asn Ser Glu Leu Val Gln Ser Gly Lys Ser Glu Ile Ser Glu Leu Arg
    290                 295                 300

Arg Thr Met Gln Ala Leu Glu Ile Glu Leu Gln Ser Gln Leu Ser Met
305                 310                 315                 320

Lys Ala Ser Leu Glu Gly Asn Leu Ala Glu Thr Glu Asn Arg Tyr Cys
                325                 330                 335

Val Gln Leu Ser Gln Ile Gln Gly Leu Ile Gly Ser Val Glu Glu Gln
            340                 345                 350

Leu Ala Gln Leu Arg Cys Glu Met Glu Gln Gln Asn Gln Glu Tyr Lys
        355                 360                 365

Ile Leu Leu Asp Val Lys Thr Arg Leu Glu Gln Glu Ile Ala Thr Tyr
    370                 375                 380

Arg Arg Leu Leu Glu Gly Glu Asp Ala His Leu Thr Gln Tyr Lys Lys
385                 390                 395                 400

Glu Pro Val Thr Thr Arg Gln Val Arg Thr Ile Val Glu Glu Val Gln
                405                 410                 415

Asp Gly Lys Val Ile Ser Ser Arg Glu Gln Val His Thr Thr Arg
            420                 425                 430

<210> SEQ ID NO 15
<211> LENGTH: 19
<212> TYPE: PRT
<213> ORGANISM: Homo sapiens

<400> SEQUENCE: 15

Tyr Glu Glu Leu Gln Gln Thr Ala Gly Arg His Gly Asp Asp Leu Arg
1               5                   10                  15

Asn Thr Lys

<210> SEQ ID NO 16
<211> LENGTH: 19
<212> TYPE: PRT
<213> ORGANISM: Mus musculus

<400> SEQUENCE: 16

Tyr Glu Glu Leu Gln Val Thr Ala Gly Arg His Gly Asp Asp Leu Arg
1               5                   10                  15

Asn Thr Lys

<210> SEQ ID NO 17
<211> LENGTH: 12
<212> TYPE: PRT
<213> ORGANISM: Mus musculus

<400> SEQUENCE: 17

Arg Thr Lys Ala Glu Asn Glu Phe Val Thr Val Lys
1               5                   10

<210> SEQ ID NO 18
<211> LENGTH: 21

```
<212> TYPE: PRT
<213> ORGANISM: Mus musculus

<400> SEQUENCE: 18

Ala Gln Tyr Glu Asp Ile Ala Gln Arg Ser Arg Ala Glu Ala Glu Ser
1               5                   10                  15

Trp Tyr Gln Thr Lys
            20

<210> SEQ ID NO 19
<211> LENGTH: 21
<212> TYPE: PRT
<213> ORGANISM: Rattus norvegicus

<400> SEQUENCE: 19

Ala Gln Tyr Glu Glu Ile Ala Lys Arg Ser Arg Ala Glu Ala Glu Ser
1               5                   10                  15

Trp Tyr Gln Thr Lys
            20

<210> SEQ ID NO 20
<211> LENGTH: 12
<212> TYPE: PRT
<213> ORGANISM: Homo sapiens

<400> SEQUENCE: 20

Arg Thr Thr Ala Glu Asn Glu Phe Val Met Leu Lys
1               5                   10

<210> SEQ ID NO 21
<211> LENGTH: 21
<212> TYPE: PRT
<213> ORGANISM: Homo sapiens

<400> SEQUENCE: 21

Ala Gln Tyr Glu Glu Ile Ala Asn Arg Ser Thr Glu Ala Glu Ser
1               5                   10                  15

Trp Tyr Gln Thr Lys
            20

<210> SEQ ID NO 22
<211> LENGTH: 21
<212> TYPE: PRT
<213> ORGANISM: Bos taurus

<400> SEQUENCE: 22

Ala Gln Tyr Glu Asp Ile Ala Asn Arg Ser Arg Thr Glu Ala Glu Ser
1               5                   10                  15

Trp Tyr Gln Thr Lys
            20

<210> SEQ ID NO 23
<211> LENGTH: 10
<212> TYPE: PRT
<213> ORGANISM: Homo sapiens

<400> SEQUENCE: 23

Thr Lys Tyr Glu Thr Glu Leu Asn Leu Arg
1               5                   10

<210> SEQ ID NO 24
<211> LENGTH: 10
<212> TYPE: PRT
```

<213> ORGANISM: Rattus norvegicus

<400> SEQUENCE: 24

Thr Lys Phe Glu Thr Glu Gln Ser Leu Arg
1               5                   10

<210> SEQ ID NO 25
<211> LENGTH: 24
<212> TYPE: PRT
<213> ORGANISM: Homo sapiens

<400> SEQUENCE: 25

Gln Phe Thr Ser Ser Ser Ser Met Lys Gly Ser Cys Gly Ile Gly Gly
1               5                   10                  15

Gly Ile Gly Gly Gly Ser Ser Arg
            20

<210> SEQ ID NO 26
<211> LENGTH: 20
<212> TYPE: PRT
<213> ORGANISM: Rattus norvegicus

<400> SEQUENCE: 26

Gln Phe Thr Ser Ser Ser Ser Met Lys Gly Ser Cys Gly Ile Gly Gly
1               5                   10                  15

Gly Ser Ser Arg
            20

<210> SEQ ID NO 27
<211> LENGTH: 23
<212> TYPE: PRT
<213> ORGANISM: Bos taurus

<400> SEQUENCE: 27

Thr Ile Val Glu Glu Val Gln Asp Gly Arg Val Ile Ser Ser Arg Glu
1               5                   10                  15

Gln Val His Gln Thr Ser His
            20

<210> SEQ ID NO 28
<211> LENGTH: 15
<212> TYPE: PRT
<213> ORGANISM: Bos taurus

<400> SEQUENCE: 28

Thr Ile Val Glu Glu Val Gln Asp Gly Arg Val Ile Ser Ser Arg
1               5                   10                  15

<210> SEQ ID NO 29
<211> LENGTH: 20
<212> TYPE: PRT
<213> ORGANISM: Bos taurus

<400> SEQUENCE: 29

Arg His Phe Ser Ser Gly Ser Ile Lys Gly Ser Ser Gly Leu Ala Gly
1               5                   10                  15

Gly Ser Ser Arg
            20

<210> SEQ ID NO 30
<211> LENGTH: 20
<212> TYPE: PRT
<213> ORGANISM: Pan troglodytes

```
-continued

<400> SEQUENCE: 30

Glu Val Ala Thr Asn Ser Glu Leu Val Gln Ser Gly Glu Ser Glu Ile
1               5                   10                  15

Ser Glu Leu Arg
            20
```